United States Patent
Yam et al.

(10) Patent No.: US 12,099,061 B2
(45) Date of Patent: Sep. 24, 2024

(54) NIDOGEN 1 AS A DIAGNOSTIC MARKER AND THERAPEUTIC TARGET OF HEPATOCELLULAR CARCINOMA, COMPOSITION AND METHODS THEREOF

(71) Applicant: THE UNIVERSITY OF HONG KONG, Hong Kong (CN)

(72) Inventors: Wai Ping Judy Yam, Hong Kong (CN); Xiaowen Mao, Hong Kong (CN); Sze Keong Tey, Hong Kong (CN)

(73) Assignee: THE UNIVERSITY OF HONG KONG, Hong Kong (CN)

( * ) Notice: Subject to any disclaimer, the term of this patent is extended or adjusted under 35 U.S.C. 154(b) by 159 days.

(21) Appl. No.: 17/237,433

(22) Filed: Apr. 22, 2021

(65) Prior Publication Data

US 2021/0356468 A1    Nov. 18, 2021

Related U.S. Application Data

(60) Provisional application No. 63/014,179, filed on Apr. 23, 2020.

(51) Int. Cl.
| | | |
|---|---|---|
| *G01N 33/574* | (2006.01) | |
| *A61K 39/00* | (2006.01) | |
| *A61P 35/00* | (2006.01) | |
| *C07K 16/18* | (2006.01) | |
| *C07K 16/28* | (2006.01) | |

(52) U.S. Cl.
CPC ........ *G01N 33/57438* (2013.01); *A61P 35/00* (2018.01); *C07K 16/18* (2013.01); *C07K 16/2878* (2013.01); *A61K 2039/505* (2013.01); *G01N 2333/46* (2013.01); *G01N 2333/70578* (2013.01)

(58) Field of Classification Search
CPC ........ G01N 33/57438; G01N 2333/46; G01N 2333/70578; A61P 35/00; A61K 2039/505; C07K 16/18; C07K 16/2878
See application file for complete search history.

(56) References Cited

FOREIGN PATENT DOCUMENTS

| | | | | |
|---|---|---|---|---|
| WO | WO-2010076932 A1 | * | 7/2010 | ......... A61K 38/1709 |
| WO | WO-2019206974 A1 | * | 10/2019 | ............... A61P 35/00 |

OTHER PUBLICATIONS

Posnett et al (A novel method for producing anti-peptide antibodies, Jour Biol Chem, vol. 263(4), pp. 1719-1725, 1988) (Year: 1988).*
Mao et al (Exosomal nidogen 1 drives liver cancer metastasis by inducing secretions of tumor necrosis factor receptor 1 from activated lung fibroblasts, Jour Extracellular Vesicles, vol. 8, 2019) (Year: 2019).*
J. Berg, et al. "Levels and prognostic impact of circulating markers of inflammation, endothelial activation and extracellular matrix remodelling in patients with lung cancer and chronic obstructive pulmonary disease", BMC Cancer 2018, 18, 739. 10 pages.
A. C. Carlsson, et al. "Soluble tumor necrosis factor receptor 1 (sTNFR1) is associated with increased total mortality due to cancer and cardiovascular causes e Findings from two community based cohorts of elderly", Atherosclerosis 2014, 237, 236. 7 pages.
G. B. McDonald, et al., "Plasma biomarkers of acute GVHD and nonrelapse mortality: predictive value of measurements before GVHD onset and treatment", Blood 2015, 126, 113. 8 pages.
Y. Zhang, et al., "The ovarian cancer-derived secretory/releasing proteome: A repertoire of tumor markers", Proteomics 2012, 12, 1883. 9 pages.
C. W. Hsu, et al., "Proteomic Profiling of Paired Interstitial Fluids Reveals Dysregulated Pathways and Salivary NID1 as a Biomarker of Oral Cavity Squamous Cell Carcinoma", Mol Cell Proteomics 2019, 18, 1939. 12 pages.
F. Bertrand, et al., "TNFα blockade overcomes resistance to anti-PD-1 in experimental melanoma", Nat Commun 2017, 8, 2256. 13 pages.
F. Van Hauwermeiren, et al., "Safe TNF-based antitumor therapy following p55TNFR reduction in intestinal epithelium", J Clin Invest 2013, 123, 2590. 15 pages.
L. Niu, et al., "New insights into sorafenib resistance in hepatocellular carcinoma: Responsible mechanisms and promising strategies", Biochim Biophys Acta Rev Cancer 2017, 1868, 564. 7 pages.
L. Hu, Jet al., "Establishment of cell lines from a primary hepatocellular carcinoma and its metastatis", Cancer Genet Cytogenet 2004, 148, 80. 5 pages.
J. J. Brown, et al., "A Long-Term Hepatitis B Viremia Model Generated by Transplanting Nontumorigenic Immortalized Human Hepatocytes in Rag-2-Deficient Mice", Hepatology 2000, 31, 173. 9 pages.
W. Xue, et al., "A cluster of cooperating tumor-suppressor gene candidates in chromosomal deletions", Proc Natl Acad Sci U S A 2012, 109, 8212. 6 pages.

(Continued)

*Primary Examiner* — Mark Halvorson
*Assistant Examiner* — Dennis J Sullivan
(74) *Attorney, Agent, or Firm* — Leason Ellis LLP

(57) ABSTRACT

The present disclosure provides methods and compositions for treatment, screening, diagnosis and prognosis of hepatocellular carcinoma with extrahepatic metastasis. Provided herein are methods and compositions for treatment, screening, diagnosis and prognosis of metastatic cancers. Also provided are antibodies and compositions for the treatment of cancers. Provided herein is therapeutic target for the treatment of cancers or as a marker for cancers. In particular, the protein represents a biological target against which affinity molecules including therapeutic antibodies, or other pharmaceutical agents, can be made. The disclosure also relates to the use of such affinity molecules for the treatment and/or diagnosis of cancers.

Figure 1A:
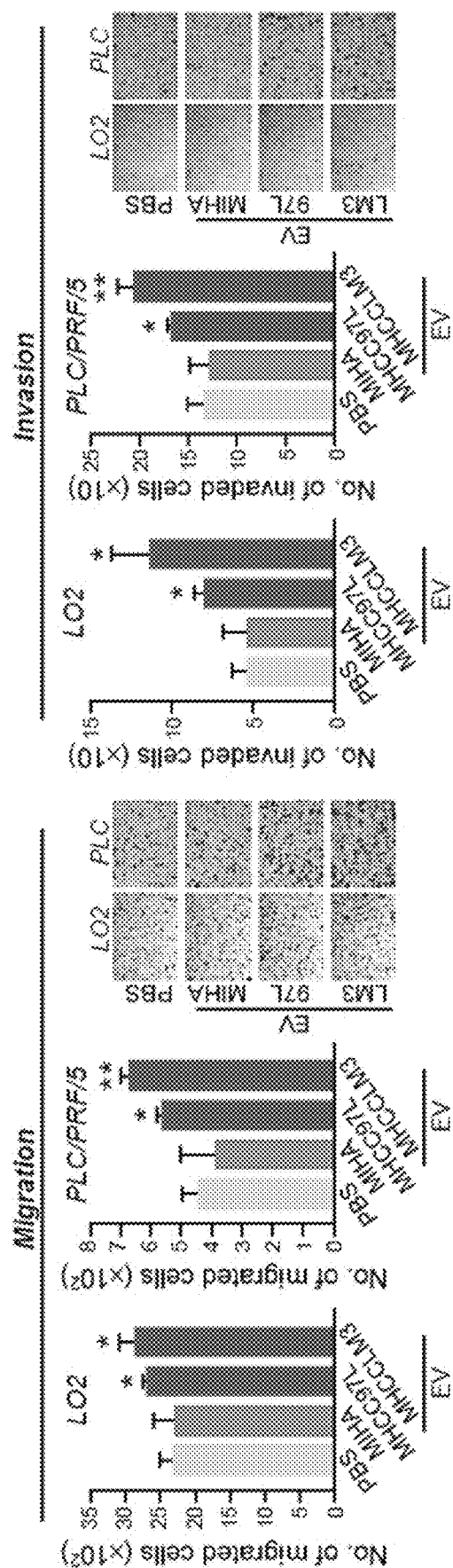
Figure 1C:
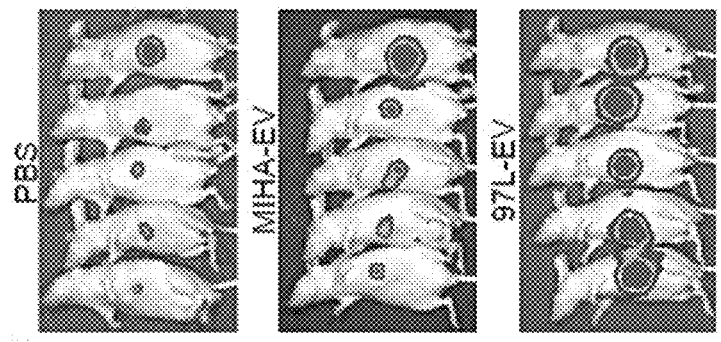
Figure 1B:
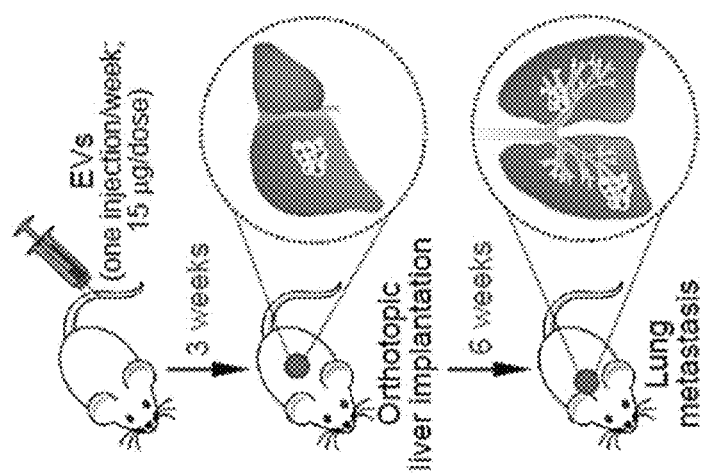

13 Claims, 88 Drawing Sheets
(81 of 88 Drawing Sheet(s) Filed in Color)
Specification includes a Sequence Listing.

(56) References Cited

OTHER PUBLICATIONS

Y. Perez-Riverol, et al., "The PRIDE database and related tools and resources in 2019: improving support for quantification data", Nucleic Acids Res 2019, 47, D442. 9 pages.
D. F. Quail, J. A. Joyce, "Microenvironmental regulation of tumor progression and metastasis", Nat Med 2013, 19, 1423. 15 pages.
J. Skog, et al, "Glioblastoma microvesicles transport RNA and proteins that promote tumour growth and provide diagnostic biomarkers", Nat Cell Biol 2008, 10, 1470. 12 pages.
T. Kogure, et al., "Intercellular Nanovesicle-Mediated microRNA Transfer: A Mechanism of Environmental Modulation of Hepatocellular Cancer Cell Growth", Hepatology 2011, 54, 1237. 12 pages.
K. Al-Nedawi, et al., "Intercellular transfer of the oncogenic receptor EGFRvlll by microvesicles derived from tumour cells", Nat Cell Biol 2008, 10, 619. 26 pages.
J. Paggetti, et al., "Exosomes released by chronic lymphocytic leukemia cells induce the transition of stromal cells into cancer-associated fibroblasts", Blood 2015, 126, 1106. 12 pages.
B. Costa-Silva, et al., "Pancreatic cancer exosomes initiate pre-metastatic niche formation in the liver", Nat Cell Biol 2015, 17, 816. 20 pages.
H. Peinado, et al., "Melanoma exosomes educate bone marrow progenitor cells toward a pro-metastatic phenotype through MET", Nat Med 2012, 18, 883. 13 pages.
N. Erez, et al., "Cancer-Associated Fibroblasts Are Activated in Incipient Neoplasia to Orchestrate Tumor-Promoting Inflammation in an NF-kB-Dependent Manner", Cancer Cell 2010, 17, 135.
A. Costa, et al., "Fibroblast Heterogeneity and Immunosuppressive Environment in Human Breast Cancer", Cancer Cell 2018, 33, 463. 28 pages.
M. Kraman, et al., Suppression of Antitumor Immunity by Stromal Cells Expressing Fibroblast Activation Protein-a, Science 2010, 330, 827. 5 pages.
E. Y. Lau, et al., "Cancer-Associated Fibroblasts Regulate Tumor-Initiating Cell Plasticity in Hepatocellular Carcinoma through c-Met/FRA1/HEY1 Signaling", Cell Rep 2016, 15, 1175. 16 pages.
A. Mazzocca, et al., "Down-Regulation of Connective Tissue Growth Factor by Inhibition of Transforming Growth Factor B Blocks the Tumor-Stroma Cross-Talk and Tumor Progression in Hepatocellular Carcinoma", Hepatology 2010, 51, 523. 12 pages.
C. J. Hanley, et al., "Targeting the Myofibroblastic Cancer-Associated Fibroblast Phenotype Through Inhibition of NOX4", J Natl Cancer Inst 2018, 110, 109. 12 pages.
X. Y. Yang, et al., "Association of tumor-associated fibroblasts with progression of hepatocellular carcinoma", Med Oncol 2013, 30, 593. 6 pages.
J. Ji, T. Eggert, et al., "Hepatic Stellate Cell and Monocyte Interaction Contributes to Poor Prognosis in Hepatocellular Carcinoma", Hepatology 2015, 62, 481. 15 pages.
A. Duseja, "Staging of Hepatocellular Carcinoma", Journal of clinical and experimental hepatology 2014, 4, S74. 6 pages.
F. X. Sun, et al., "Establishment of a Metastatic Model of Human Hepatocellular Carcinoma in Nude Mice Via Orthotopic Implantation of Histologically Intact Tissues", International journal of cancer 1996, 66, 239. 5 pages.
A. Datta, et al., "High-throughput screening identified selective inhibitors of exosome biogenesis and secretion: A drug repurposing strategy for advanced cancer", Sci Rep 2018, 8, 8161. 13 pages.
M. E. Balasis, et al., "Combination of Farnesyltransferase and Akt Inhibitors Is Synergistic in Breast Cancer Cells and Causes Significant Breast Tumor Regression in ErbB2 Transgenic Mice", Clinical cancer research : an official journal of the American Association for Cancer Research 2011, 17, 2852. 11 pages.
B. R. Untch, et al., "Tipifarnib Inhibits HRAS-Driven Dedifferentiated Thyroid Cancers", Cancer Res 2018, 78, 4642. 16 pages.
Y. Huang, et al., "Pulmonary Vascular Destabilization in the Premetastatic Phase Facilitates Lung Metastasis", Cancer Res 2009, 69, 7529. 9 pages.
Y. Zhou, et al., "NID1, a new regulator of EMT required for metastasis and chemoresistance of ovarian cancer cells", Oncotarget 2017, 8, 33110. 12 pages.
N. Pedrola, et al., "Nidogen 1 and Nuclear Protein 1: novel targets of ETV5 transcription factor involved in endometrial cancer invasion", Clinical & experimental metastasis 2015, 32, 467. 12 pages.
M. Aleckovic, et al., "Identification of Nidogen 1 as a lung metastasis protein through secretome analysis", Genes Dev 2017, 31, 1439. 18 pages.
H. Peinado, et al., "Pre-metastatic niches: organ-specific homes for metastases", Nat Rev Cancer 2017, 17, 302. 16 pages.
J. T. O'Connell, et al., "VEGF-A and Tenascin-C produced by S100A4+ stromal cells are important for metastatic colonization", Proc Natl Acad Sci U S A 2011, 108, 16002. 6 pages.
M. Q. Kwa, et al., "Cancer-associated fibroblasts: how do they contribute to metastasis?" Clin Exp Metastas 2019, 36, 71. 16 pages.
M. He, et al., "Hepatocellular carcinoma-derived exosomes promote motility of immortalized hepatocyte through transfer of oncogenic proteins and RNAs", Carcinogenesis 2015, 36, 1008. 11 pages.
L. Chen, et al., "HCC-derived exosomes elicit HCC progression and recurrence by epithelialmesenchymal transition through MAPK/ERK signalling pathway", Cell Death Dis 2018, 9, 513. 17 pages.
X. J. Lin, et al., "Hepatocellular Carcinoma Cell-Secreted Exosomal MicroRNA-210 Promotes Angiogenesis In Vitro and In Vivo", Mol Ther Nucleic Acids 2018, 11, 243. 10 pages.
H. Liu, et al., "Tumor-derived exosomes promote tumor self-seeding in hepatocellular carcinoma by transferring miRNA-25-5p to enhance cell motility", Oncogene 2018, 37, 4964. 15 pages.
J. H. Fang, et al., "Hepatoma Cell-Secreted Exosomal microRNA-103 Increases Vascular Permeability and Promotes Metastasis by Targeting Junction Proteins", Hepatology 2018, 68, 1459. 17 pages.
X. Fu, et al., "Exosomal microRNA-32-5p induces multidrug resistance in hepatocellular carcinoma via the PI3K/Akt pathway", J Exp Clin Cancer Res 2018, 37, 52. 18 pages.
T. Fang, et al., "Tumor-derived exosomal miR-1247-3p induces cancer-associated fibroblast activation to foster lung metastasis of liver cancer", Nat Commun 2018, 9, 191. 13 pages.
J. Liu, L. Fan, et al., "Endoplasmic Reticulum Stress Causes Liver Cancer Cells to Release Exosomal miR-23a-3p and Up-regulate Programmed Death Ligand 1 Expression in Macrophages", Hepatology 2019, 70, 241. 18 pages.
S. Zhao, J. Li, et al., "Exosomal miR-451a Functions as a Tumor Suppressor in Hepatocellular Carcinoma by Targeting LPIN1", Cell Physiol Biochem 2019, 53, 19. 17 pages.
Y. Wang, et al., "miR-125a/b inhibits tumor-associated macrophages mediated in cancer stem cells of hepatocellular carcinoma by targeting CD90", J Cell Biochem 2019, 120, 3046. 10 pages.
J. Zhang, et al., "Motile hepatocellular carcinoma cells preferentially secret sugar metabolism regulatory proteins via exosomes", Proteomics 2017, 17, 1700103. 13 pages.
C. J. Ko, et al., "Androgen-Induced TMPRSS2 Activates Matriptase and Promotes Extracellular Matrix Degradation, Prostate Cancer Cell Invasion, Tumor Growth, and Metastasis", Cancer Res 2015, 75, 2949. 12 pages.
D. A. Ferraro, et al. "Endothelial cell-derived nidogen-1 inhibits migration of SK-BR-3 breast cancer cells", BMC Cancer 2019, 19, 312. 13 pages.
I. Lazar, et al., "Proteome characterization of melanoma exosomes reveals a specific signature for metastatic cell lines", Pigment Cell Melanoma Res 2015, 28, 464. 12 pages.
Y. K. Chan, et al., "Proteomic analysis of exosomes from nasopharyngeal carcinoma cell identifies intercellular transfer of angiogenic proteins", Int J Cancer 2015, 137, 1830. 12 pages.
P. A. Gonzales, et al.,"Large-Scale Proteomics and Phosphoproteomics of Urinary Exosomes", J Am Soc Nephrol 2009, 20, 363. 125 pages.
H. Nakagawa, et al., "ER Stress Cooperates with Hypernutrition to Trigger TNF-Dependent Spontaneous HCC Development", Cancer Cell 2014, 26, 331. 13 pages.
F. I. Hawari, F. et al., "Release of full-length 55-kDa TNF receptor 1 in exosome-like vesicles: A mechanism for generation of soluble cytokine receptors", Proc Natl Acad Sci U S A 2004, 101, 1297. 6 pages.

(56) References Cited

OTHER PUBLICATIONS

J. H. Bell, et al., "Role of ADAM17 in the ectodomain shedding of TNF– and its receptors by neutrophils and macrophages", J Leukoc Biol 2007, 82, 173. 4 pages.

A. Murthy, et al., "Ectodomain shedding of EGFR ligands and TNER1 dictates hepatocyte apoptosis during fulminant hepatitis in mice", J Clin Invest 2010, 120, 2731. 15 pages.

A. N. Abety, et al., "Stromal Fibroblast—Specific Expression of ADAM-9 Modulates Proliferation and Apoptosis in Melanoma Cells In Vitro and In Vivo", J Invest Dermatol 2012, 132, 2451. 8 pages.

L. Dossus, Set al., "Tumor necrosis factor (TNF)-a, soluble TNF receptors and endometrial cancer risk: the EPIC study", Int J Cancer 2011, 129, 2032. 6 pages.

M. S. Ahluwalia, et al., "Correlation of higher levels of soluble TNF-R1 with a shorter survival, independent of age, in recurrent glioblastoma", J Neurooncol 2017, 131, 449. 10 pages.

\* cited by examiner

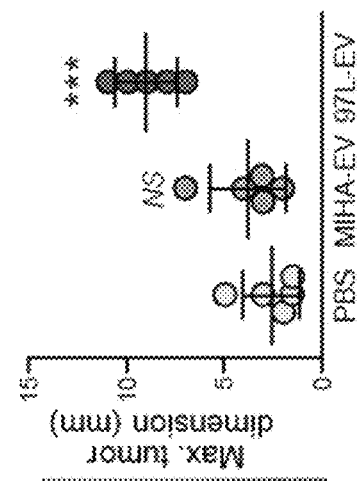
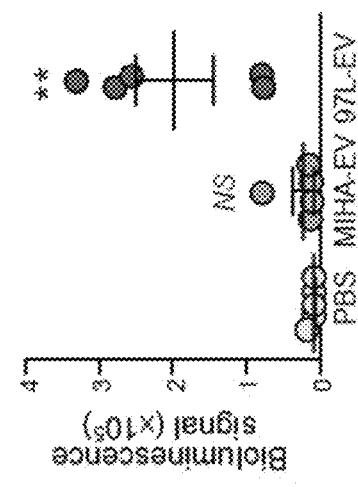
FIG. 1D
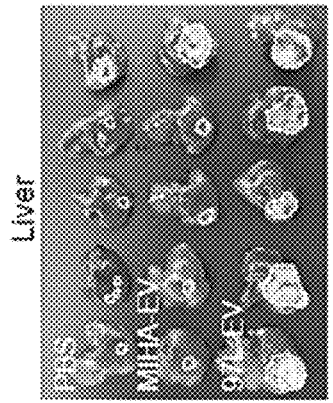
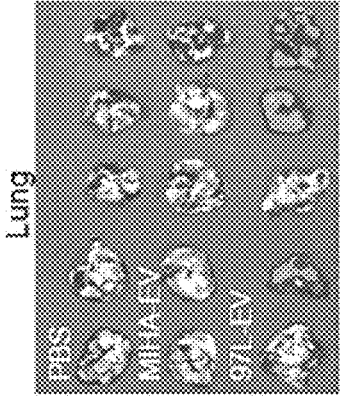
FIG. 1E

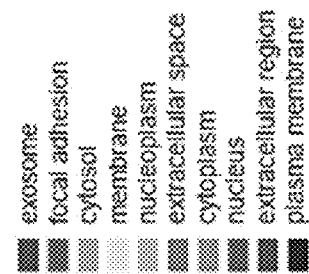
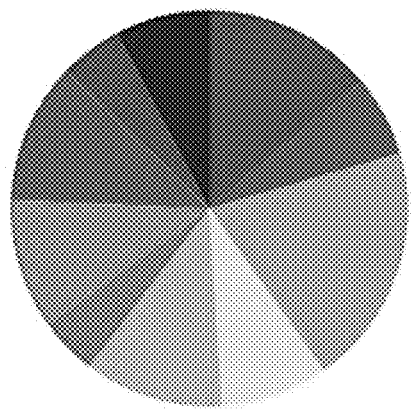
FIG. 3B
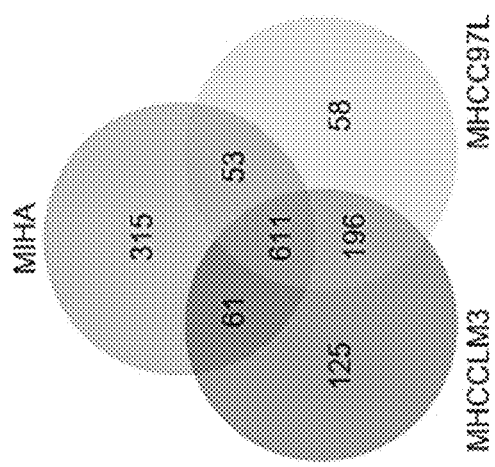
FIG. 3A

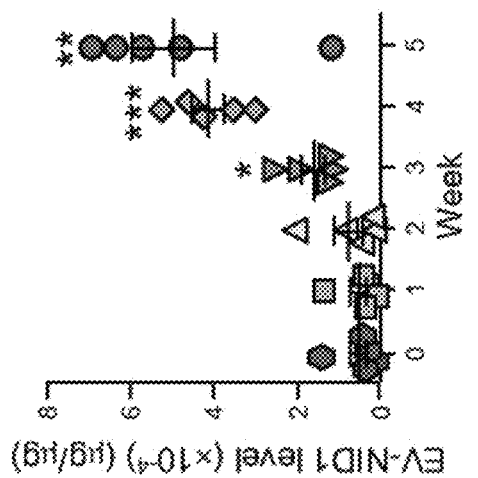
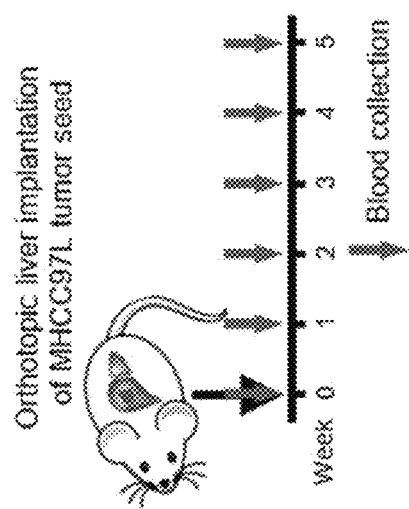
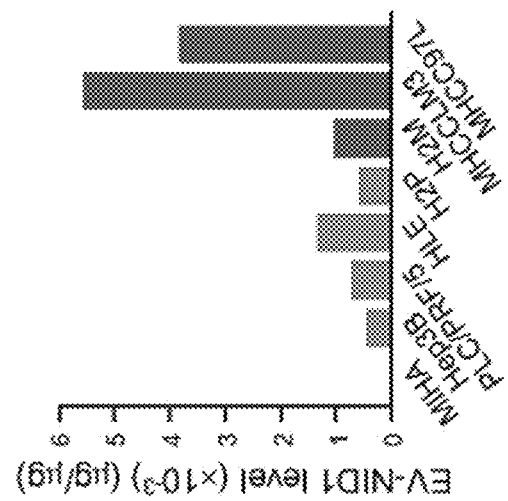
FIG. 3F
FIG. 3G

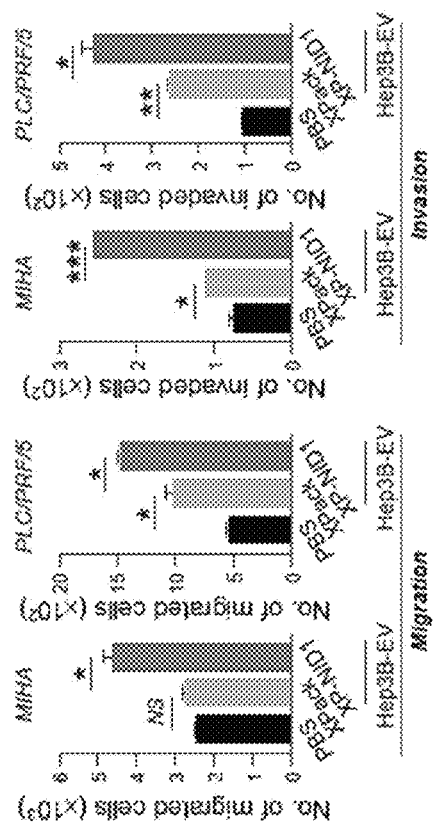
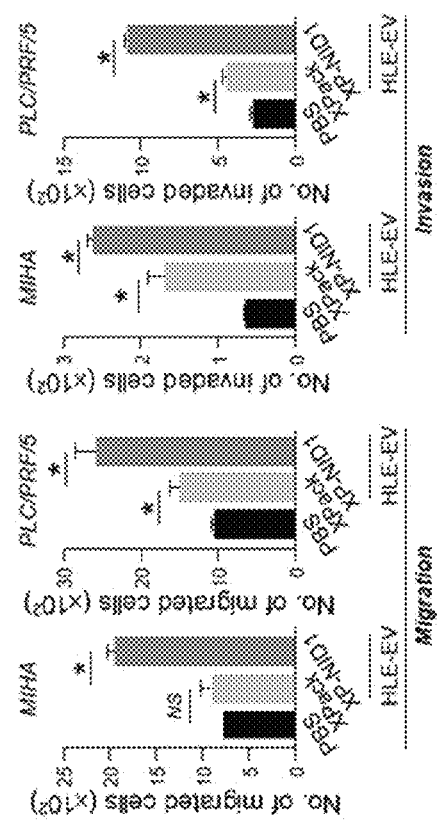
FIG. 4C
FIG. 4D

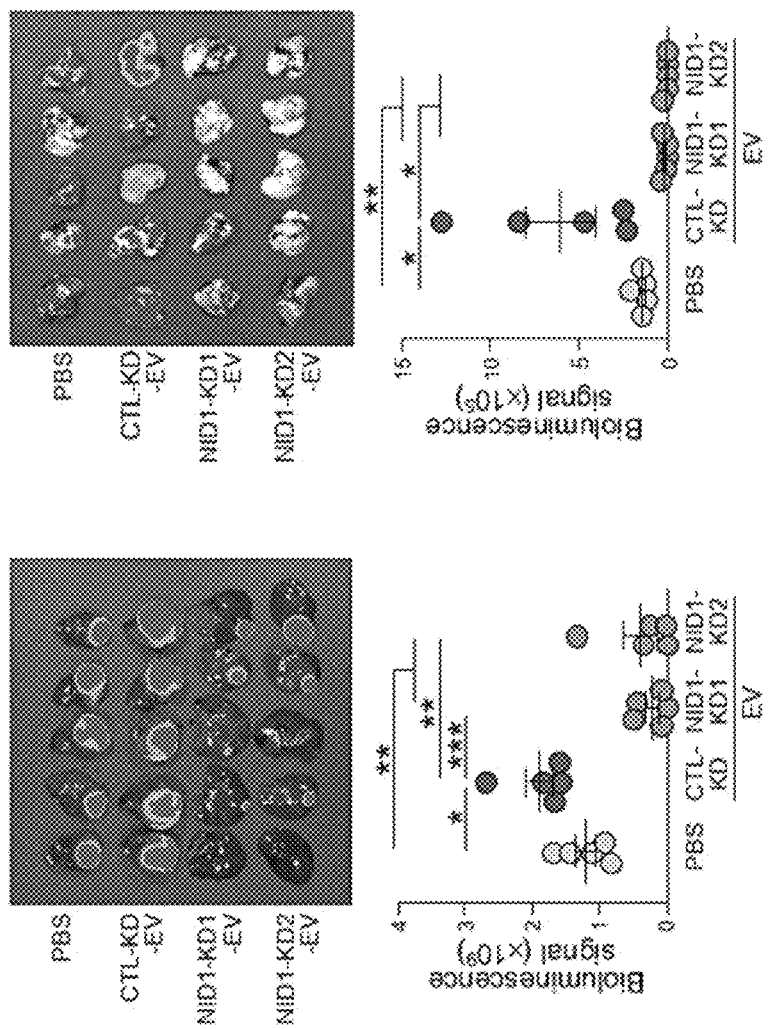

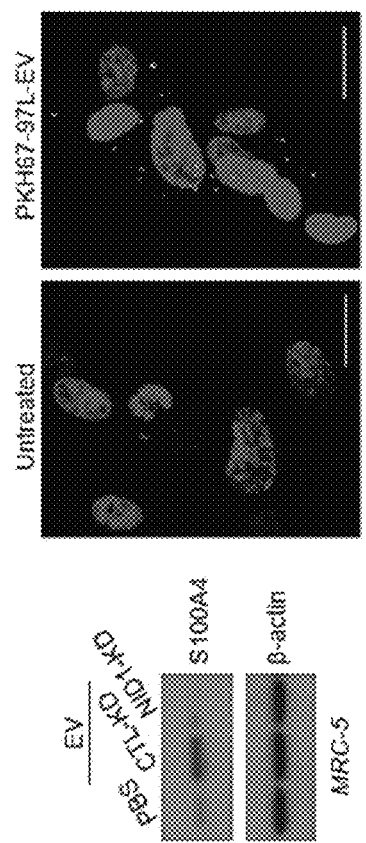
FIG. 6C
FIG. 6B
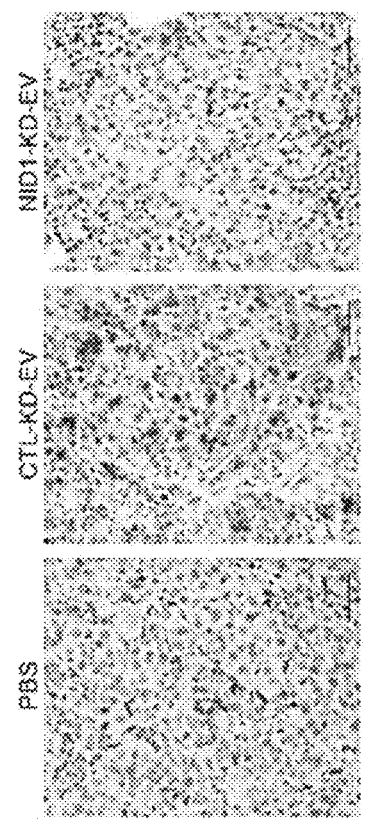
FIG. 6A

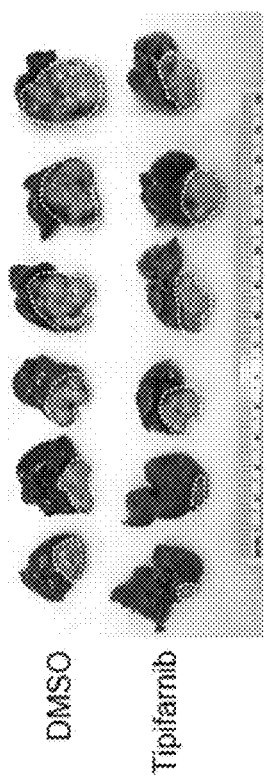
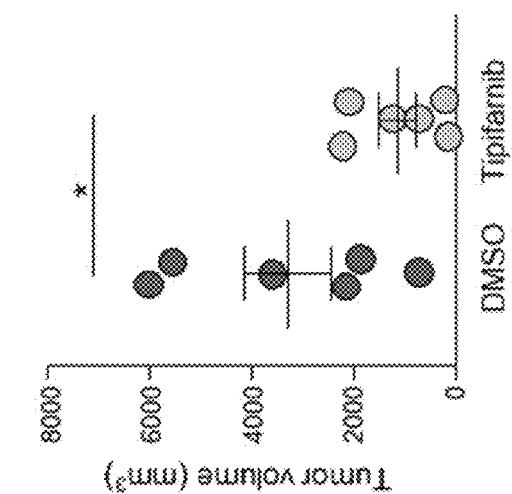
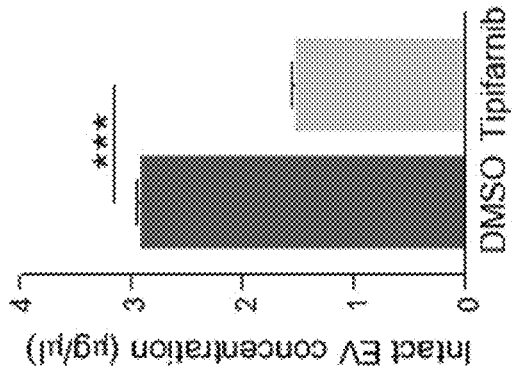
FIG. 11A
FIG. 11B

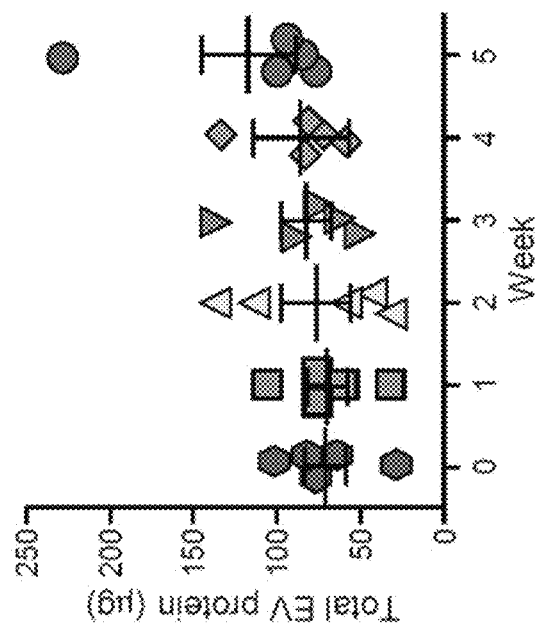
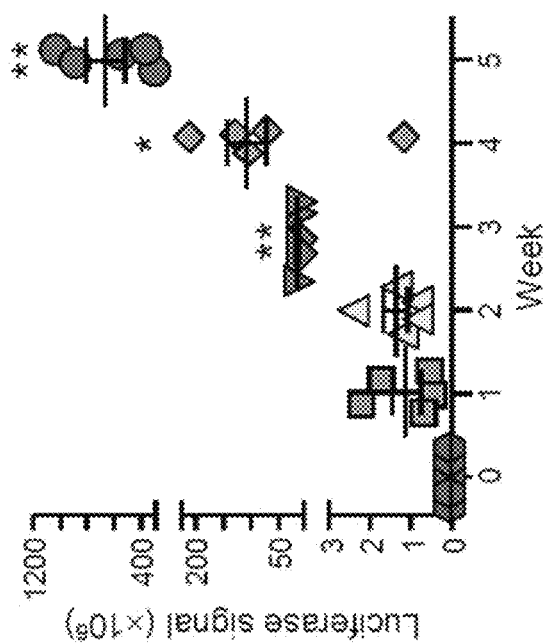
FIG. 13B
FIG. 13C

| Protein name | Number of peptides | MW (kDa) | Average intensity of proteins |
|---|---|---|---|
| ANXA2 | 18 | 38.604 | 5.016E+08 |
| CFB | 29 | 139.09 | 4.912E+08 |
| NID1 | 13 | 136.38 | 2.642E+08 |
| ACTN4 | 18 | 104.85 | 2.087E+08 |
| MDK | 6 | 14.374 | 1.718E+08 |
| SERPINE2 | 9 | 44.002 | 1.474E+08 |
| G6PD | 13 | 59.256 | 1.411E+08 |
| FCGBP | 10 | 445.21 | 1.155E+08 |
| COL18A1 | 11 | 178.19 | 1.069E+08 |
| GPC1 | 11 | 53.964 | 9.492E+07 |
| COL2A1 | 4 | 141.78 | 7.806E+07 |
| PLEC | 28 | 531.78 | 7.443E+07 |
| SERPINE1 | 5 | 45.059 | 7.367E+07 |
| ANXA3 | 3 | 36.374 | 6.197E+07 |
| FBLN1 | 18 | 78.329 | 5.343E+07 |
| AKR1B10 | 6 | 36.019 | 5.287E+07 |
| MET | 4 | 155.54 | 4.708E+07 |
| C1R | 15 | 83.289 | 4.168E+07 |
| S100A4 | 3 | 11.728 | 3.861E+07 |
| CLSTN1 | 5 | 109.79 | 3.625E+07 |
| NAMPT | 2 | 55.52 | 3.336E+07 |
| PGK1 | 4 | 44.614 | 3.307E+07 |
| NAP1L1 | 4 | 23.417 | 3.013E+07 |
| APOM | 2 | 14.185 | 2.567E+07 |
| HIST1H4A | 3 | 11.367 | 2.163E+07 |
| HIST1H2BH | 3 | 13.906 | 1.930E+07 |
| C1S | 9 | 76.684 | 1.769E+07 |
| TNC | 3 | 261.14 | 1.758E+07 |
| PLOD1 | 4 | 83.549 | 1.321E+07 |
| RPSA | 4 | 29.505 | 1.319E+07 |
| HNRNPK | 3 | 41.207 | 1.239E+07 |
| GANAB | 3 | 106.215 | 1.227E+07 |
| PRSS3 | 3 | 43.003 | 1.211E+07 |
| S100P | 3 | 10.4 | 1.176E+07 |
| EEF1D | 4 | 69.282 | 1.083E+07 |
| LDHB | 3 | 36.638 | 1.055E+07 |
| MVP | 2 | 99.326 | 9.553E+06 |
| ALDH3A1 | 3 | 41.647 | 9.506E+06 |
| HNRNPA1 | 3 | 33.155 | 9.341E+06 |
| C8B | 2 | 60.04 | 9.249E+06 |
| SRPX | 4 | 51.371 | 9.109E+06 |
| SNRPD3 | 2 | 13.916 | 8.930E+06 |
| MYL6 | 4 | 16.129 | 8.594E+06 |
| SDCBP | 5 | 32.444 | 7.687E+06 |
| CALM2 | 2 | 7.372 | 7.059E+06 |
| ARPC4 | 2 | 9.405 | 7.043E+06 |
| DKK1 | 5 | 28.671 | 6.733E+06 |
| SDC4 | 3 | 23.641 | 6.256E+06 |
| LTBP1 | 6 | 147.01 | 6.078E+06 |
| VPS35 | 2 | 91.708 | 5.913E+06 |
| PCOLCE2 | 2 | 45.716 | 5.570E+06 |
| HSPA2 | 2 | 40.244 | 4.871E+06 |
| S100A6 | 3 | 10.18 | 4.757E+06 |
| PYGB | 2 | 96.695 | 3.936E+06 |
| HSPA1L | 3 | 70.403 | 3.881E+06 |
| TUBAL3 | 2 | 49.908 | 3.860E+06 |
| HSPA5 | 3 | 72.332 | 3.744E+06 |
| TUBA1C | 13 | 57.73 | 2.987E+06 |
| ACTN1 | 13 | 103.06 | 2.892E+06 |
| DSP | 2 | 303.53 | 2.818E+06 |
| HBA2 | 5 | 11.948 | 2.667E+06 |
| KRT18 | 2 | 43.774 | 2.260E+06 |
| FAT1 | 2 | 506.37 | 1.936E+06 |
| FBN1 | 11 | 312.24 | 1.915E+06 |
| LOXL2 | 5 | 86.724 | 1.795E+06 |
| COL1A1 | 3 | 138.94 | 1.794E+06 |
| SLC3A2 | 5 | 64.872 | 1.784E+06 |
| LAMA4 | 2 | 201.82 | 1.573E+06 |
| SPTAN1 | 3 | 284.54 | 1.181E+06 |
| PSAP | 2 | 58.14 | 9.535E+05 |
| TTN | 3 | 3994.6 | 4.868E+05 |

FIG. 21

| Cytokine | CTL-KD-EV | NID1-KD1-EV |
|---|---|---|
| IGFBP1 | 3.165631 | 7.111735 |
| SCFD1 | 1.822941 | 1.930444 |
| TNFSF1A (TNFR1) | 1.745994 | 1.863790 |
| TMP2 | 1.745478 | 0.9279762 |
| TNFSF11B | 1.470831 | 1.250875 |
| IGF1 | 0.9904363 | 0.631813 |
| IGFBP2 | 0.5557277 | 1.564105 |
| TNFSF10D | 0.4770495 | 0.4877135 |
| TGFB3 | 0.3967455 | 1.016307 |
| LEP | 0.3919567 | 2.648289 |
| TNFSF14 | 0.0000000 | 1.582240e-011 |
| TNF-α | 4.664520e-011 | 4.869370e-010 |
| ADIPOQ | 7.849060e-012 | 7.009330e-012 |

FIG. 22

| Clinical parameters | Category | Number of patients |
|---|---|---|
| *HCC patients* | | |
| Gender | Male | 52 |
| | Female | 13 |
| Age | <50 | 21 |
| | 50-60 | 20 |
| | >60 | 24 |
| pTMN staging | I and II | 43 |
| | III and IV | 22 |
| *Control individuals* | | |
| Gender | Male | 11 |
| | Female | 1 |
| Age | <50 | 3 |
| | 50-60 | 2 |
| | >60 | 7 |

FIG. 23

| Primer name | Oligonucleotide sequence 5' to 3' |
| --- | --- |
| NID1-3111F | Forward: GATGAATTCCGTGGTTGCTC (SEQ ID NO: 1) |
| NID1-stopR | Reverse: CTAGCTAGCTCATTTCTGTTCGATACAGTCAA (SEQ ID NO: 2) |
| IGFBP1-F | Forward: TTGGGACGCCATCAGTACCTA (SEQ ID NO: 3) |
| IGFBP1-R | Reverse: TTGGCTAAACTCTCTACGACTCT (SEQ ID NO: 4) |
| SCFD1-F | Forward: ATGCAGCGTTAGCAGCTAGTG (SEQ ID NO: 5) |
| SCFD1-R | Reverse: GGCCTGTTAATGGCACGATATG (SEQ ID NO: 6) |
| TNFRSF1A-F | Forward: TCACCGCTTCAGAAAACCACC (SEQ ID NO: 7) |
| TNFRSF1A-R | Reverse: GGTCCACTGTGCAAGAAGAGA (SEQ ID NO: 8) |
| TIMP2-F | Forward: AAGCGGTCAGTGAGAAGGAAG (SEQ ID NO: 9) |
| TIMP2-R | Reverse: GGGGCCGTGTAGATAAACTCTAT (SEQ ID NO: 10) |
| TNFRSF11B-F | Forward: GCGCTCGTGTTTCTGGACA (SEQ ID NO: 11) |
| TNFRSF11B-R | Reverse: AGTATAGACACTCGTCACTGGTG (SEQ ID NO: 12) |
| IGF1-F | Forward: GCTCTTCAGTTCGTGTGTGGA (SEQ ID NO: 13) |
| IGF1-R | Reverse: GCCTCCTTAGATCACAGCTCC (SEQ ID NO: 14) |
| IGFBP2-F | Forward: GACAATGGCGATGACCACTCA (SEQ ID NO: 15) |
| IGFBP2-R | Reverse: CAGCTCCTTCATACCCGACTT (SEQ ID NO: 16) |
| TNFRSF10D-F | Forward: TACCACGACCAGAGACACC (SEQ ID NO: 17) |
| TNFRSF10D-R | Reverse: CACCCTGTTCTACACGTCCG (SEQ ID NO: 18) |
| TGFB3-F | Forward: ACTTGCACCACCTTGGACTTC (SEQ ID NO: 19) |
| TGFB3-R | Reverse: GGTCATCACCGTTGGCTCA (SEQ ID NO: 20) |
| LEP-F | Forward: TGCCTTCCAGAAACGTGATCC (SEQ ID NO: 21) |
| LEP-R | Reverse: CTCTGTGGAGTAGCCTGAAGC (SEQ ID NO: 22) |
| TNFSF14-F | Forward: ATACAAGAGCGAAGGTCTCACG (SEQ ID NO: 23) |
| TNFSF14-R | Reverse: CTGAGTCTCCCATAACAGCGG (SEQ ID NO: 24) |
| FGF6-F | Forward: TGGCTATTTGGTGGGGATCAA (SEQ ID NO: 25) |
| FGF6-R | Reverse: GAAGAGGGCACTTCTCACTCC (SEQ ID NO: 26) |
| TNF-α | Forward: CTTCTGCCTGCTG CACTTTGGA (SEQ ID NO: 27) |
| TNF-α | Reverse: TCCCAAAGTAGACCTGCCCAGA (SEQ ID NO: 28) |
| ADIPOQ-F | Forward: TGCTGGGAGCTGTTCTACTG (SEQ ID NO: 29) |
| ADIPOQ-R | Reverse: TACTCCGGTTTCACCGATGTC (SEQ ID NO: 30) |
| HPRT-F | Forward: CCTGGCGTCGTGATTAGTGAT (SEQ ID NO: 31) |
| HPRT-R | Reverse: AGACGTTCAGTCCTGTCCATAA (SEQ ID NO: 32) |

FIG. 24

| Start position | End position | Epitope sequences |
|---|---|---|
| 166 | 177 | PSRDPDQKGKRN (SEQ ID NO: 33) |
| 315 | 326 | YKALRRGGADTY (SEQ ID NO: 34) |
| 595 | 606 | ERDGASPSRIYT (SEQ ID NO: 35) |
| 619 | 630 | VHDDSRPALPST (SEQ ID NO: 36) |
| 960 | 971 | EGNTMRKTEAKA (SEQ ID NO: 37) |
| 1179 | 1190 | AISKETDAFQPH (SEQ ID NO: 38) |

FIG. 25C

| Number | Clone | Epitope sequences | Detection limit (ng) |
|---|---|---|---|
| 1 | 1/4J14-2 | PSRDPDQKGKRN (SEQ ID NO: 33) | 0.25 |
| 2 | 2/2F24-3 | YKALRRGGADTY (SEQ ID NO: 34) | 1.00 |
| 3 | 3/2C1 | ERDGASPSRIYT (SEQ ID NO: 35) | 0.01 |
| 4 | 3/3G1 | ERDGASPSRIYT (SEQ ID NO: 35) | 0.01 |
| 5 | 3/4J11 | ERDGASPSRIYT (SEQ ID NO: 35) | 0.25 |
| 6 | 4/1M3 | VHDDSRPALPST (SEQ ID NO: 36) | 0.25 |
| 7 | 4/2N2 | VHDDSRPALPST (SEQ ID NO: 36) | 0.05 |
| 8 | 4/3C14 | VHDDSRPALPST (SEQ ID NO: 36) | 0.25 |
| 9 | 5/3J6 | EGNTMRKTEAKA (SEQ ID NO: 37) | 5.00 |
| 10 | 5/3J9 | EGNTMRKTEAKA (SEQ ID NO: 37) | 5.00 |
| 11 | 6/2H18 | AISKETDAFQPH (SEQ ID NO: 38) | 0.01 |
| 12 | 6/2H3 | AISKETDAFQPH (SEQ ID NO: 38) | 0.05 |
| 13 | 6/3E3 | AISKETDAFQPH (SEQ ID NO: 38) | 1.00 |
| 14 | 6/4L11 | AISKETDAFQPH (SEQ ID NO: 38) | 0.25 |

FIG. 25D

Nidogen-1 (NID1) amino acid sequence (SEQ ID NO: 39)

Accession number: NP_002499.2

```
   1 mlasssrira awtralllpl llagpvgcls rqelfpfgpg qgdleledgd dfvspalels
  61 galrfydrsd idavyvttng iiatseppak eshpglfppt fgavapflad ldttdglgkv
 121 yyredlspsi tqraaecvhr gfpeisfqps savvvtwesv apyqgpsrdp dqkgkrntfq
 181 avlassdsss yaiflypedg lqfhttfskk ennqvpavva fsqgsvgflw ksngaynifa
 241 ndresvenla kssnsgqqgv wvfeigspat tngvvpadvi lgtedgaeyd dededydlat
 301 trlgledvgt tpfsykalrr ggadtysvps vlsprraate rplgpptert rsfqlavetf
 361 hqqhpqvidv deveetgvvf syntdsrqtc annrhqcsvh aecrdyatgf ccscvagytg
 421 ngrqcvaegs pqrvngkvkg rifvgssqvp ivfentdlhs yvvmnhgrsy taistipetv
 481 gysllplapv ggiigwmfav eqdgfkngfs itggeftrqa evtfvghpgn lvikqrfsgi
 541 dehghltidt elegrvpqip fgssvhiepy telyhystsv itssstreyt vteperdgas
 601 psriytyqwr qtitfqecvh ddsrpalpst qqlsvdsvfv lynqeekilr yalsnsigpv
 661 regspdalqn pcyigthgcd tnaacrpgpr tqftcecsig frgdgrtcyd idecseqpsv
 721 cgshticnnh pgtfrcecve gyqfsdegtc vavvdqrpin ycetglhncd ipqraqciyt
 781 ggssytcscl pgfsgdgqac qdvdecqpsr chpdafcynt pgsftcqckp gyqgdgfrcv
 841 pgevektrcq herehilgaa gatdpqrpip pglfvpecda hghyaptqch gstgycwcvd
 901 rdgrevegtr trpgmtppcl stvappihqg pavptavipl ppgthllfaq tgkierlple
 961 gntmrkteak aflhvpakvi iglafdcvdk mvywtditep sigraslhgg epttiirqdl
1021 gspegiavdh lgrnifwtds nldrievakl dgtqrrvlfe tdlvnprgiv tdsvrgnlyw
1081 tdwnrdnpki etsymdgtnr rilvqddlgl pngltfdafs sqlcwvdagt nraeclnpsq
1141 psrrkalegl qypfavtsyg knlyftdwkm nsvvaldlai sketdafqph kqtrlygitt
1201 alsqcpqghn ycsvnnggct hlclatpgsr tcrcpdntlg vdcieqk
```

FIG. 30

Nidogen-1 (NID1) nucleotide sequence (SEQ ID NO:40)
Accession number: NM_002508.3

```
   1 agttcgggaa catgttggcc tcgagcagcc ggatccgggc tgcgtggacg cgggcgctgc
  61 tgctgccgct gctgctggcg gggcctgtgg gctgcctgag ccgccaggag ctctttccct
 121 tcggccccgg acaggggggac ctggagctgg aggacgggga tgacttcgtc tctcctgccc
 181 tggagctgag tggggcgctc cgcttctacg acagatccga catcgacgca gtctacgtca
 241 ccacaaatgg catcattgct acgagtgaac ccccggccaa agaatcccat cccgggctct
 301 tcccaccaac attcggtgca gtcgcccctt tcctggcgga cttggacacg accgatggcc
 361 tggggaaggt ttattatcga gaagacttat ccccctccat cactcagcga gcagcagagt
 421 gtgtccacag aggggttccccg gagatctctt ccagcctag tagcgcggtg gttgtcactt
 481 gggaatccgt ggcccccctac caagggccca gcagggaccc agaccagaaa ggcaagagaa
 541 acacgttcca ggctgttcta gcctcctctg attccagctc ctatgccatt ttcctttatc
 601 ctgaggatgg tctgcagttc catacgacat tctcaaagaa ggaaaacaac caagttcctg
 661 ccgtggttgc attcagtcaa ggttcagtgg gattcttatg gaagagcaac ggagcttata
 721 acatatttgc taatgacagg gaatcagttg aaaatttggc caagagtagt aactctgggc
 781 agcagggtgt ctgggtgttt gagattggga gtccagccac caccaatggc gtggtgcctg
 841 cagacgtgat cctcggaact gaagatgggg cagagtatga tgatgaggat gaagattatg
 901 acctggcgac cactcgtctg ggcctggagg atgtgggcac cacgcccttc tcctacaagg
 961 ctctgagaag gggaggtgct gacacataca gtgtgcccag cgtcctctcc ccgcgccggg
1021 cagctaccga aaggccccctt ggacctccca cagagagaac caggtctttc cagttggcag
1081 tggagacttt tcaccagcag caccctcagg tcatagatgt ggatgaagtt gaggaaacag
1141 gagttgttt cagctataac acggattccc gccagacgtg tgctaacaac agacaccagt
1201 gctcggtgca cgcagagtgc agggactacg ccacgggctt ctgctgcagc tgtgtcgctg
1261 gctatacggg caatggcagg caatgtgttg cagaaggttc cccccagcga gtcaatggca
1321 aggtgaaagg aaggatcttt gtggggagca gccaggtccc cattgtcttt gagaacactg
1381 acctccactc ttacgtagta atgaaccacg ggcgctccta cacagccatc agcaccattc
1441 ccgagaccgt tggatattct ctgcttccac tggccccagt tggaggcatc attggatgga
1501 tgtttgcagt ggagcaggac ggattcaaga atggggttcag catcaccggg ggtgagttca
1561 ctcgccaggc tgaggtgacc ttcgtggggc acccgggcaa tctggtcatt aagcagcggt
1621 tcagcggcat cgatgagcat gggcacctga ccatcgacac ggagctggag gccgcgtgc
1681 cgcagattcc gttcggctcc tccgtgcaca ttgagcccta cggagctg taccactact
1741 ccacctcagt gatcacttcc tcctccaccc gggagtacac ggtgactgag cccgagcgag
1801 atggggcatc tccttcacgc atctacactt accagtggcg ccagaccatc accttccagg
1861 aatgcgtcca cgatgactcc cggccagccc tgcccagcac ccagcagctc tcggtggaca
1921 gcgtgttcgt cctgtacaac aggaggaga agatcttgcg ctatgctctc agcaactcca
1981 ttgggcctgt gagggaaggc tcccctgatg ctcttcagaa tccctgctac atcggcactc
2041 atgggtgtga caccaacgcg gcctgtcgcc ctggtcccag gacacagttc acctgcgagt
2101 gctccatcgg cttccgagga gacgggcgaa cctgctatga tattgatgaa tgttcagaac
2161 aaccctcagt gtgtgggagc cacacaatct gcaataatca cccaggaacc ttccgctgcg
2221 agtgtgtgga gggctaccag ttttcagatg agggaacgtg tgtggctgtc gtggaccagc
2281 gccccatcaa ctactgtgaa actggccttc ataactgcga cataccccag cgggcccagt
2341 gtatctacac aggaggctcc tcctacacct gttcctgctt gccaggcttt tctggggatg
2401 gccaagcctg caagatgta gatgaatgcc agccaagccg atgtcaccct gacgccttct
2461 gctacaacac tccaggctct ttcacgtgcc agtgcaaacc tggttatcag ggagacggct
2521 tccgttgcgt gcccggagag gtggagaaaa cccggtgcca gcacgagcga gaacacattc
2581 tcggggcagc gggggcgaca gacccacagc gacccattcc tccggggctg ttcgttcctg
2641 agtgcgatgc gcacgggcac tacgcgccca cccagtgcca cggcagcacc ggctactgct
2701 ggtgcgtgga tcgcgacggc cgcgaggtgg agggcaccag gaccaggccc gggatgacgc
2761 ccccgtgtct gagtacagtg gctcccccga ttcaccaagg acctgcggtg cctaccgccg
2821 tgatcccctt gcctcctggg acccatttac tctttgccca gactggaag attgagcgcc
2881 tgccccctgga gggaaatacc atgaggaaga cagaagcaaa ggcgttcctt catgtcccgg
2941 ctaaagtcat cattggactg gcctttgact gcgtggacaa gatggttac tggacggaca
3001 tcactgagcc ttccattggg agagctagtc tacatggtgg agagccaacc accatcatta
3061 gacaagatct tggaagtcca gaaggtatcg ctgttgatca ccttggccgc aacatcttct
3121 ggacagactc taacctggat cgaatagaag tggcgaagct ggacggcacg cagcgccggg
```

FIG. 31A

```
3181 tgctctttga gactgacttg gtgaatccca gaggcattgt aacggattcc gtgagaggga
3241 acctttactg gacagactgg aacagagata accccaagat tgaaacttcc tacatggacg
3301 gcacgaaccg gaggatcctt gtgcaggatg acctgggctt gcccaatgga ctgaccttcg
3361 atgcgttctc atctcagctc tgctgggtgg atgcaggcac caatcgggcg gaatgcctga
3421 accccagtca gcccagcaga cgcaaggctc tcgaagggct ccagtatcct tttgctgtga
3481 cgagctacgg gaagaatctg tatttcacag actggaagat gaattccgtg gttgctctcg
3541 atcttgcaat tccaaggag acggatgctt ccaaccccca caagcagacc cggctgtatg
3601 gcatcaccac ggccctgtct cagtgtccgc aaggccataa ctactgctca gtgaacaatg
3661 gcggctgcac ccacctatgc ttggccaccc cagggagcag gacctgccgt tgccctgaca
3721 acaccttggg agttgactgt atcgaacaga aatgaagaca agagtgcctt atttcctttc
3781 caagtatttc acagcaacac tctacttgaa gcaacttggt ccagattgaa aagtgtcctc
3841 tggctgagtg gccactaggc ccagacccag cccagcctga gccccaacaa cttttccctc
3901 actgttcccc aaaacatgca ccctggactt ctctaataga aaagtctcca cccctacaca
3961 aggacagaac cctccacccc tacccccaac cctcagacag acttatacac ccctgagtga
4021 ggattacatg cccatcccag tgtcctagga ccttttccca atactagccc cccagtggtg
4081 aacagaacct cccaaatttg agttgcaccc ttccctgtgg ccttatgagc tcagcctcgc
4141 tttgaggtac ccaccgtcct gtcagctcct tgacctatga gccggggcct gactaggaaa
4201 agttgggagt taaggaggaa attagcattc cttaatgttt tgttttggtg ctctgaattt
4261 cttctttatt atagtcctat agttttactc ctcagttcct caccatcatc atcttgtcta
4321 agaccccat tataatattc atgcgctgct ttttcatcaa aacctaccct gtcctagaga
4381 tctatgggca tttggtggat gataatgagc agcccctccc agatagaatg tcaatatttg
4441 agcagtagga tattggcatt tgttagttaa aggcttaaat caaaagaatg tccaatggta
4501 ggaatttcaa ggtgtaggtc agatatttga gaataggggga ttttttttgat gtgccttaaa
4561 ttataccaaa gattactaat tattcctctt tgcccaaaat acttgcatcc aaggttctag
4621 tctctgttgc tgtgctggtc tttagcccca ctgcttgcac tgatgtccct cctttcacg
4681 gagacctatc tgaggtacag gatggggctg gcaccagatg atgtcccacc acagtccctc
4741 acctccggcc tccacatgac agaaccaatt tacactcaac catgacctca cccctccttg
4801 gtttctccct cgatctgtgg ccctttttgg atgtattctt atctaacaac acaatccgga
4861 aagactgaat tgaatattta tactaatggt tcatatcctt tattgctcaa tgatctaatt
4921 aaagggatca ttgccacatt tcatgtttat atttctacaa tttgtttaga aaacatctcc
4981 tgaccatatc agtagctcgt gttatctttt tatcaactgc ttcccagagt cctaaaacaa
5041 tagaaatttt ggattgaaaa gttcagcata aggagtttga gtcagtaaag gatgggataa
5101 aggagtcgag atgattcaat gaaagtatc acaaaaaga gattgatcaa caagagaaat
5161 aaaaagccc aagaggaagt ggtaggggaa ggaatttaag aacagcaata agtaaaactc
5221 ttaagtaact ccaaaaagaa aatggtacat tttgccaaag accacttata cttgagaaca
5281 tggaagaatt tgcctgatac tctctttggg gaaaagagtc tctcctcttt tcctcaaacc
5341 ccagtacact cagcctctct gccccacctt ctcctgactt tgtcctcact tgcttctgca
5401 gtacattgga acctgaattg aaagaaagtc ttccttgaat aattggagtt tgtcttgaga
5461 ggcaaatata gccccaagaa tcacaagatt cgaggaccat gtaggtcttt tacgtagccc
5521 aaatccataa attagtctca cttttgtat ttatcgtttc atattaaacc ctctatatca
5581 aatgttcatc atgattttgt atgatttta taactatttt attcatttta ttagatttat
5641 tctaaaattt tttaatggta aattcttaaa ctgtggaaac cactgaaggt gcttattaac
5701 tgttctccca gatttgtaca agtattggat gattccttga gtttacagct gtacaaatag
5761 tgtggaaaat aaactttttt taaaaagaa aa
```

FIG. 31B

NIDOGEN 1 AS A DIAGNOSTIC MARKER AND THERAPEUTIC TARGET OF HEPATOCELLULAR CARCINOMA, COMPOSITION AND METHODS THEREOF The present application claims priority to U.S. provisional application Ser. No. 63/014,179 filed Apr. 23, 2020 which is incorporated by reference in its entirety.

SEQUENCE LISTING

The present application contains a Sequence Listing which has been submitted electronically in ASCII format and is hereby incorporated by reference in its entirety. Said ASCII copy, created on Jul. 14, 2021, is named 10030_008633-US1 and is 25.6 KB in size.

1. FIELD

The present disclosure provides methods and compositions for treatment, screening, diagnosis and prognosis of hepatocellular carcinoma with extrahepatic metastasis. Provided herein are methods and compositions for treatment, screening, diagnosis and prognosis of metastatic cancers. Also provided are antibodies and compositions for the treatment of cancers. Provided herein is therapeutic target for the treatment of cancers or as a marker for cancers. In particular, the protein represents a biological target against which affinity molecules including therapeutic antibodies, or other pharmaceutical agents, can be made. The disclosure also relates to the use of such affinity molecules for the treatment and/or diagnosis of cancers.

2. BACKGROUND

Intercommunication between tumor cells and their microenvironment plays a crucial role during cancer development and metastasis.[1] Extracellular vesicle (EV) shedding has emerged as an important channel for intercellular communication. The distinct functional properties of EVs are determined by the composition of lipids, proteins and RNAs present within the EVs, thus resulting in EVs with numerous potential functions.[2]

Long-range signaling between local tumor cells and distant cells can be mediated by the transport of functional oncogenes through tumor-derived exosomes, which subsequently influences the signaling and behavior of the recipient cells.[3, 4] Evidence in different cancer models has revealed the role of tumor-derived exosomes in generating a pre-metastatic niche that favors the survival of disseminated tumor cells in distant organs. EVs released by chronic lymphocytic leukemia cells induce the phenotype of cancer-associated fibroblasts in stromal cells, which contributes to a tumor-supportive microenvironment.[5] Another study showed that EVs derived from pancreatic ductal adenocarcinoma initiate pre-metastatic niche formation and consequently increase liver metastatic burden in naïve mice.[6] EVs from highly metastatic melanomas are able to educate bone marrow progenitors through the upregulation of Met and induce vascular leakiness at pre-metastatic sites.[7] These studies highlight the multifaceted roles of tumor-derived EVs in the modulation of the tissue microenvironment to facilitate metastasis.

The tumor microenvironment is influenced by numerous stromal factors that coordinate to provide a nourishing condition for cancer cells to survive and grow. Cancer-associated fibroblasts (CAFs) are one of the most prominent stromal components in the tumor microenvironment. Compelling evidence has documented the activity of CAFs in enhancing tumor formation and metastasis in different ways. CAFs have been shown to recruit proinflammatory immune cells and enhance angiogenesis in tumors.[8] CAFs are pivotal players that contribute to an immunosuppressive tumor microenvironment.[9, 10] Cancer stem cells are capable of mediating cancer metastasis and drug resistance. Conditioned medium from CAF cultures has been shown to activate cancer stemness properties of cancer cells via paracrine secretion of hepatocyte growth factor.[11] It has been shown that blocking the communication between cancer cells and CAFs significantly diminishes HCC growth and dissemination.[12] As a robust marker of activated fibroblasts, α-SMA in the stroma of multiple solid tumors identifies patients with poor survival.[13] In HCC, α-SMA is present in the majority of metastatic lesions.[14] HCC cases with high α-SMA staining in the peritumoral region had a significantly worse prognosis than do HCC cases with low peritumoral α-SMA signal.[15]

Hepatocellular carcinoma (HCC) accounts for most liver cancers and is currently the third leading cause of cancer-related death worldwide. Metastasis is a key event at the advanced stage of hepatocarcinogenesis. Approximately half of the patients with extrahepatic HCC present with metastasis in the lung, the most frequent site of extrahepatic HCC.[16] However, it remains unclear how the microenvironment in the lungs favors incoming metastatic cells. Therefore, we endeavored to determine how HCC-derived EVs activate pulmonary fibroblasts to cultivate a supportive microenvironment for disseminated metastatic cells to colonize the lungs.

3. SUMMARY

The present disclosure provides methods and compositions for treatment, screening, diagnosis and prognosis of hepatocellular carcinoma with extrahepatic metastasis. Provided herein are methods and compositions for treatment, screening, diagnosis and prognosis of metastatic cancers such as lung cancer, breast cancer, oral cavity squamous cell carcinomas, ovarian cancer, colorectal cancer or pancreatic cancer. Also provided are antibodies and compositions for treatment of cancers.

The present disclosure shows the detection of nidogen 1 (NID1) in metastatic HCC cell-derived extracellular vesicles (EVs) promoted pre-metastatic niche formation in the lung by enhancing angiogenesis and pulmonary endothelial permeability to facilitate colonization of tumor cells and extrahepatic metastasis.

The differential expression of NID1 in various stages of HCC and other cancers permits the protein to be targeted using affinity molecule, e.g. antibody, based therapies for such cancers. Thus, NID1 can be used in the generation of affinity molecules, including antibodies, that bind specifically to epitopes of NID1, and can be targeted by such affinity molecules as the basis of treatment. Affinity molecules, including antibodies, that target a protein on the cell surface of cancer cells or extracellular vesicles (EVs) may be employed in the treatment of cancer through a variety of mechanisms, including (i) lysis by complement mediated or antibody-dependent cellular cytotoxicity (ADCC), (ii) lysis by drugs or toxin(s) conjugated to such affinity molecules or (iii) inhibition of the physiological function of such protein, which may be driving growth of cancer cells, e.g. through signaling pathways. An important aspect of such affinity molecule-based treatment is that the normal expression profile of the protein target, in terms of tissue distribution and expression level, is such that any targeting of the protein target on normal tissues by the antibody does not give rise to adverse side-effects through binding to normal tissues.

The disclosure provides a method for the treatment or prophylaxis of cancer wherein NID1 is expressed in said cancer or EVs, which comprises administering to a subject in need thereof a therapeutically effective amount of an affinity molecule which binds to NID1.

The affinity molecules may be an antibody, e.g. a whole antibody, or a functional fragment thereof or an antibody mimetic. In one embodiment, affinity molecules included antibodies for example monoclonal antibodies. The affinity molecule may be a chimeric antibody, a human antibody, a humanized antibody, a single chain antibody, a defucosylated antibody or a bispecific antibody. Functional antibody fragments include is a UniBody, a domain antibody or a Nanobody.

The affinity molecules for use in the disclosure may contain or be conjugated to a therapeutic moiety, such as a cytotoxic moiety or a radioactive isotope. The affinity molecule may be an antibody drug conjugate or immunoconjugate.

The affinity molecules may elicit antibody-dependent cellular cytotoxicity (ADCC) or may elicit complement dependent cytotoxicity (CDC). The affinity molecule may induce apoptosis of cancer cells, kill or reduce the number of cancer stem cells and/or kill or reduce the number of circulating cancer cells. Affinity molecules may modulate a physiological function of NID1, inhibit ligand binding to NID1 and/or inhibit a signal transduction pathway mediated by NID1.

The disclosure also provides a method of detecting, diagnosing and/or screening for or monitoring the progression of a cancer wherein NID1 is expressed in said cancer, or of monitoring the effect of a cancer drug or therapy wherein NID1 is expressed in said cancer, in a subject which comprises detecting the presence or level of NID1, or one or more fragments thereof, or the presence or level of nucleic acid encoding NID1 or which comprises detecting a change in the level thereof in said subject.

Such a method may comprise detecting the presence of NID1, or one or more fragments thereof, or the presence of nucleic acid encoding NID1, in which either (a) the presence of an elevated level of NID1 or said one or more fragments thereof or an elevated level of nucleic acid encoding NID1 in the subject as compared with the level in a healthy subject, or (b) the presence of a detectable level of NID1 or said one or more fragments thereof or a detectable level of nucleic acid encoding NID1 in the subject as compared with a corresponding undetectable level in a healthy subject is indicative of the presence of the cancer wherein NID1 is expressed in said cancer, in said subject.

The disclosure also provides a method of detecting, diagnosing and/or screening for or monitoring the progression a cancer wherein NID1 is expressed in said cancer, or of monitoring the effect of a cancer drug or therapy wherein NID1 is expressed in said cancer, in a subject which comprises detecting the presence or level of antibodies capable of immunospecific binding to NID1, or one or more fragments thereof.

In the methods according to the disclosure, the presence of NID1, or one or more fragments thereof, or the presence of nucleic acid encoding NID1, or the presence or level of antibodies capable of immunospecific binding to NID1, or one or more fragments thereof, may be detected by analysis of a biological sample obtained from the subject.

The presence of NID1, or one or more fragments thereof, may be detected using an affinity molecule which binds to NID1. The affinity molecule may be any suitable affinity molecule as mentioned herein. The affinity molecule may contain or be conjugated to a detectable label.

In any of the aspects of the disclosure referred to herein, the subject is a human, canine, feline, or non-human primate.

In one embodiment, provided herein is a method of diagnosing hepatocellular carcinoma (HCC) in a subject comprising: (i) collecting a sample from the subject; (ii) centrifuging the sample at 1500×g for 30 mins to obtain serum; (iii) centrifuging the serum in step (ii) at 16,500×g for 45 mins to obtain large vesicles; (iv) purifying EV from large vesicles; (v) lysing EV to release protein from the EV; and (vi) measuring NID1 level over EV protein level (µg/µg)(w/w), wherein an increased level of NID1 in extracellular vesicles (EVs) as compared to a control subject without HCC indicates an increased risk of HCC in the subject, wherein the HCC comprises extrahepatic metastasis, and wherein the EVs promoted pre-metastatic niche formation in the lung by enhancing angiogenesis and pulmonary endothelial permeability to facilitate colonization of tumor cells and extrahepatic metastasis.

In one embodiment, enzyme-Linked Immunosorbent Assay (ELISA) was used to determine NID1 expression in EVs extracted from sera of patients. The isolated EVs were lyzed and the proteins were subjected to the measurement of NID1. The level of EV-NID1 was expressed as amount of NID1 over EV protein amount (µg/µg) (w/w). ELISA was also used to measure level of TNFR1 in sera of patients. TNFR1 level was expressed as TNFR1 amount per serum volume (µg/ml).

In certain embodiments, there is overlapping of the detection range between diseased state versus control subjects. The ranges of EV-NID1 and serum TNFR1 of control subjects are 0.0005-0.0032 µg/µg and 4.65-10.26 µg/ml, respectively. Thus, expression levels of EV-NID1 and serum TNFR1 higher than 0.0032 µg/µg and 10.26 µg/ml, respectively, indicate diseased state.

In one embodiment, the method further comprises a step of measuring tumor necrosis factor receptor 1 ("TNFR1") and Alpha-Fetoprotein ("AFP") levels, wherein an increased TNFR1 and AFP levels per serum volume (ng/ml) as compared to a control subject without HCC indicates an increased risk of HCC in the subject.

Provided herein is a method of diagnosis or monitoring the progression of hepatocellular carcinoma (HCC) in a subject comprising:
(i) collecting a sample from the subject;
(ii) centrifuging the sample to obtain serum;
(iii) isolating extracellular vesicles from the serum, optionally the extracellular vesicles are isolated via centrifugation and/or purification;
(iv) lysing extracellular vesicles to release proteins from the extracellular vesicles to form a lysed mixture; and
(vi) measuring an amount of NID1 in the lysed mixture, wherein an increased level of NID1 in extracellular vesicles as compared to a control subject without HCC indicates an increased risk of HCC in the subject.

In one embodiment, provided is a method of diagnosing or monitoring the progression of hepatocellular carcinoma (HCC) in a subject comprising:
(i) collecting a sample from the subject;
(ii) centrifuging the sample to obtain serum;

(iii) isolating extracellular vesicles ("EV") from the serum, optionally the extracellular vesicles are isolated via centrifugation and/or purification;
(iv) lysing extracellular vesicles to release proteins from the extracellular vesicles to form a lysed mixture;
(v) measuring an amount of NID1 in the lysed mixture;
(vi) comparing the measured amount of NID1 in the lysed mixture to an amount of NID1 reflective of levels of NID1 in control subjects without HCC; and
(vii) diagnosing the subject with an increased risk of HCC if the measured amount of NID1 in the lysed mixture exceeds the amount of NID1 reflective of control subjects without HCC.

In one embodiment, the method further comprising the steps of: measuring tumor necrosis factor receptor 1 ("TNFR1") levels per serum volume (ng/ml) and optionally, alpha-fetoprotein ("AFP") levels per serum volume (ng/ml); and comparing the measured amount of TNFR1 per serum volume and optionally the AFP levels per serum volume to a threshold amount of TNFR1 per serum volume and optionally a threshold amount of AFP per serum volume in control subjects without HCC, wherein an elevated amount of TNFR1 and optionally, AFP levels per serum volume as compared to the threshold amount of TNFR1 and optionally the amount of AFP in the control subjects without HCC indicates an increased risk of HCC in the subject.

In one embodiment, the HCC has metastasized to the lungs.

Provided herein is a method of diagnosing hepatocellular carcinoma (HCC) in a subject comprising: (i) collecting a sample from the subject; (ii) centrifuging the sample at 1500×g for 30 mins to obtain serum; (iii) centrifuging the serum in step (ii) at 16,500×g for 45 mins to obtain large vesicles; (iv) purifying EV from large vesicles; (v) lysing EV to release protein from the EV; and (vi) measuring NID1 level over EV protein level (μg/μg)(w/w), wherein an increased level of NID1 in extracellular vesicles (EVs) as compared to a control subject without HCC indicates an increased risk of HCC in the subject, wherein the HCC comprises extrahepatic metastasis, and wherein the EVs promoted pre-metastatic niche formation in the lung by enhancing angiogenesis and pulmonary endothelial permeability to facilitate colonization of tumor cells and extrahepatic metastasis.

In one embodiment, the method further comprising a step of measuring tumor necrosis factor receptor 1 ("TNFR1") and optionally, Alpha-Fetoprotein ("AFP") levels per serum volume (ng/ml), wherein an increased TNFR1 and optionally, AFP levels per serum volume as compared to a control subject without HCC indicates an increased risk of HCC in the subject.

In one embodiment, the HCC has metastasized to the lungs.
In one embodiment, the sample is blood or other body fluids.
In one embodiment, the NID1 is localized on the surface of EVs.
In one embodiment, the NID1 is a protein having an amino acid sequence comprising SEQ ID NO: 39 (i.e. NID1) or a derivative thereof, or wherein the NID1 is a nucleic acid sequence of SEQ ID NO: 40 or a derivative thereof.
In one embodiment, the NID1 is measured by Enzyme-Linked Immunosorbent Assay ("ELISA") using a monoclonal antibody produced by hybridoma cell line 34858-1-4/2N2 which is deposited with American Type Culture Collection, Patent Depository—PO083151 10801 University Boulevard, Manassas, Virginia 20110, U.S.A. under the Budapest treaty.

In one embodiment, the amount of NID1 reflective of control subject is 0.0005-0.0032 μg/μg and the measured level of NID1 in the subject with an increased risk of HCC is higher than 0.0032 μg/μg.
In one embodiment, the threshold amount of TNFR1 in control subject is 4.65-10.26 μg/ml and the measured amount of TNFR1 in the subject with an increased risk of HCC is higher than 10.26 μg/ml.
In one embodiment, the threshold amount of AFP in control subjects is 5.7-226.0 ng/ml. In one embodiment, the average threshold amount of AFP in control subject is 102.0 +/− 64.5 ng/ml.
In one embodiment, the measured amount of AFP in early-stage HCC patients is 1.95-1177.4 ng/ml. In one embodiment, the average measured amount of AFP in early-stage HCC patients is 454.1 +/−264.9 ng/ml.
In one embodiment, the measured amount of AFP in late-stage HCC patients is 203.5-1483.3 ng/ml. In one embodiment, the average measured amount of AFP in late-stage HCC patients is 1140.5 +/−267.2 ng/ml.

Provided herein is a method of treating cancer in a subject in need thereof comprising administering an effective dose of anti-nidogen 1 (NID1) monoclonal antibody to the subject. In one embodiment, the method further comprising administering an effective dose of anti-TNFR1 antibody.

In one embodiment, the cancer is HCC that is extrahepatic metastatic cancer.
In one embodiment, the NID1 monoclonal antibody is derived from metastatic HCC cells or sera of HCC late-stage patient.
In one embodiment, the NID1 monoclonal antibody is derived from ascites no. 1 to 14 anti-NID1 antibodies.
In one embodiment, the extraheptic metastatic cancer is breast cancer, oral cavity squamous cell carcinoma, ovarian cancer or colorectal cancer.
In one embodiment, the NID1 monoclonal antibody: (i) suppresses the effect of HCC in EVs; (ii) decreases HCC cell growth; (iii) decreases HCC motility; (iv) reduces HCC colonization of cells; (v) decreases pre-metastatic niche formation; (vi) decreases angiogenesis; (vii) decreases pulmonary endothelial permeability; (viii) reduces extrahepatic metastasis, or a combination thereof.

Provided herein is a NID1 monoclonal antibody and fragments thereof that are derived from ascites no. 1-14 anti-NID1 antibodies that specifically binds the respective NID1 epitope.
In one embodiment, the NID1 monoclonal antibody specifically binds to an epitope comprising the amino acid sequence VHDDSRPALPST (SEQ ID NO: 36).
Provided herein is a NID1 monoclonal antibody produced by hybridoma cell line 34858-1-4/2N2. In one embodiment, the monoclonal antibody is NID1 neutralizing antibody. Provided herein is a composition comprising NID1 monoclonal antibody and a pharmaceutical acceptable carrier.
Provided herein is a kit for the diagnosis of HCC comprising in separate containers NID1 monoclonal antibody and fragments thereof and a reagent for detecting NID1 monoclonal antibody binding to NID1.
In one embodiment, the kit further comprising in separate containers TNFR1 monoclonal antibodies and a reagent for detecting TNFR1 monoclonal antibody binding to TNFR1.
In one embodiment, the NID1 monoclonal antibody produced by hybridoma cell line 34858-1-4/2N2.
Provided herein is a hybridoma cell line 34858-1-4/2N2.

4. BRIEF DESCRIPTION OF THE DRAWINGS

The patent or application file contains at least one drawing executed in color. Copies of this patent or patent application with color drawngs will be provided by the Office upon request and payment of the necessary file.

FIGS. 1A-1E EVs from metastatic MHCC97L cells promote HCC tumorigenesis and metastasis. (A) Migration and invasion assays of LO2 and PLC/PRF/5 cells pretreated with EVs derived from MIHA, MHCC97L or MHCCLM3 cells. Cells treated with PBS were included as controls. Representative images of fixed and crystal violet-stained migrated and invaded cells at the end of the experiment are shown. (B) Schematic diagram of the EV education mouse model. Nude mice were injected with EVs derived from MIHA or MHCC97L cells via tail vein once a week for 3 weeks (15 µg per week) prior to orthotopic liver implantation of tumor seeds derived from naïve luciferase-labeled MHCC97L cells (n=5). Analysis of liver tumors formed and distant lung metastases was performed 5 weeks after liver implantation. (C) Bioluminescence imaging of animals at the end of the experiment. (D) Image of excised livers. Measurement of liver tumor size is plotted. (E) Bioluminescence imaging of dissected lung tissues. Quantification of the luciferase signal is shown. Three independent experiments were performed in triplicate for assays shown in A-B. Data are represented as the mean±SEM; *$P<0.05$; $P<0.01$; *$P<0.001$; NS, not significant from Student's t-test.

FIGS. 2A-2H EVs from metastatic MHCC97L cells enhance endothelial leakiness and hepatoblasts colonization in the lungs. (A) Tissue distribution of EVs in tissues of mice. Twenty-four hours after mice were intravenously injected with EVs derived from MHCC97L CD63-GFP cells, the mice were subjected to euthanasia, perfused and fixed for 24 hours before tissue dissection. Tissue sections were examined under confocal microscopy. Black and white images reveal the detection of EVs in different tissues (Upper panel). EVs are indicated by the arrowhead. Images of GFP$^+$ EVs and DAPI-stained nuclei are shown (Lower panel). Quantification of the signal in 5 random fields of 3 tissue sections per organ is shown. Scale bar: 10 µm. (B) Tube formation assay of HUVECs pretreated with the indicated EVs. Quantification of capillary-like tubular structures formed is shown. (C) Analysis of lung vessel leakiness after tail vein injection of MHCC97L-EVs, Texas Red-Dextran and FITC-Lectin. The arrowhead indicates the area of endothelial leakiness. Scale bar: 20 µm. (D) Analysis of lung colonization of murine p53−/−; Myc hepatoblasts ($1\times10^5$) 2 weeks after coinjection with the indicated EVs (10 µg) via tail vein (n=5). (E) Image of bioluminescence signals of mice at the end of the experiment. Quantification of the luciferase signal is shown. (F) Bioluminescence imaging of dissected lung tissues and quantification of the luciferase signal. (G) Representative image of a dissected lung after fixation. (H) Representative images of H&E staining of lung tissues. Examples of metastatic lesions are indicated by arrowheads. Insets show the enlarged area of the metastatic lesions. Magnification, 5×; Scale bar, 200 µm. Three independent experiments were performed in triplicate for assays shown in A-C. Data are represented as the means±SEM; *$P<0.05$; $P<0.01$; *$P<0.001$; ****$P<0.0001$; NS, not significant from Student's t-test.

FIGS. 3A-3G NID1 level in EVs correlates with the metastatic potential of cells and tumor burden in mice. (A) Protein was extracted from EVs derived from MIHA, MHCCLM3 and MHCC97L cells and was subjected to mass spectrometry analysis (technical triplicate/sample). Venn diagram illustrating the number of proteins that were commonly and uniquely expressed in EVs of the indicated cell lines. (B) Analysis of the distribution of cellular components of proteins commonly identified in MHCCLM3- and MHCC97L-EVs using FunRich3.1.3. (C) Volcano plots of proteins that were significantly modulated by at least 4-fold in MHCCLM3-EVs (left) and MHCC97L-EVs (right) when compared to proteins of MIHA-EVs with P-value<0.05. (D) Top 10 upregulated proteins identified in MHCCLM3-EVs ranked by P-value. Significance of their upregulation in MHCC97L-EVs is listed accordingly. (E) Immunoblots showing NID1 expression in the total cell lysate (TCL) and EVs of MIHA, MHCCLM3 and MHCC97L cells. (F) Analysis of NID1 expression in EVs derived from MIHA cells and different HCC cell lines was performed in duplicate by ELISA. (G) Collection of blood from mice before and after orthotopic liver implantation of luciferase-labeled MHCC97L tumor seed (n=5). EVs were isolated from the serum and subjected to protein extraction. Serum EV-NID1 level was analyzed in duplicate using ELISA. Data are represented as the mean±SEM; *$P<0.05$; $P<0.01$; *$P<0.001$ from Student's t-test.

FIGS. 4A-4G EV-NID1 is a functional component that drives HCC motility, tumorigenesis and metastasis. (A) ELISA analysis of NID1 levels in EVs derived from MHCC97L (97L) control (CTL-KD) and NID1 knockdown cells (NID1-KD1 and NID1-KD2) and control (XPack) and NID1 overexpressing cells (XP-NID1) established in HLE and Hep3B cells. The analysis was performed in triplicates. (B) Examination of the migratory potential and invasiveness of MIHA and PLC/PRF/5 cells pretreated with MHCC97L CTL-KD- and NID1-KD-EVs. (C) Examination of the migratory potential and invasiveness of MIHA and PLC/PRF/5 cells pretreated with HLE XPack- and XP-NID1-EVs. (D) Examination of the migratory potential and invasiveness of MIHA and PLC/PRF/5 cells pretreated with Hep3B XPack- and XP-NID1-EVs. (E) EV mouse model comparing the effects of EVs from MHCC97L CTL-KD and NID1-KD cells on HCC tumorigenesis and metastasis (n=5). Image showing the luciferase signal of the animals at the end of the experiment. Quantification of the luciferase signal is shown. (F) Bioluminescence imaging of dissected liver tissues. Quantification of the luciferase signal is shown. (G) Bioluminescence imaging of dissected lung tissues. Quantification of the luciferase signal is shown. Three independent experiments were performed in triplicate for assays shown in C-D. Data are represented as the mean±SEM; *$P<0.05$; $P<0.01$; *$P<0.001$; NS, not significant from Student's t-test.

FIGS. 5A-5G EVs with reduced NID1 levels show a diminished ability to increase vascular permeability, enhance angiogenesis and facilitate colonization of hepatoblasts in the lung. (A) Analysis of lung vessel leakiness after tail vein injection of PBS, MHCC97L CTL-KD-EVs or NID1-KD-EVs; Texas Red-Dextran and FITC-Lectin. The arrowhead indicates the area of endothelial leakiness. Scale bar: 20 µm. (B) Tube formation of HUVECs pretreated with EVs. Quantification of the capillary-like tubular structures formed is shown. Three independent experiments were performed in triplicate. (C) In vivo angiogenesis plug formation assay performed by subcutaneous coinjection of PLC/PRF/5 cells with PBS, MHCC97L CTL-KD-EVs or NID1-KD-EVs. Representative images showing H&E staining and immunohistochemistry of dissected tumors using anti-CD31 antibody are shown. The inset shows the enlarged area of the tumors. Scale bar: 100 µm. The number of microvessels is counted. (D) Analysis of lung colonization of murine p53−/−; Myc hepatoblasts (1×10⁵) after coinjection with EVs (10 µg) via tail vein (n=4). Bioluminescence imaging of mice at the end of the experiment. Quantification of the luciferase signal is shown. (E) Bioluminescence imaging of dissected lung tissues. Quantification of the luciferase signal is shown. (F) Representative image of dissected lung after fixation. (G) Representative images of H&E staining of lung tissues. Examples of metastatic lesions are indicated by arrowheads. Insets show the enlarged area of the metastatic lesions. Magnification, 2.5×; Scale bar, 500 µm. Data are represented as the mean±SEM; *P<0.05; P<0.01; *P<0.001; NS, not significant from Student's t-test.

FIGS. 6A-6J TNFR1 secreted by EV-NID1-activated pulmonary fibroblasts promotes HCC cell motility and colonization in the lungs. (A) Immunohistochemistry of metastatic lesions in lungs tissues obtained from mice injected with PBS, MHCC97L CTL-KD-EVs of NID1-KD-EVs using anti-α-SMA antibody. Magnification, 20×; Scale bar, 25 µ. (B) Immunoblotting of S100A4 expression in MRC-5 cells treated with EVs for 24 hr. (C) Immunofluorescence in MRC-5 cells after a 24-hr incubation with PKH67-labeled MHCC97L-EVs. Scale bar: 20 µm. (D) Analysis of TNFR1 copy number and concentration of soluble TNFR1 in MRC-5 cells pretreated with the indicated EVs using qPCR and ELISA, respectively. (E) Diagram illustrating the collection of conditioned medium from MRC-5 cells pretreated with EVs for functional assays. (F) Colony formation assay performed with Hep3B incubated with the conditioned medium from MRC-5 cells incubation with EVs from CTL-KD or NID1-KD cells for 72 hours. Anti-TNFR1 neutralizing antibody was added to neutralize the activity of soluble TNFR1 (Ab) (0.4 µg/ml) in the conditioned medium. Representative image shows the fixed and crystal violet-stained colonies. (G) Migration and invasion assays performed using PLC/PRF/5 cells pretreated as described in (F). Representative image shows the fixed and crystal violet-stained migratory and invasive cells. (H) Bioluminescence imaging of mice (n=6) subjected to intravenous coinjection of murine p53−/−; Myc hepatoblasts (1×10⁵) with PBS, IgG (10 µg) or anti-TNFR1 antibody (TNFR1 Ab) (10 µg). Quantification of the luciferase signal is shown. (I) Ex vivo bioluminescence imaging of lung tissues. Quantification of the luciferase signal is shown. (J) Representative images of H&E staining of lung tissues. Examples of metastatic lesions are indicated by arrowheads. Insets show the enlarged area of the metastatic lesions. Magnification, 2.5×; Scale bar, 500 µm. Three independent experiments were performed in triplicate for assays shown in D-G. Data are represented as the mean±SEM; *P<0.05; P<0.01; *P<0.001; NS, not significant from Student's t-test.

FIGS. 7A-7E EV-NID1 and serum TNFR1 levels correlate with the tumor stage of HCC. (A) ELISA analysis of NID1 expression in circulating EVs obtained from sera collected from individuals without liver disease (Control) (n=12), patients with early (n=43) and late stage (n=22) HCC (left). ELISA analysis of serum TNFR1 in the same subjects (right). ELISA was performed in duplicate. (B) Correlation between EV-NID1 and serum TNFR1 levels determined in (A) using Pearson correlation test. (C) ROC curves of EV-NID1, serum TNFR1 and combined EV-NID1 and serum TNFR1 for discriminating control subjects and patients with early stage HCC. (D) ROC curves of AFP, AFP in combination with EV-NID1 or serum TNFR1 for discriminating control subjects and patients with early stage HCC. (E) Proposed signaling mediated by EV-NID1. The EV-NID1 level increases with HCC development. EV-NID1 derived from metastatic HCC cells promotes liver tumor development and distant metastasis to the lungs. EV-NID1 increases pulmonary vessel leakiness, angiogenesis, and colonization of cancer cells to the lungs and activates pulmonary fibroblasts to secrete TNFR1, which in turn promotes HCC cell growth and motility. ROC, receiver operating characteristic. Data are represented as the mean±SEM; *P<0.05 and **P<0.01 from Student's t-test.

FIGS. 8A-8F Treatment with TNFR1 neutralizing antibody effectively inhibits tumor growth and metastasis in mice implanted with metastatic tumor seed. (A) Schematic diagram of the treatment regimen applied to mice implanted with luciferase-labeled MHCC97L cells in the liver. Mice were administered PBS, IgG or anti-TNFR1 antibody (200 µg) via peritoneal injection every 4 days for 28 days (n=5). (B) Bioluminescence imaging of animals at the end of the experiment. Quantification of the luciferase signal is shown. The size of the liver tumors was measured and plotted. (C) Ex vivo bioluminescence imaging of livers. Quantification of the luciferase signal is shown. (D) Representative image of H&E staining of liver tissues showing the boundary of tumors obtained from (C). Dotted line indicates the bulging growth fronts of liver tumor. Arrows indicate the cluster of tumors nearby the liver-tumor boundary. Magnification, 20×; Scale bar, 100 nm. (E) Ex vivo bioluminescence imaging of lungs. Quantification of the luciferase signal is shown. (F) Body weight of the mice was measured twice a week and plotted against time. Data are represented as the mean±SEM; *P<0.05, P<0.01,*P<0.001 and NS, not significant from Student's t-test.

FIGS. 9A-9D Characterization of EVs extracted from the conditioned medium of parental cell lines. (A) Representative electron micrograph of isolated MHCC97L and MHCCLM3 EVs evaluated by Philips CM100 Transmission Electron Microscope. Scale bar, 100 nm. (B) Western blotting of EV molecular markers in isolated EVs and total cell lysate (TCL) of cell lines. Positive EV markers include Alix and TSG101 while negative EV markers are cis-Golgi marker GM130, nucleoporin p62 and cytoskeletal α-tubulin. (C) Amount of protein extracted from EVs derived from the same cell number of different cell lines. The analysis was performed in triplicate and analyzed using Student's t-test. Data are represented as the mean±SEM; P<0.01; *P<0.001 (D) Size distribution of indicated EVs measured by ZetaView® BASIC NTA PMX-120 (Particle Metrix GmbH).

Figure 10:
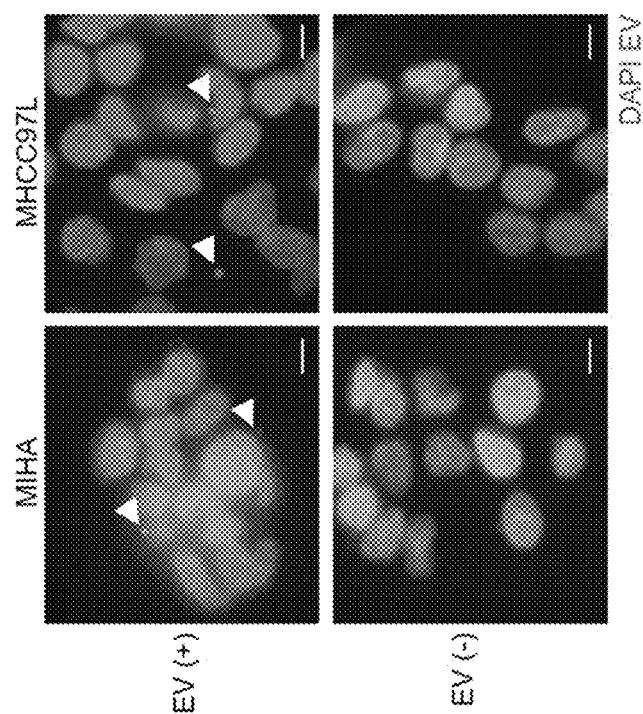

FIG. 10 Uptake of EVs by cells in culture. Fluorescence microscopy of HCC cells incubated with or without PKH26-labeled EVs (red) for 24 hr. Representative images of fixed and DAPI-stained cells. The PKH26-labeled EV is indicated by arrowhead. Scale bar: 10 µm.

FIGS. 11A-11B Reduction of EV secretion attenuates liver tumor formation. (A) Quantification of EVs isolated from conditioned medium of MHCC97L treated with 1 µM Tipifarnib or DMSO vehicle for 48 hr. The analysis was done in triplicate. (B) Image of dissected liver of mice subjected to orthotopic liver injection of Matrigel/MHCC97L (1×10⁶ cells/injection) pretreated with 48-hr DMSO or Tipifarnib (1 µM) (n=6). Measurement of tumor volume is shown. Data are represented as mean±SEM. *P<0.05 and ***P<0.001 from Student's t test.

Figure 12A:
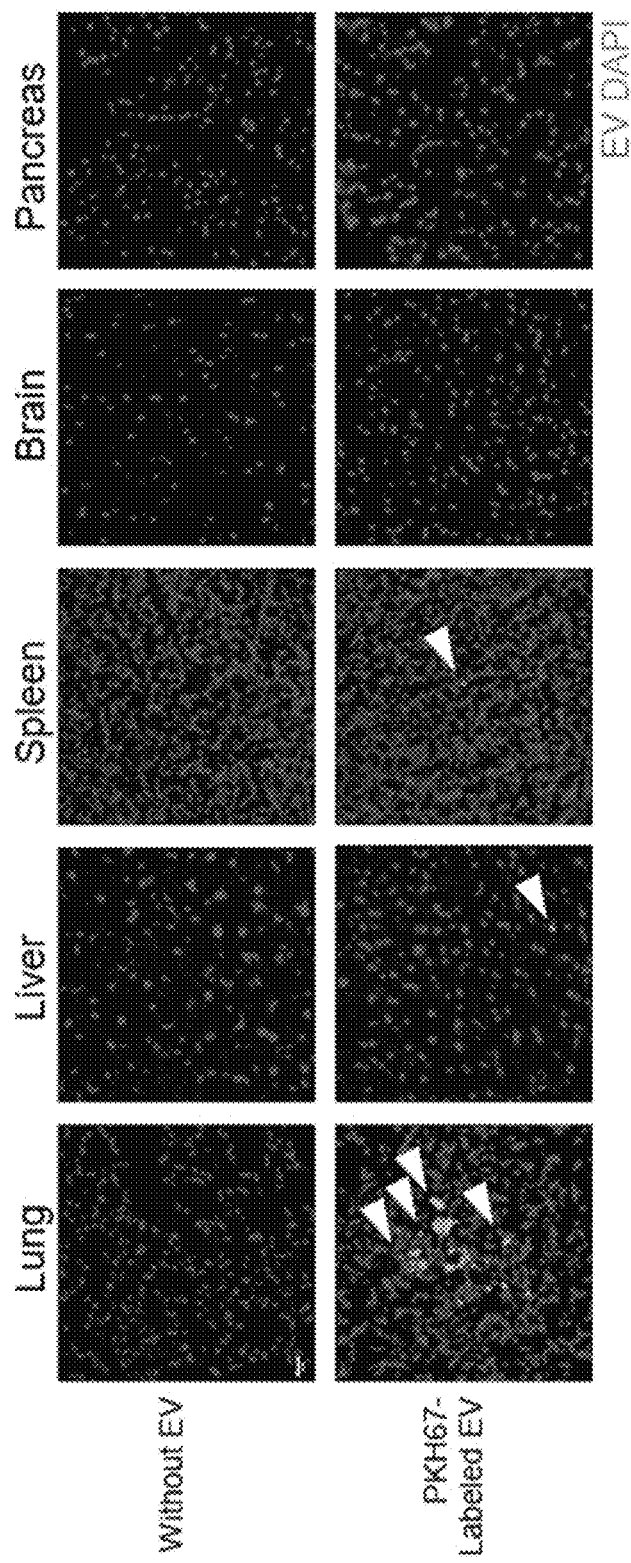
Figure 12B:
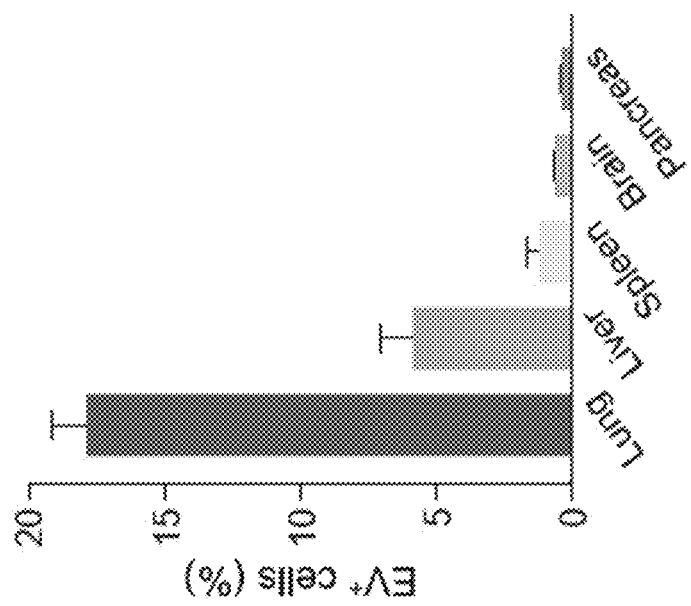

FIGS. 12A-12B Tissue distribution of EVs after tail vein injection in mice. (A) Confocal microscopy of DAPI-stained tissue section dissected from mice subjected to euthanasia, perfusion and fixation 24 hr after intravenous injection with PKH67-labeled EVs (green). Green signal is indicated by arrowhead. Scale bar: 10 µm. (B) Quantification of signal in 5 random fields in each of 3 tissue sections per organ is shown. Data are represented as mean±SEM.

FIGS. 13A-13E Quantification of circulating EVs obtained from mouse subjected to orthotopic liver implantation of HCC tumor seed. (A) Bioluminescence imaging of mice subjected to orthotopic liver implantation of tumor seed derived from luciferase labeled MHCC97L (n=5). Images showing luciferase signal of animals from week 1 to 5. (B) Plot showing luciferase intensity increased with time. (C) Protein extracted from circulating EVs isolated from 250 µl serum weekly is shown. Quantification of protein was performed in triplicate. Data are represented as mean±SEM. *P<0.05, and **P<0.01 from Student's t test. (D) Representative result showing the size distribution of circulating EVs isolated from blood of mouse at week 5 post implantation of tumor seed measured by ZetaView® BASIC NTA PMX-120 (Particle Metrix GmbH). (E) ELISA analysis of human CD63 expression in circulating EVs obtained from sera collected from mouse at week 5.

FIGS. 14A-14H NID1 promotes HCC cell growth, migration and invasiveness. (A) Immunoblotting showing NID1 expression in NID1 knockdown clones (NID1-KD1 and NID1-KD2) and non-target control clone (CTL-KD) established in MHCC97L. (B-C) Migration and invasion assays using control and NID1 knockdown cells. (D) NID1 expression in stable control clone (XPack) and EV-targeting NID1 clone (XP-NID1) established in Hep3B and HLE analyzed by western blotting. (E) Proliferation curve comparing the growth rates of XPack and NID-XP cells. XPack and NID-XP cells subjected to soft agar assay (F) migration (G) and invasion (H) assays. Three independent experiments were performed in triplicate for all functional assays. Data are represented as mean±SEM. *P<0.05, P<0.01, *P<0.001 and ****P<0.0001 from Student's t test.

FIGS. 15A-15D Characterization of EVs extracted from the conditioned medium of stable knockdown and overexpression clones of NID1. (A and B) Immunoblotting of EV markers of EVs isolated from the conditioned medium of MHCC97L control (CTL-KD) and NID1 knockdown (NID1-KD1 and NID1-KD2) cells, and control (XPack) and EV-targeting NID1 (XP-NID1) cells established in HLE and Hep3B. Positive EV markers include CD9 and TSG101 while negative EV markers are cis-Golgi marker GM130 and nucleoporin p62.Western blotting of EV molecular markers in isolated EVs and total cell lysate (TCL) of cell lines. (C and D) Size distribution of indicated EVs measured by ZetaView® BASIC NTA PMX-120 (Particle Metrix GmbH).

FIGS. 16A-16D EVs engineered to express NID1 promote tube formation of endothelial cells and colonization of hepatoma cells in lungs. (A) Tube formation assay of HUVEC pretreated with EVs of Hep3B XPack or XP-NID1. Three independent experiments were performed in triplicate. Quantification of capillary-like tubular structures formed is shown. (B) Analysis of lung colonization of mouse p53−/−; Myc hepatoblasts (1×10$^5$) 2 weeks after co-injection with EVs of Hep3B XPack or XP-NID1 cells (10 µg) though tail vein (n=6). Image of bioluminescence imaging of mice at the end of experiment. Quantification of luciferase signal is shown. (C) Bioluminescence imaging of dissected lung tissues. Quantification of luciferase signal is shown. (D) Representative images of H&E staining of lung tissues. Insets show the enlarged area of metastatic lesions. Magnification, 5×; Scale bar, 250 µm. Data are represented as mean±SEM. *P<0.05, P<0.01, **P<0.0001 and NS, not significant from Student's t test.

Figures 17A, 17B:
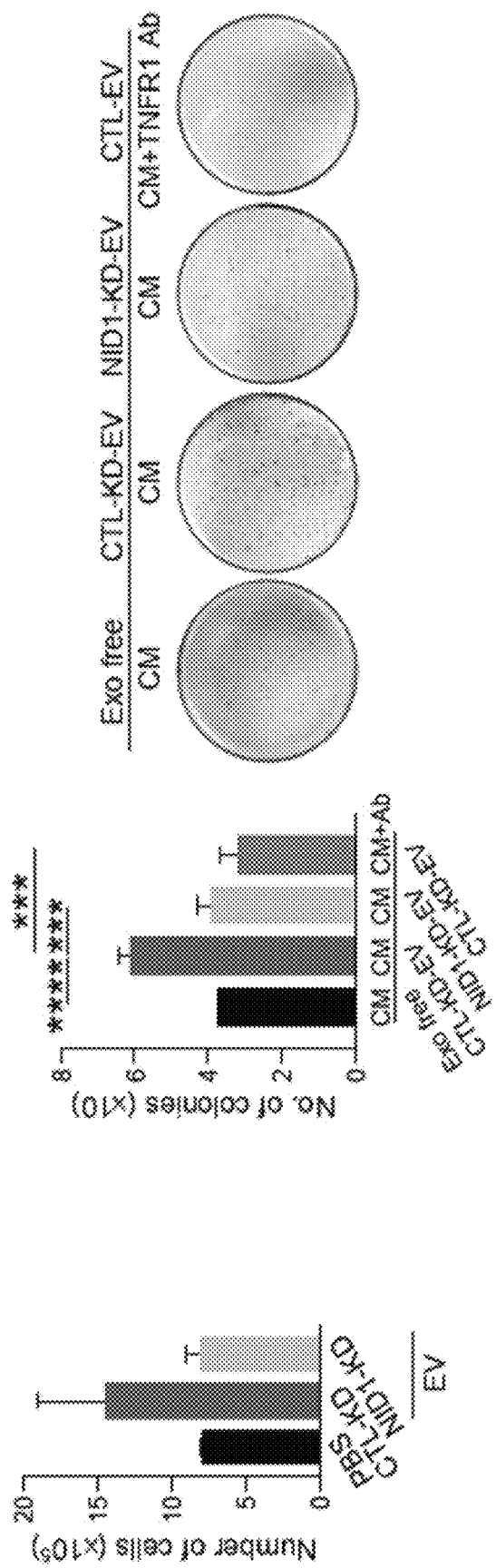
Figure 17C:
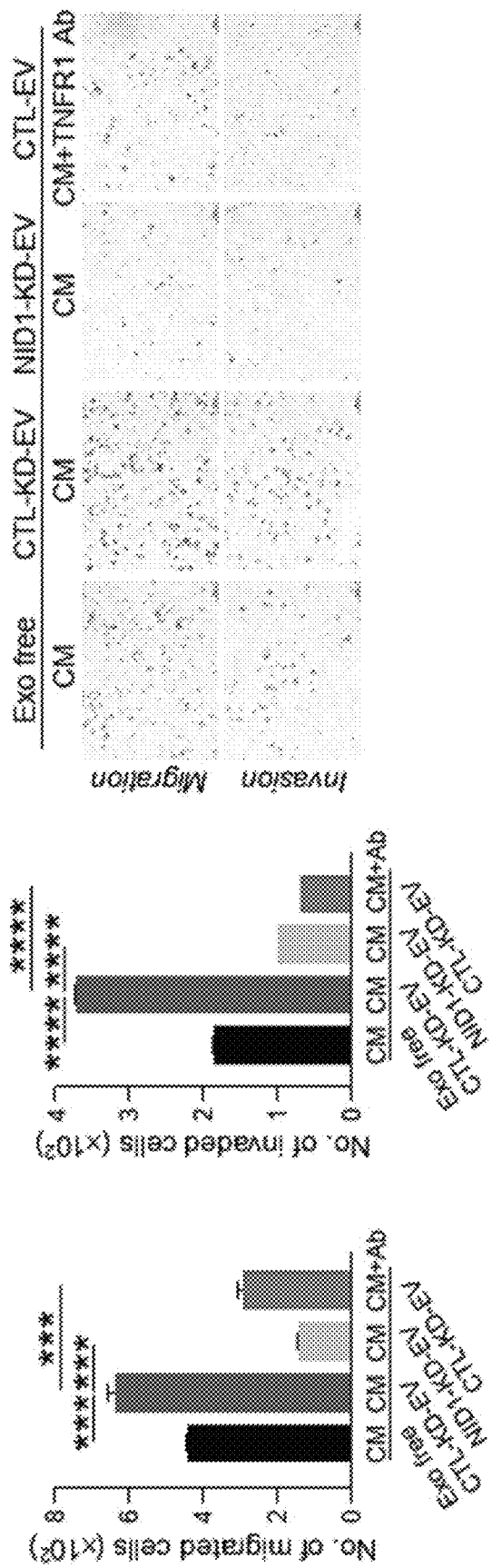

FIGS. 17A-17C TNFR1 secreted by EV-NID1-activated pulmonary fibroblasts promotes colony formation, migration and invasiveness. (A) Quantification of the cell number of MRC-5 after treatment with MHCC97L CTL-KD- and NID-KD1-Exo for 72 hr. (B) Colony formation assay was performed using Hep3B incubated with the conditioned medium of MCR-5 pre-treated with 72 hours of incubation with EVs of MHCC97L CTL-KD or NID1-KD1 cells. Anti-TNFR1 neutralizing antibody is added to neutralize the activity of secretory TNFR1 (Ab) (0.4 µg/ml) in the conditioned medium. Quantification of the number of colonies is shown. Representative image showing fixed and crystal violet-stained colonies. (C) Migration and invasion assays performed using Hep3B incubated with the conditioned medium of MCR-5 pre-treated with the indicated EVs for 72 hours. Anti-TNFR1 neutralizing antibody (Ab) (0.4 µg/ml) is added to neutralize the activity of secretory TNFR1 in the conditioned medium. Quantification of the number of migrated and invaded cells is shown. Representative image showing fixed and crystal violet-stained migrated and invaded cells. Three independent experiments were performed in triplicate for all functional assays. Data are represented as mean±SEM. *P<0.001 and **P<0.0001 from Student's t test.

Figure 18A:
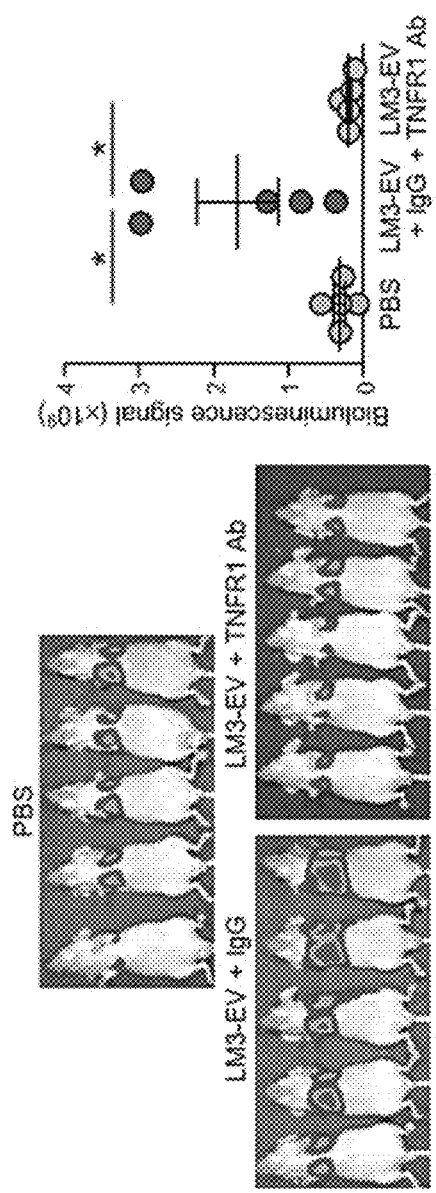
Figure 18B:
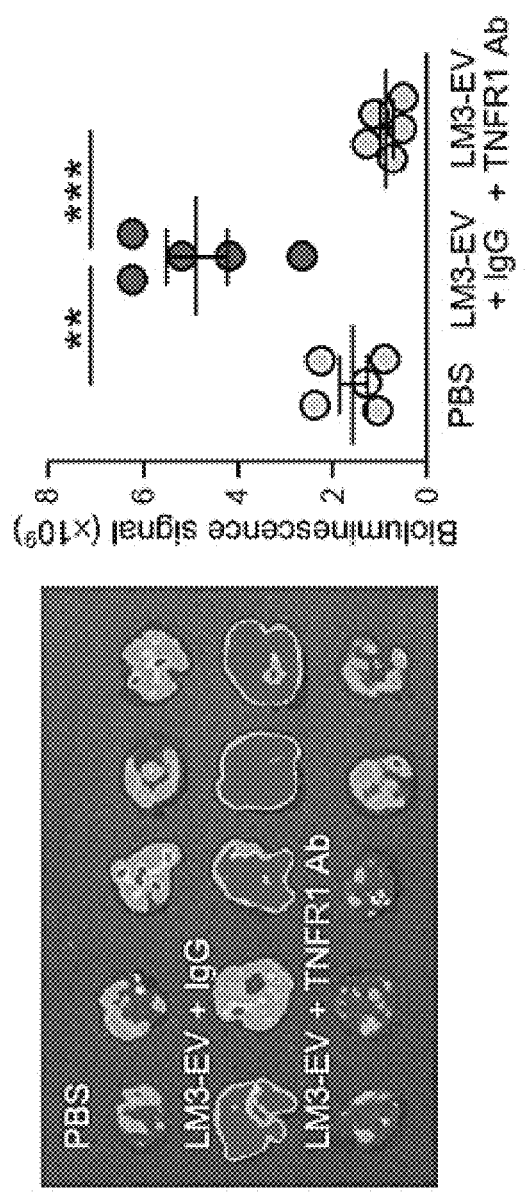
Figure 18C:
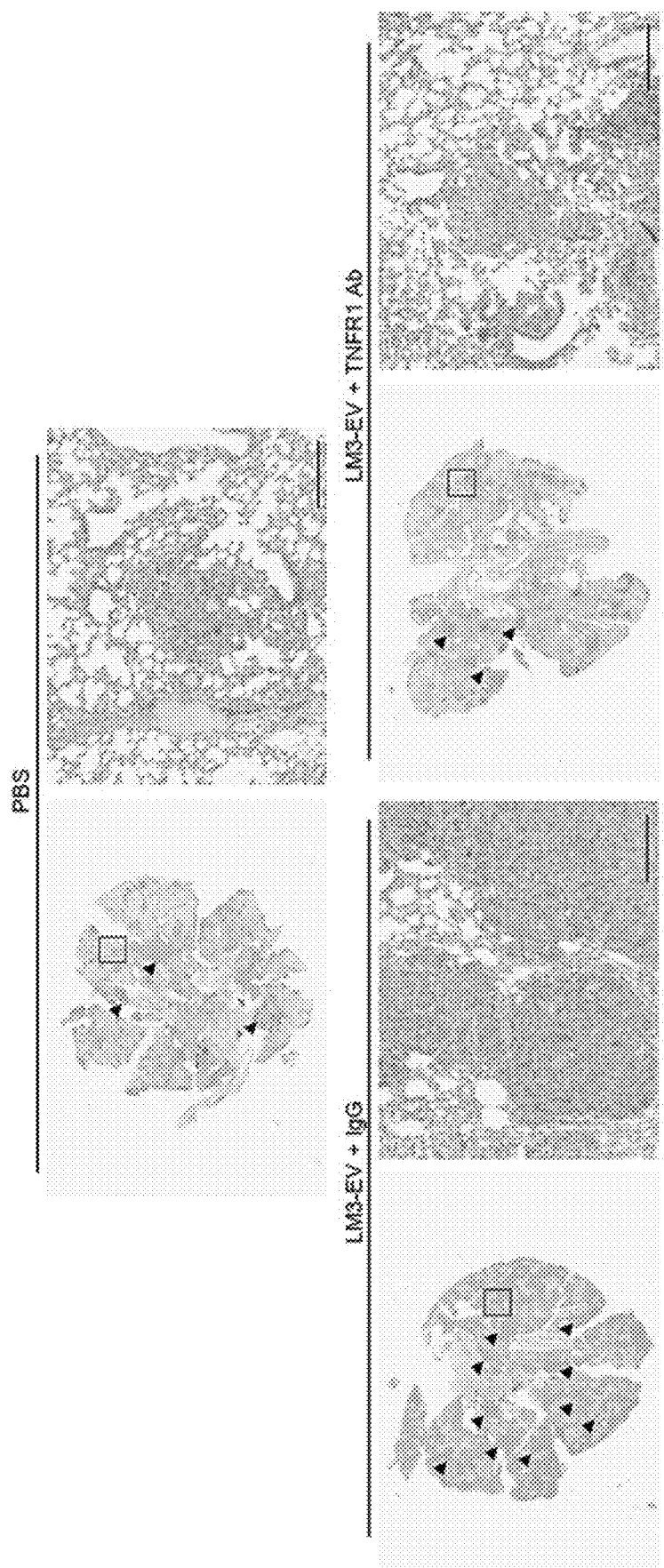

FIGS. 18A-18C Anti-TNFR1 antibody neutralizes the promoting effect of MHCCLM3 EVs in the colonization of murine p53−/−; Myc hepatoblasts into the lungs of animals. (A) Bioluminescence imaging of mice (n=5) subjected to intravenous coinjection of murine p53−/−; Myc hepatoblasts (1×10$^5$) with PBS, IgG (10 µg) or anti-TNFR1 antibody (TNFR1 Ab) (10 µg). Quantification of the luciferase signal is shown. (B) Ex vivo bioluminescence imaging of lung tissues. Quantification of the luciferase signal is shown. (C) Representative images of H&E staining of lung tissues. Examples of metastatic lesions are indicated by arrowheads. Insets show the enlarged area of the metastatic lesions. Magnification, 2.5×; Scale bar, 500 µm. Data are represented as the mean±SEM; *P<0.05; P<0.01; *P<0.001 from Student's t-test.

Figure 19A:
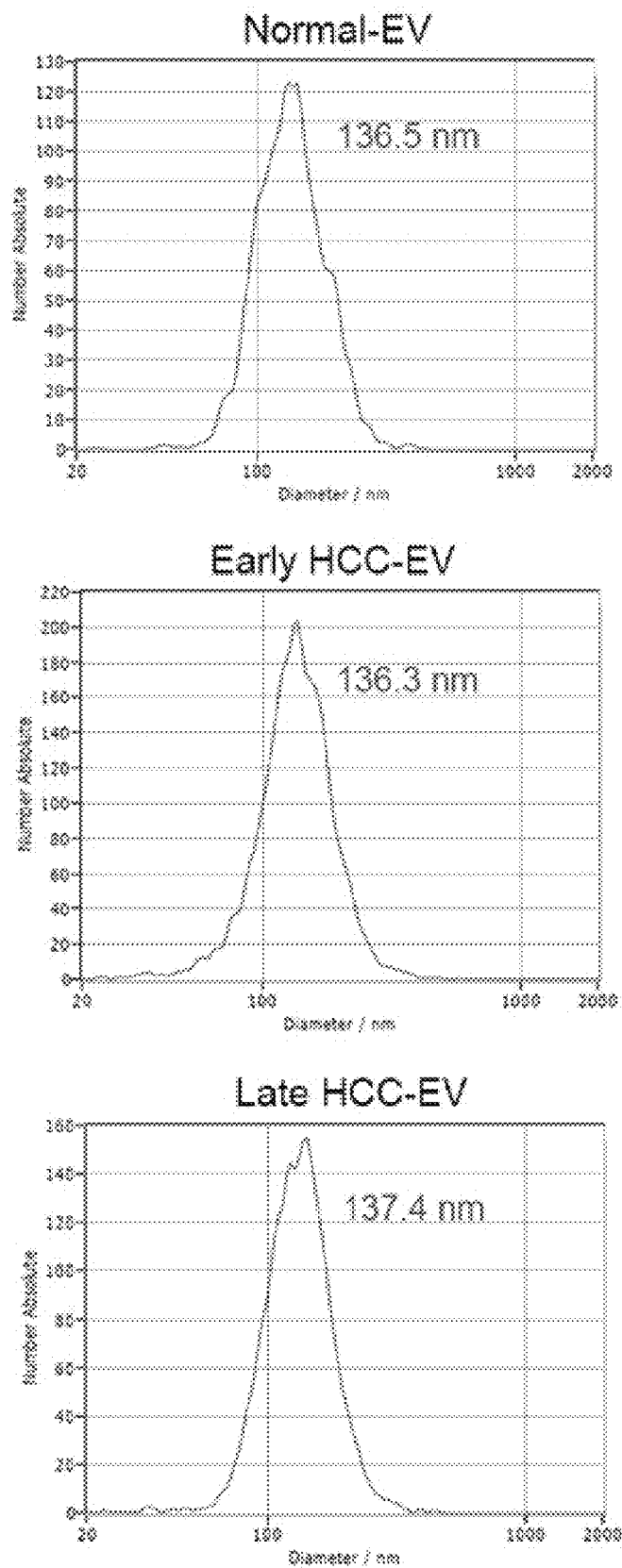
Figure 19B:
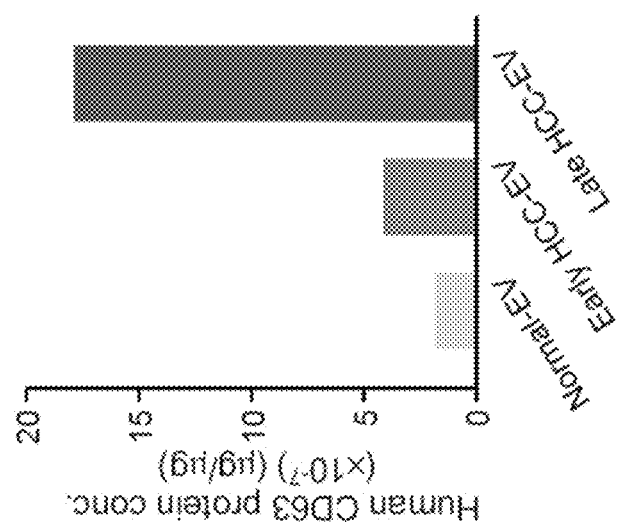
Figures 20A, 20B:
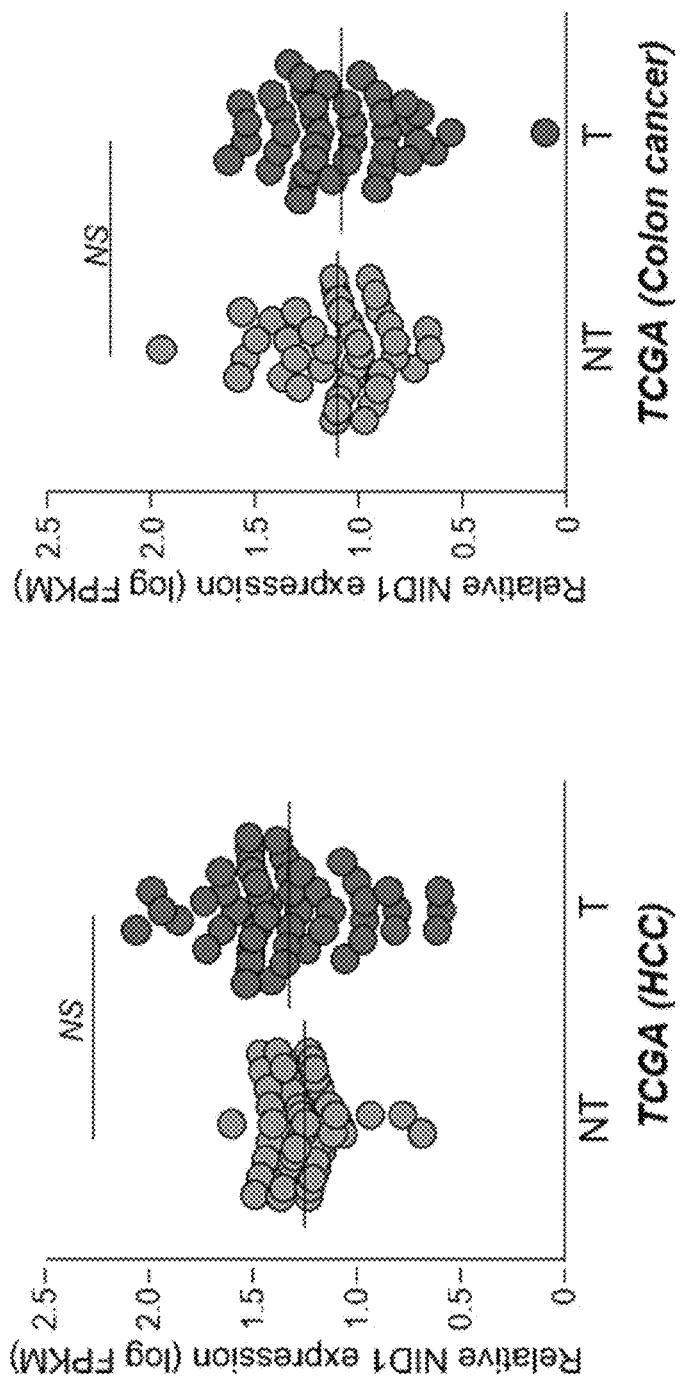
Figures 20C, 20D:
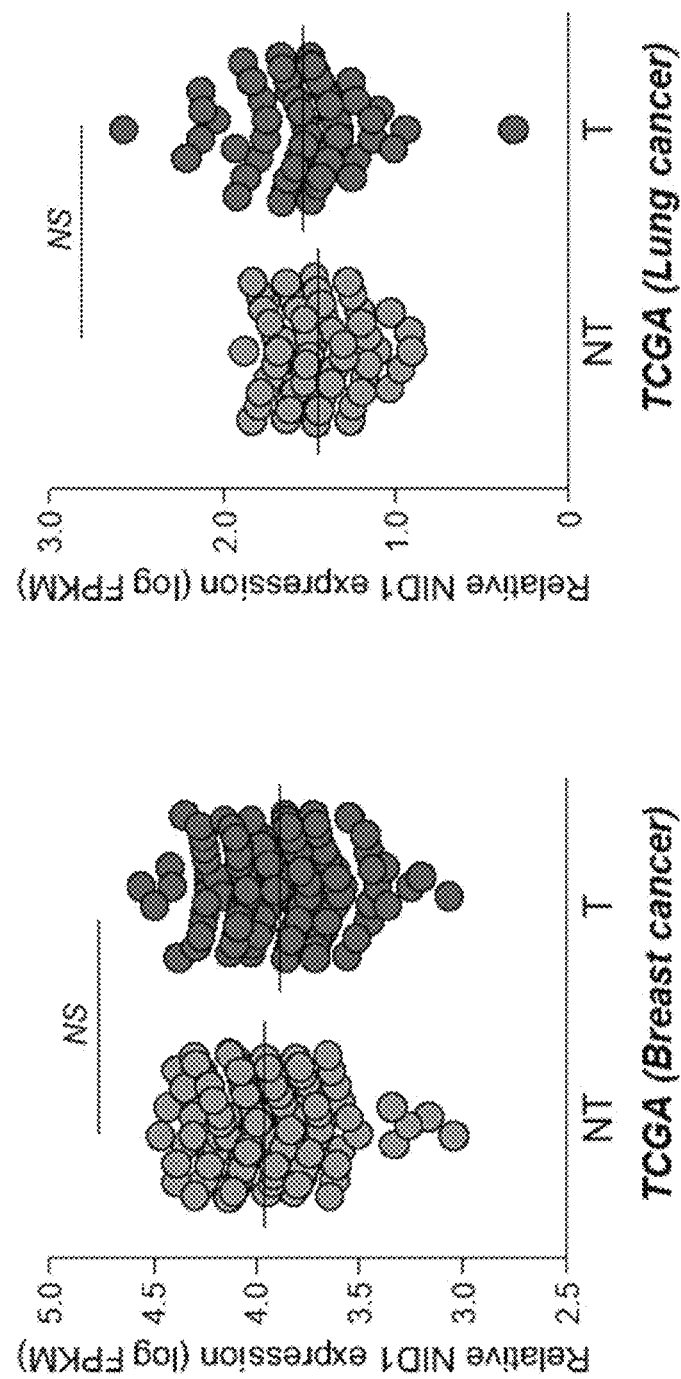

FIGS. 19A-19B Validation of isolated circulating EVs. (A) Size distribution of circulating EVs isolated from control subjects and patients with early and late HCC measured by ZetaView® BASIC NTA PMX-120 (Particle Metrix GmbH). (B) ELISA analysis of CD63 expression in circulating EVs obtained from sera collected from individuals without liver disease (Normal-EV), patients with early (Early HCC-EV) and late stage HCC (Late HCC-EV).

FIGS. 20A-20D Expression of NID1 in human solid tumors. NID1 expression was evaluated using TCGA database of hepatocellular carcinoma (HCC) (A), colon (B), breast (C) and lung (D) cancers and analyzed by Student's t test. NS, Non-significant.

FIG. 21 Results of mass spectromatry produced by Max-Quant software.

FIG. 22 Analysis of cytokines secreted by MRC-5 cells pre-treated with EV-NID1 by quantitative real-time PCR. Cytokine array was performed on untreated MRC-5 cells and MRC-5 cells treated with either EVs of MHCC97L non-target control (CTL-KD-EV) or NID1 knockdown (NID1-KD-EV) cells. Based on the reported findings of the potential candidates, various cytokines were selected for further analysis. To validate the expressions of selected cytokine candidates, quantitative realtime. PCR analysis was performed to analyze the relative expressions of cytokine candidates. The relative fold change of cytokine expression in MRC-5 treated with CTL-KD-EV and NID1-KD1-EV relative to that in untreated MRC-5 is shown.

FIG. 23 Information of blood donors.

FIG. 24 Oligonucleotides used in the study.

FIGS. 25A-25D Design of peptides for the generation of anti-NID1 antibody. A. Structural domain of NID1. The locations of the six suggested 12-residue peptides for antibody production along NID1 proteins are indicated by arrowheads. B. The epitope sequences were subjected to analysis using algorithm. An "epitope score" was assigned to each residue based on structural features, sequence conservation, hydrophobicity, solvent exposure and other criteria. C. Amino acid positions of the 12-residue epitopes are listed. In one embodiment, epitope sequence VHDDSRPALPST (SEQ ID NO: 36) is selected. D. Information of 14 ascites of anti-NID1 antibody is listed. These antibodies are to be tested for their neutralizing effect in the motility of HCC cells induced by NID1-enriched EVs. In one embodiment, the selected clone is #7 which is highlighted in red.

FIGS. 26A-26G Ascites of anti-NID1 antibody (#7) shows the best neutralizing effect on EVs that highly express NID1. A. Electron micrograph of EVs collected from metastatic HCC cell line, MHCC97L. MHCC97L-Evs were stained with anti-CD63 and anti-NID1 antibodies followed by secondary antibodies coupled to 5- and 15-nm gold particles, respectively. B. Representative results of migration and invasion assays performed on PLC/PRF/5 HCC cells pretreated with MHCC97L-EVs in the presence of IgG or ascites (#3, #4, #7 and #11). The statistical analysis was done in reference to the untreated group. C. Schematic diagram illustrates the structural difference and similarity between NID1 and NID2 (drawn to scale). Location of the selected peptide is indicated. Alignment of amino acid sequence of the selected epitope sequence between NID1 and NID2. Same residues between NID1 and NID2 are highlighted. D. Western blot analysis of NID1 expression in MHCC97L and HLE HCC cells stably transfected with XPack vector (XP) and XPack plasmid expressing EV-targeting NID1 (XP-NID1) using Ascites #7. E. Schematic diagram illustrating the analysis of lung colonization of murine p53−/−; Myc hepatoblasts 2 weeks after coinjection with circulating HCC-EVs via tail vein in the presence of PBS, IgG or Ab#7 (n=5). F. Image of bioluminescence signals of mice taken at the end of the experiment. Quantification of the luciferase signal is shown. G. Ex vivo bioluminescence imaging of dissected lungs. Intensity of luciferase signal is plotted. Data are represented as the mean±SEM; *$P<0.05$; $P<0.01$; *$P<0.001$; NS, not significant.

FIGS. 27A-27D Hybridoma clone #7 of anti-NID1 antibody shows inhibitory effect on MHCC97L-EV. A. Western blot analysis of NID1 expression in MHCC97L and HLE HCC cells stably transfected with XPack (XP) vector and XPack plasmid expressing EV-targeting NID1 (XP-NID1) using antibody purified from hybridoma cell line (Ab#7). B. Migration and invasion assays were performed on PLC/PRF/5 cells pretreated with MHCC97L-EVs in the presence of different amount of Ab#7. At the end of experiment, cells were fixed and stained. Representative images of migrated and invaded cells are shown. Number of cells were counted and plotted. C. PLC/PRF/5 cells pretreated with MHCC97L-EVs in the presence of different amount of Ab#7 were subjected to colony formation assay. Representative images of fixed and stained colonies are shown. Number of colonies were counted and plotted. D. MIHA cells were cultured in medium with or without Ab#7 (5 μg/ml) for 9 days. Number of cells were counted and plotted. Data are represented as the mean±SEM; *$P<0.05$; $P<0.01$; *$P<0.001$; NS, not significant.

FIGS. 28A-28D Neutralization effect of anti-NID1 antibody (Ab#7) in the promoting activity of EVs derived from late HCC patients. A. Electron micrograph of EVs collected from serum of HCC patient (HCC-EV) were stained with anti-CD63 and anti-NID1 antibodies followed by secondary antibodies coupled to 5- and 15-nm gold particles, respectively. B. Migration and invasion assays performed on PLC/PRF/5 cells pretreated with HCC-EV in the presence of either control IgG or Ab#7. C. Subcutaneous co-injection of HCC cells with or without HCC-EV together with either IgG or Ab#7. Tumor development was assessed after 3 weeks. D. Image of mice at the end of experiment. Tumors developed were marked. Data are represented as the mean±SEM; $P<0.01$; *$P<0.001$; NS, not significant.

FIGS. 29A-29D Tumor development of HCC patient-derived xenograft was inhibited by anti-NID1 antibody. A. Western blot analysis of total cell lysate (TCL) of HCC-patient-derived xenograft (PDX#1) using Ab#7. B. The level of NID1 in circulating EVs collecting from mice with or without injection of PDX#1 was measured by ELISA. C. Dissociated PDX#1 cells were subcutaneously injected into nude mice. Repeated administration of either IgG or Ab#7 by peritoneal injection was started when the size of tumors reached 0.1 m³. D. Image of mice at the end of experiment. Tumors developed were marked. Data are represented as the mean±SEM; ***$P<0.001$.

FIG. 30 Amino acid Sequence of NID1 (SEQ ID NO:39).

FIG. 31A-31B Nucleic acid sequence of NID1 (SEQ ID NO: 40).

5. DETAILED DESCRIPTIONS

In hepatocellular carcinoma (HCC) patients with extrahepatic metastasis, the lung is the most frequent site of metastasis. However, how the lung microenvironment favors disseminated cells remains unclear. Here, it is found that nidogen 1 (NID1) in metastatic HCC cell-derived extracellular vesicles (EVs) promoted pre-metastatic niche formation in the lung by enhancing angiogenesis and pulmonary endothelial permeability to facilitate colonization of tumor cells and extrahepatic metastasis. EV-NID1 also activated fibroblasts, which secreted tumor necrosis factor receptor 1 (TNFR1), facilitated lung colonization of tumor cells and augmented HCC cell growth and motility. Administration of anti-TNFR1 antibody effectively diminished lung metastasis induced by the metastatic HCC cell-derived EVs in mice. In the clinical perspective, analysis of serum EV-NID1 and TNFR1 in HCC patients revealed their positive correlation and association with tumor stages suggesting the potential of these molecules as noninvasive biomarkers for the early detection of HCC. In conclusion, these results demonstrated the interplay of HCC EVs and activated fibroblasts in pre-metastatic niche formation and how blockage of their functions inhibits distant metastasis to the lungs. This study offers promise for the new direction of HCC treatment by targeting oncogenic EV components and their mediated pathways.

As used herein, the term "subject" refers to animal, preferably a mammal. The mammalian subject may be a non-human mammal, but is generally a human, such as a human adult. The subject will in general be a living subject. However, whilst the uses, methods and compositions of the present disclosure are suited for screening, diagnosis and prognosis of a living subject, they may also be used for postmortem diagnosis in a subject, for example, to identify family members at risk of developing the same disease.

As used herein, the term "patient" refers to a subject who has or is suspected of having one or more of the disease or disorder.

Nidogen 1 ("NID1") has been found to be differentially expressed in various cancers thus providing a new target for affinity-based therapies of these cancers. A human sequence of the NID1 protein is given in SEQ ID NO: 39 (Genbank accession no. NP_002499.2). The term NID1 (in the context of a protein) encompasses proteins whose amino acid sequences consist of or comprise the amino acid sequence given in NP_002499.2 or derivatives or variants thereof, particularly naturally-occurring human derivatives or variants thereof. The nucleotide sequence encoding this protein is found at accession number, as given in SEQ ID NO: 40 (Genbank accession no. NM_002508.3).

The disclosure described in detail below encompasses the administration of therapeutic compositions to a subject, e.g. a mammalian subject, to treat or prevent cancer, e.g. the disease or disorder. The disclosure also provides methods and compositions for clinical screening, diagnosis and prognosis of cancer, e.g. the disease or disorder, in a mammalian subject for identifying patients most likely to respond to a particular therapeutic treatment, for monitoring the results of cancer e.g. the disease or disorder therapy, for drug screening and drug development.

The disclosure is based on the finding that NID1 protein is expressed in subjects with HCC extrahepatic metastasis. In one embodiment, the lung is the most frequent site of metastasis. In particular, supporting data is enclosed herein which demonstrates the expression of NID1 metastatic HCC cell-derived extracellular vesicles (EVs) which promoted pre-metastatic niche formation extrahepatically, such as the lungs, by enhancing angiogenesis and pulmonary endothelial permeability to facilitate colonization of tumor cells and extrahepatic metastasis. Therefore, antibodies directed to NID1 have utility as therapeutics and diagnostics in these cancers and other cancer types showing expression of NID1.

Figure 25A:
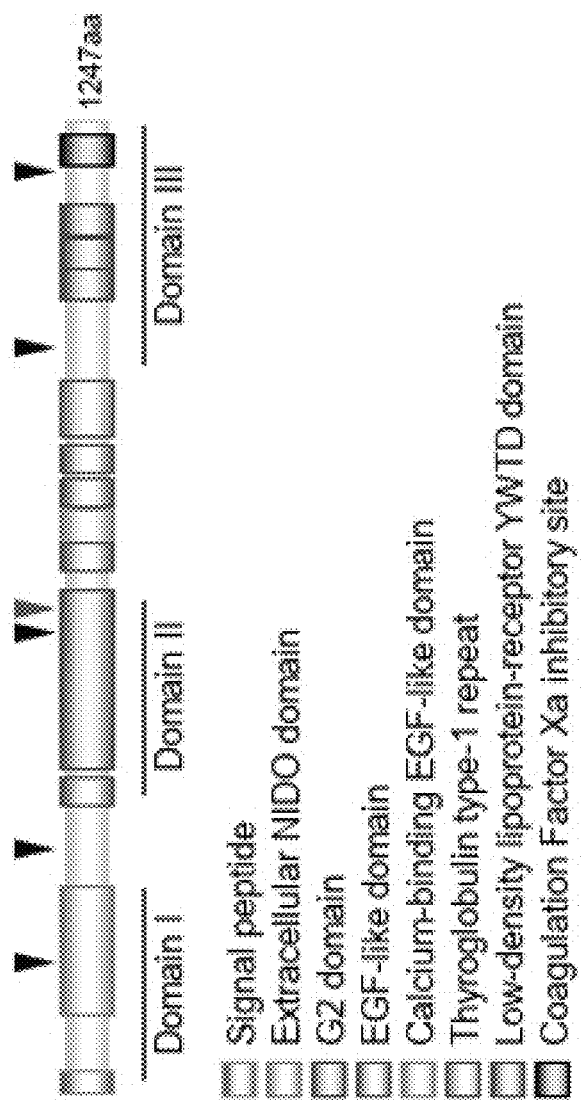
Figure 25B:
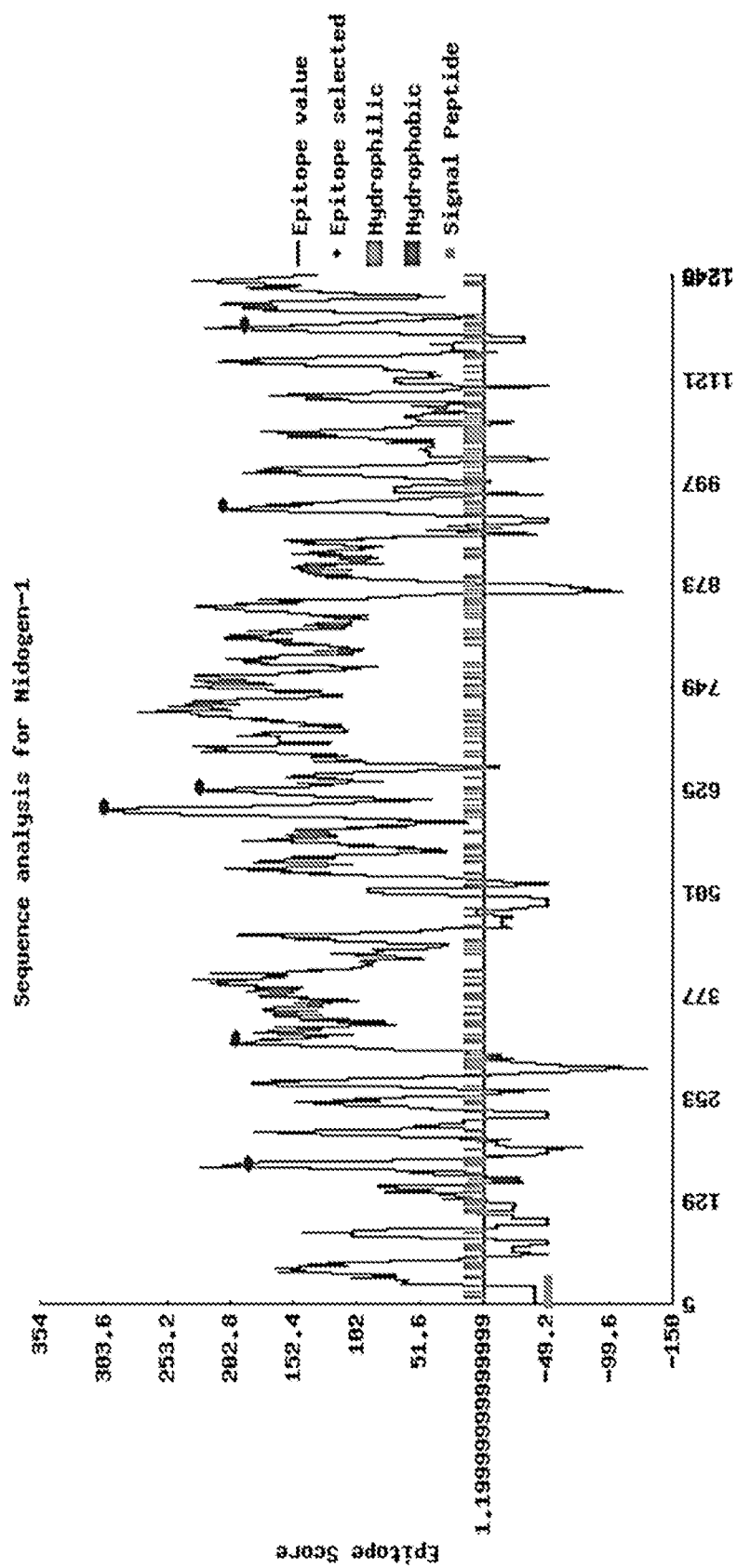
Figures 26A, 26B:
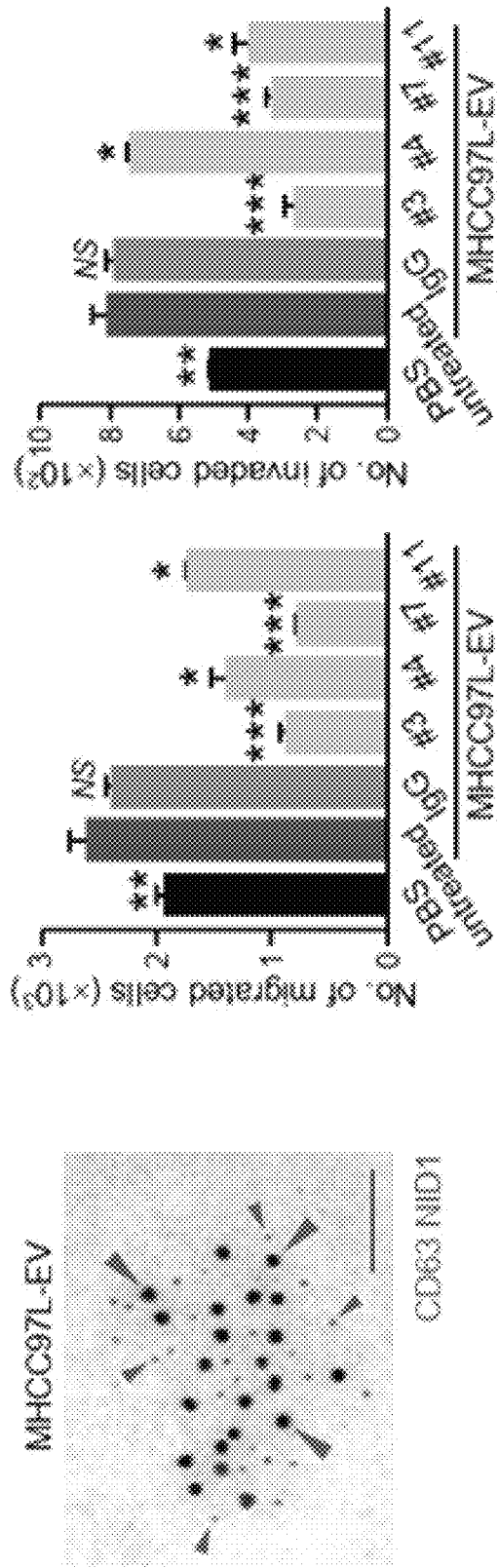
Figures 26C, 26D:
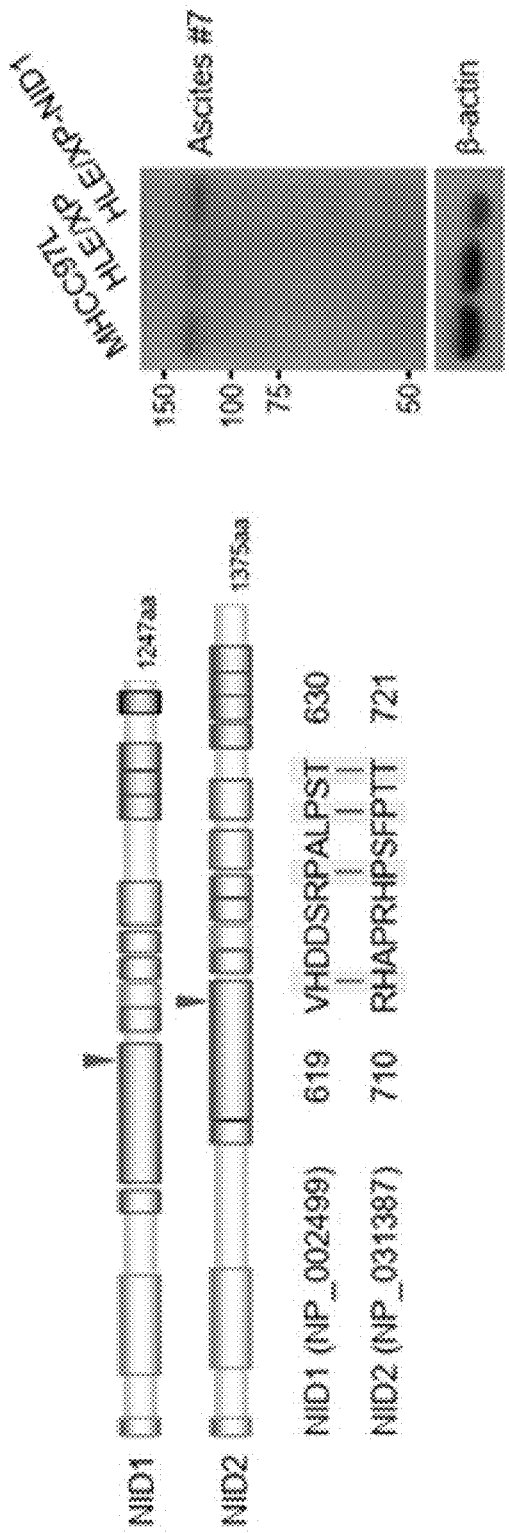
Figure 26F:
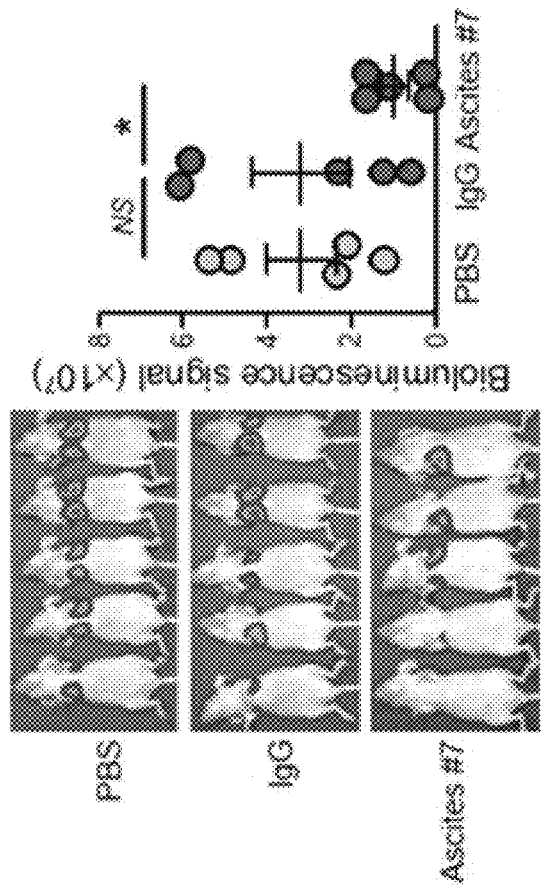
Figure 26E:
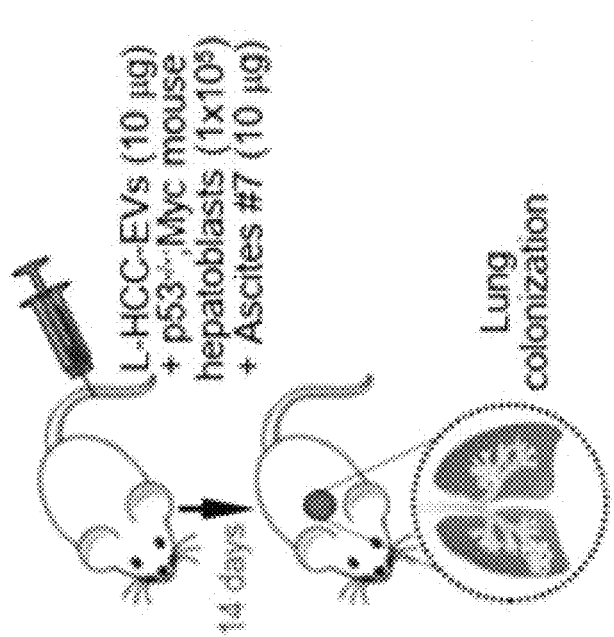
Figure 26G:
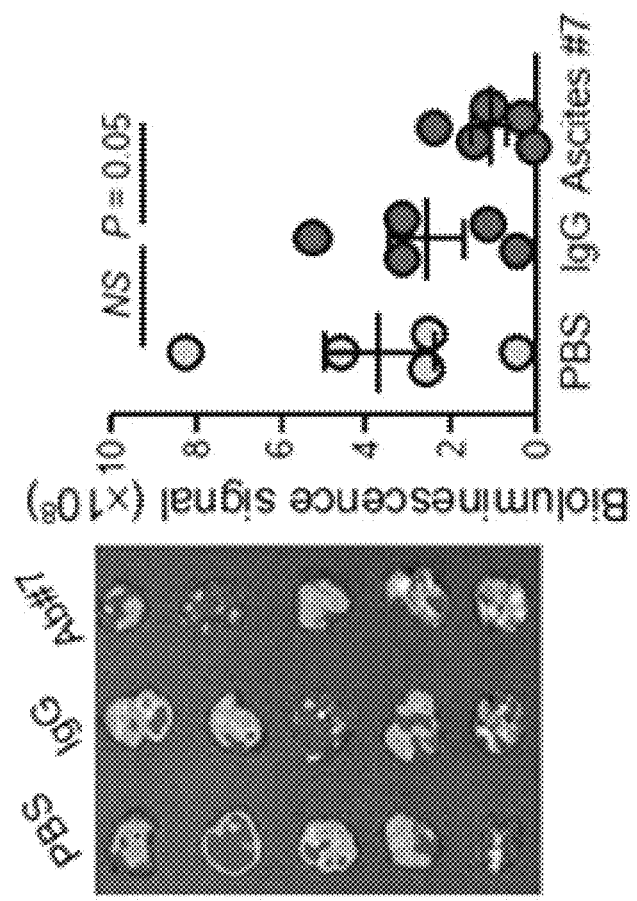
Figure 27A:
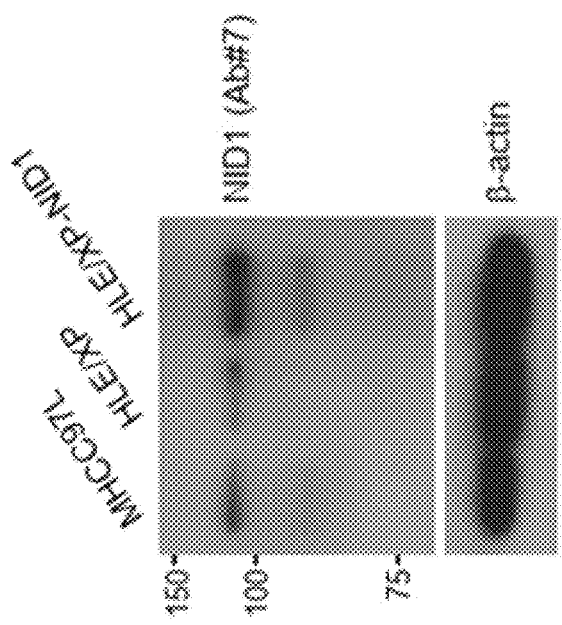
Figure 27B:
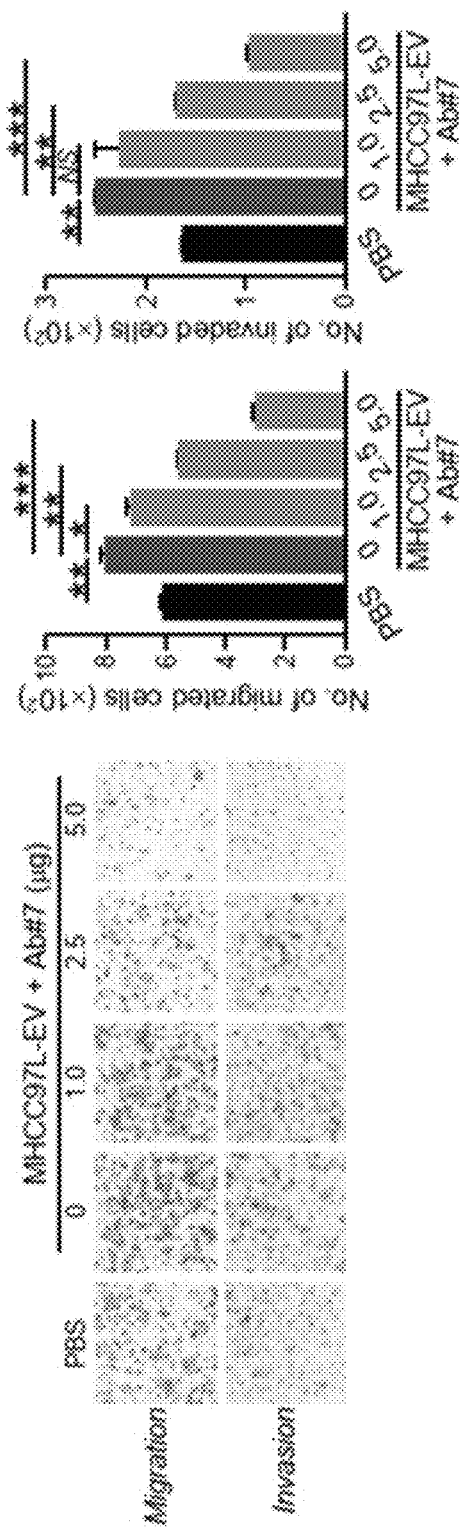
Figure 27C:
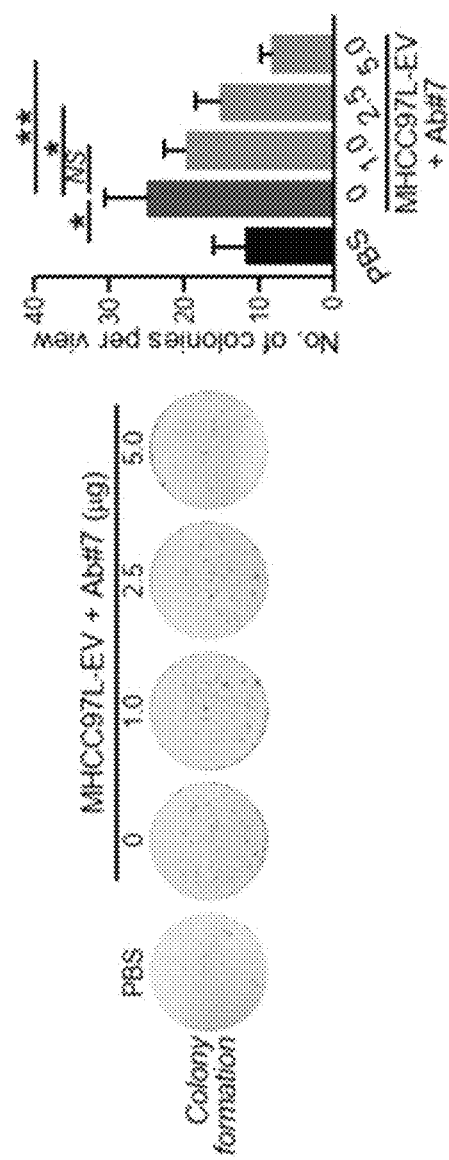
Figure 27D:
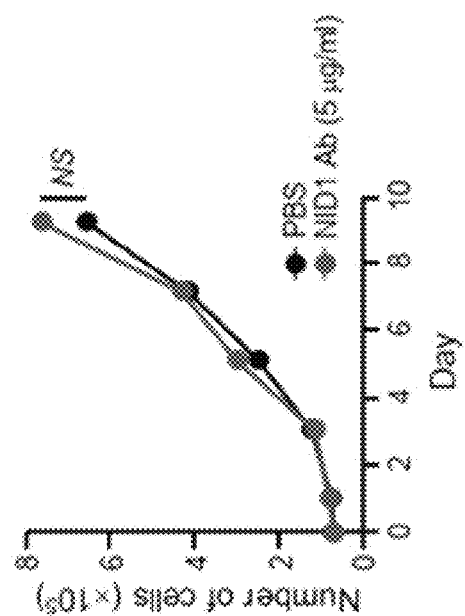
Figures 28A, 28B:
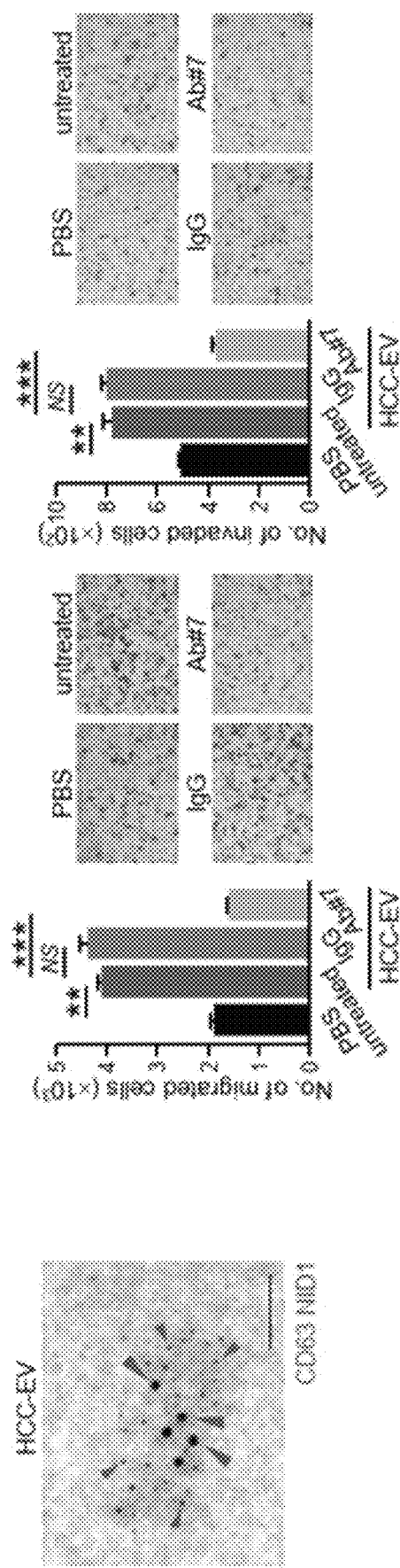
Figure 28D:
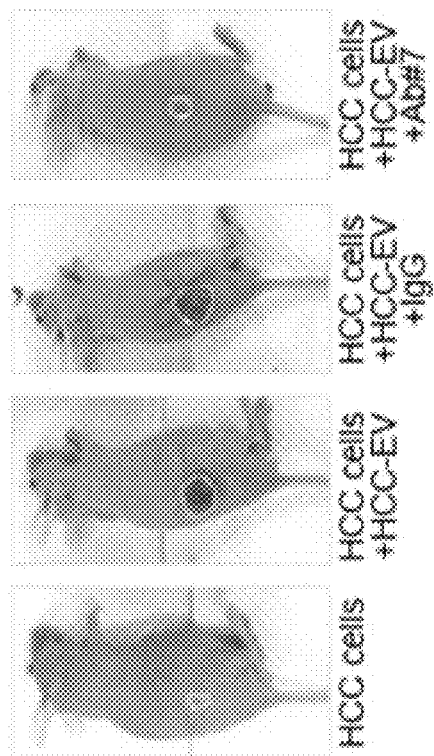
Figure 28C:
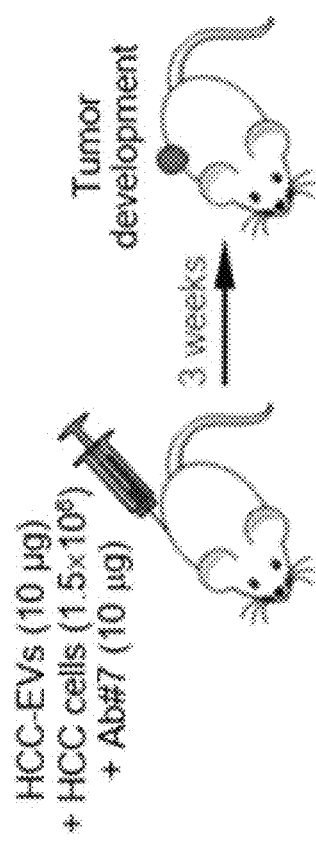
Figure 29B:
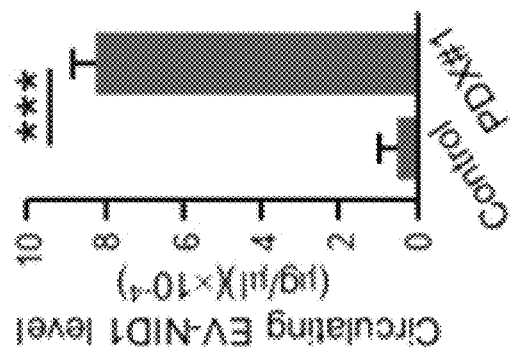
Figure 29A:
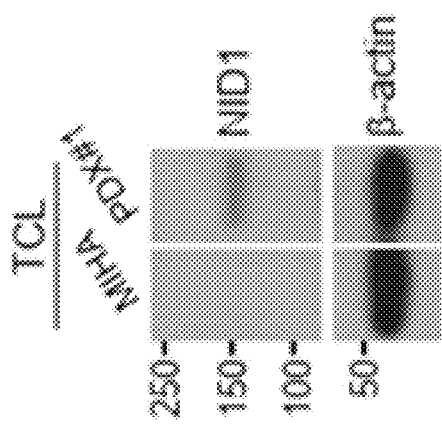
Figure 29D:
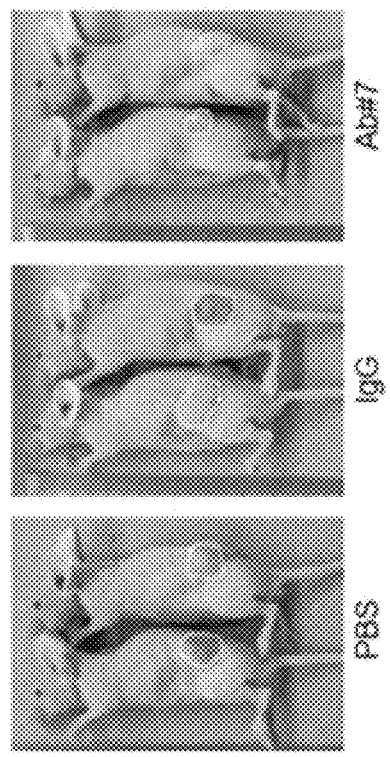
Figure 29C:
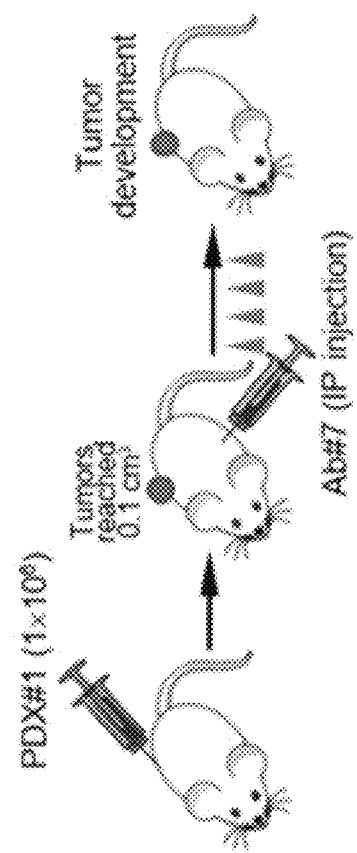

NID1 is useful as are fragments particularly epitope containing fragments e.g. antigenic or immunogenic fragments thereof and derivatives thereof, particularly fragments comprising extracellular domains (e.g. extracellular NIDO domain), G2 domain, EGF-like domain, calcium-binding EGF-like domain, Thyroglobulin type-1 repeat, low-density lipoprotein-receptor YWTD domain and coagulation factor Xa inhibitory site of the protein (See FIG. 25A). In one embodiment, the immunogenic fragment is amino acid residues 619 to 630 of NID1 protein SEQ ID NO: 39 (Genbank accession no. NP_002499.2). Epitope containing fragments, including antigenic or immunogenic fragments, will typically be of length 12 amino acids or more, e.g. 20 amino acids or more, e.g. 50 or 100 amino acids or more. Fragments may be 95% or more of the length of the full protein, e.g. 90% or more, e.g. 75% or 50% or 25% or 10% or more of the length of the full protein.

Alternatively, the protein/polypeptide employed or referred to herein may be limited to those proteins/polypeptides specifically recited/described in the present specification or to a variant or derivative which has at least 80, 85, 90, 91, 92, 93, 94, 95, 96, 97, 98 or 99% amino acid sequence identity or similarity thereto. Percentage amino acid sequence identity/similarity may be determined by any suitable algorithm, e.g. BLAST, CLUSTAL, using appropriate default parameters.

Hence the term "NID1" in the context of a protein or polypeptide refers to a protein whose amino acid sequence consists of or comprises the amino sequence given in any of NP_002499.2 or a derivative or variant thereof which has at least 90% or 95% sequence identity to any of NP_002499.2 and which protein has essentially the same tissue distribution as NID1.

In the context of a nucleic acid, the term "NID1" refers to a nucleic acid whose nucleotide sequence encodes a protein comprising the amino sequence given in any of SEQ ID NO: 39 or a derivative or variant thereof which has at least 90% or 95% sequence identity to any of SEQ ID NO: 39 and which protein has essentially the same tissue distribution as NID1 protein.

The term "NID1" in the context of a nucleic acid also refers to a nucleic acid whose nucleotide sequence comprises the sequence in SEQ ID NO: 40 (Genbank accession no. NM_002508) or a derivative or variant thereof which has at least 90% or 95% sequence identity to any of SEQ ID NO: 40 (Genbank accession no. NM_002508) and which encodes a protein which has essentially the same tissue distribution as NID1 protein.

Epitope-containing fragments of NID1 including antigenic or immunogenic fragments will be capable of eliciting a relevant immune response in a patient. DNA encoding NID1 is also useful as are fragments thereof, e.g. DNA encoding fragments of NID1 such as immunogenic fragments thereof. Fragments of nucleic acid (e.g. DNA) encoding NID1 may be 95% or more of the length of the full coding region, e.g. 90% or more e.g. 75% or 50% or 25% or 10% or more of the length of the full coding region. Fragments of nucleic acid (e.g. DNA) may be 36 nucleotides or more, e.g. 60 nucleotides or more, e.g. 150 or 300 nucleotides or more in length.

Derivatives of NID1 include variants on the sequence in which one or more (e.g. 1-20 such as 15 amino acids, or up to 20% such as up to 10% or 5% or 1% by number of amino acids based on the total length of the protein) deletions, insertions or substitutions have been made. Substitutions may typically be conservative substitutions. Derivatives will typically have essentially the same biological function as the protein from which they are derived. Derivatives will typically be comparably antigenic or immunogenic to the protein from which they are derived. Derivatives will typically have either the ligand-binding activity, or the active receptor-complex forming ability, or preferably both, of the protein from which they are derived. Derivatives and variants will generally have the same tissue distribution as NID1.

Derivatives of proteins also include chemically treated protein such as carboxymethylated, carboxyamidated, acetylated proteins, for example treated during purification.

In one aspect, the disclosure provides NID1 or a composition comprising NID1. The protein may be in isolated or purified form. The disclosure further provides a nucleic acid encoding NID1 and a composition comprising a nucleic acid encoding NID1.

In a further aspect, there is provided a composition capable of eliciting an immune response in a subject, which composition comprises a NID1 polypeptide and/or one or more antigenic or immunogenic fragments thereof, and one or more suitable carriers, excipients, diluents or adjuvants (suitable adjuvants are discussed below).

The composition capable of eliciting an immune response may for example be provided as a vaccine comprising a NID1 polypeptide or derivative or variant thereof, and/or one or more antigenic or immunogenic fragments thereof, optionally together with one or more suitable carriers, excipients, diluents or adjuvants.

In one aspect, the disclosure provides a NID1 polypeptide, or one or more fragments or derivatives or variants thereof, for the treatment or prophylaxis of e.g. one or more of the disease or disorder.

In one aspect, the disclosure provides a use of an anti-NID1 molecule, or one or more fragments or derivatives or variants thereof, for the treatment or prophylaxis of, e.g. one or more of cancers.

The disclosure also provides a use of a NID1 polypeptide, one or more fragments or derivatives or variants thereof, in the manufacture of a medicament for the treatment or prophylaxis of e.g. one or more of the diseases.

In one aspect there is provided a method of treatment comprising administering a therapeutically effective amount of a NID1 polypeptide, one or more fragments or derivatives or variants thereof, for the treatment or prophylaxis of e.g. one or more of the diseases.

The disclosure further provides a method for the treatment or prophylaxis of e.g. the diseases in a subject, or of vaccinating a subject against e.g. one or more of the diseases, which comprises the step of administering to the subject an effective amount of a NID1 polypeptide and/or one or more antigenic or immunogenic fragments or derivatives or variants thereof, for example as a vaccine.

In another aspect, the disclosure provides methods of treating e.g. the diseases comprising administering to a patient a therapeutically effective amount of a compound that modulates (e.g. downregulates) the expression or the biological activity (or both) of NID1 in patients having e.g. the disease or disorder, in order to (a) prevent the onset or development of e.g. the disease or disorder; (b) prevent the progression of e.g. the disease or disorder; or (c) ameliorate the symptoms of e.g. the diseases.

In yet a further embodiment, the disclosure provides a medicament comprising, separately or together: (a) anti-NID1 molecule, and (b) an anti-cancer agent, for simultaneous, sequential or separate administration in the treatment of cancer, preferably in the treatment of one of the disease or disorder.

NID1 can be used for detection, prognosis, diagnosis, or monitoring of, e.g. the disease or disorder or for drug development.

According to one aspect of the disclosure, we provide a method of detecting, diagnosing and/or screening for or monitoring the progression of e.g. the disease or disorder or of monitoring the effect of e.g. an anti-cancer drug or therapy directed towards the disease or disorder in a subject which comprises detecting the presence or level of NID1, or one or more fragments thereof, or the presence or level of nucleic acid encoding NID1 or the presence or level of the activity of NID1 or which comprises detecting a change in the level thereof in said subject.

According to another aspect of the disclosure we provide a method of detecting, diagnosing and/or screening for e.g. the disease or disorder in a candidate subject which comprises detecting the presence of NID1, or one or more fragments thereof, or the presence of nucleic acid encoding NID1 or the presence of the activity of NID1 in said candidate subject, in which either (a) the presence of an elevated level of NID1 or said one or more fragments thereof or an elevated level of nucleic acid encoding NID1 or the presence of an elevated level of NID1 activity in the candidate subject as compared with the level in a healthy subject or (b) the presence of a detectable level of NID1 or said one or more fragments thereof or a detectable level of nucleic acid encoding NID1 or the presence of a detectable level of NID1 activity in the candidate subject as compared with a corresponding undetectable level in a healthy subject indicates the presence of e.g. the disease or disorder in said subject.

According to another aspect of the disclosure, we provide a method of monitoring the progression of e.g. the disease or disorder in a subject or of monitoring the effect of e.g. an anti-cancer drug or therapy directed towards the disease or disorder which comprises detecting the presence of NID1, or one or more fragments thereof, or the presence of nucleic acid encoding NID1 or the presence of the activity of NID1 in said candidate subject at a first time point and at a later time point, the presence of an elevated or lowered level of NID1 or said one or more fragments thereof or an elevated or lowered level of nucleic acid encoding NID1 or the presence of an elevated or lowered level of NID1 activity in the subject at the later time point as compared with the level in the subject at said first time point, indicating the progression or regression of e.g. the disease or disorder or indicating the effect or non-effect of e.g. an anti-cancer drug or therapy directed towards the disease or disorder in said subject.

For NID1, the detected level obtained upon analyzing tissue sample from subjects having e.g. the disease or disorder relative to the detected level obtained upon analyzing tissue from subjects free from e.g. the disease or disorder will depend upon the particular analytical protocol and detection technique that is used. Accordingly, the present disclosure contemplates that each laboratory will establish a reference range in subjects free from e.g. the disease or disorder according to the analytical protocol and detection technique in use, as is conventional in the diagnostic art. Preferably, at least one control positive tissue sample from a subject known to have e.g. the disease or disorder or at least one control negative tissue sample from a subject known to be free from e.g. the disease or disorder (and more preferably both positive and negative control samples) are included in each batch of test samples analyzed.

In one aspect of the disclosure, liquid chromatography-mass spectrometry analysis or other appropriate methods are used to analyze the tissue samples from a subject, preferably a living subject, in order to measure the expression of NID1 for screening or diagnosis of e.g. the disease or disorder, to determine the prognosis of the patient, to monitor the effectiveness of the therapy, or for drug development.

In any of the above methods, the level that may be detected in the candidate subject who has cancer, e.g. the disease or disorder is 1.5-2 folds, 2-2.5 folds, 2.5-3 folds, 3-3.5 folds, 3.5-4 folds, 4-4.5 folds, 4.5-5 folds, 5-5.5 folds, 5.5-6 folds, higher in EV-NID1 than the level in the healthy subject. In certain embodiments, control showed a range of 0.0005-0.0032 µg/µg EV-NID1. In certain embodiments, early-stage patients showed a range of 0.0007-0.0172 µg/µg EV-NID1. In certain embodiments, late-stage patients showed a range of 0.0013-0.0264 µg/µg EV-NID1. In certain embodiments, control showed a range of 4.65-10.26 µg/ml TNFR1. In certain embodiments, early-stage patients showed a range of 5.00-32.42 µg/ml TNFR1. In certain embodiments, late-stage patients showed a range of 6.73-54.77 µg/ml TNFR1. In certain embodiments, there is overlapping of the detection range between diseased state versus control subjects. In certain embodiments, the ranges of EV-NID1 and serum TNFR1 of control subjects are 0.0005-0.0032 µg/µg and 4.65-10.26 µg/ml, respectively. In certain embodiments, expression levels of EV-NID1 and serum TNFR1 higher than 0.0032 µg/µg and 10.26 µg/ml, respectively, indicate diseased state.

In one embodiment, tissue sample from a subject (e.g. a subject suspected of having the disease or disorder) is analyzed by liquid chromatography-mass spectrometry for detection of NID1. An increased abundance of NID1 in the tissue from the subject relative to tissue from a subject or subjects free from the disease or disorder (e.g. a control sample) or a previously determined reference range indicates the presence of the disease or disorder.

As used herein, NID1 is "isolated" when it is present in a preparation that is substantially free of contaminating proteins, i.e. a preparation in which less than 10% (for example less than 5%, such as less than 1%) of the total protein present is contaminating protein(s). A contaminating protein is a protein having a significantly different amino acid sequence from that of isolated NID1, as determined by mass spectral analysis. As used herein, a "significantly different" sequence is one that permits the contaminating protein to be resolved from NID1 by mass spectral analysis.

In the diagnostic and prognostic methods of the disclosure, NID1 can be assayed by any method known to those skilled in the art, including but not limited to, kinase assays, enzyme assays, binding assays and other functional assays, immunoassays, and western blotting.

Alternatively, NID1 can be detected in an immunoassay. In one embodiment, an immunoassay is performed by contacting a sample from a subject to be tested with an anti-NID1 antibody (or other affinity molecule) under conditions such that binding (e.g. immunospecific binding) can occur if NID1 is present, and detecting or measuring the amount of any binding (e.g. immunospecific binding) by the agent. NID1 binding agents can be produced by the methods and techniques taught herein. In a particular embodiment, NID1 is analysed using immunohistochemistry.

NID1 may be detected by virtue of the detection of a fragment thereof e.g. an epitope containing (e.g. an immunogenic or antigenic) fragment thereof. Fragments may have a length of 10-20, 20-50, 50-100, 100-150, 150-200, 200-300, 300-500, 500-600, 600-700, 700-800, 800-900 amino acids.

In one embodiment, binding of an affinity molecule (e.g. an antibody) in tissue sections can be used to detect aberrant NID1 localization or an aberrant level of NID1. In a specific embodiment, an antibody (or other affinity molecule) to NID1 can be used to assay a patient tissue (e.g. a lung, breast, squamous cell carcinoma, ovarian, colorectal tissue) for the level of NID1 where an aberrant level of NID1 is indicative of the disease or disorder. As used herein, an "aberrant level" means a level that is increased compared with the level in a subject free from the disease or disorder or a reference level.

Any suitable immunoassay can be used, including, without limitation, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays and protein A immunoassays.

For example, NID1 can be detected in a fluid sample (e.g. blood, urine, or saliva) by means of a two-step sandwich assay. In the first step, a capture reagent (e.g. an anti-NID1 antibody or other affinity molecule) is used to capture NID1. The capture reagent can optionally be immobilized on a solid phase. In the second step, a directly or indirectly labelled detection reagent is used to detect the captured NID1.

If desired, a gene encoding NID1, a related gene, or related nucleic acid sequences or subsequences, including complementary sequences, can also be used in hybridization assays. A nucleotide encoding NID1, or subsequences thereof comprising at least 8 nucleotides, preferably at least 12 nucleotides, and most preferably at least 15 nucleotides can be used as a hybridization probe. Hybridization assays can be used for detection, prognosis, diagnosis, or monitoring of conditions, disorders, or disease states, associated with aberrant expression of the gene encoding NID1, or for differential diagnosis of subjects with signs or symptoms suggestive of e.g. the disease or disorder. In particular, such a hybridization assay can be carried out by a method comprising contacting a subject's sample containing nucleic acid with a nucleic acid probe capable of hybridizing to a DNA or RNA that encodes NID1, under conditions such that hybridization can occur, and detecting or measuring any resulting hybridization.

Hence nucleic acid encoding NID1 (e.g. DNA or more suitably RNA) may be detected, for example, using a hybridizing agent (particularly an oligonucleotide probe) capable of hybridizing to nucleic acid encoding NID1.

One such exemplary method comprises: contacting one or more oligonucleotide probes comprising 10 or more consecutive nucleotides complementary to a nucleotide sequence encoding NID1, with an RNA obtained from a biological sample from the subject or with cDNA copied from the RNA, wherein said contacting occurs under conditions that permit hybridization of the probe to the nucleotide sequence if present; detecting hybridization, if any, between the probe and the nucleotide sequence; and comparing the hybridization, if any, detected in step (b) with the hybridization detected in a control sample, or with a previously determined reference range.

The disclosure also provides diagnostic kits, comprising an anti-NID1 antibody (or other affinity molecule). In addition, such a kit may optionally comprise one or more of the following: (1) instructions for using the anti-NID1 molecule for diagnosis, prognosis, therapeutic monitoring or any combination of these applications; (2) a labelled binding partner to the affinity molecule; (3) a solid phase (such as a reagent strip) upon which the anti-NID1 molecule is immobilized; and (4) a label or insert indicating regulatory approval for diagnostic, prognostic or therapeutic use or any combination thereof. If no labelled binding partner to the affinity molecule is provided, the anti-NID1 molecule itself can be labelled with a detectable marker, e.g. a chemiluminescent, enzymatic, fluorescent, or radioactive moiety.

The disclosure also provides a kit comprising a nucleic acid probe capable of hybridizing to nucleic acid, suitably RNA, encoding NID1. In a specific embodiment, a kit comprises one or more containers a pair of primers (e.g. each in the size range of 6-30 nucleotides, more preferably 10-30 nucleotides and still more preferably 10-20 nucleotides) that under appropriate reaction conditions can prime amplification of at least a portion of a nucleic acid encoding NID1, such as by polymerase chain reaction, ligase chain reaction or other methods known in the art.

A kit can optionally further comprise a predetermined amount of NID1 or a nucleic acid encoding NID1, e.g. for use as a standard or control.

As used herein, the term "sample" includes a bodily fluid (e.g. blood, urine or saliva) and tissue biopsies taken from a subject at risk of having one or more of the disease or disorder (e.g. a biopsy such as a lung, breast, squamous cells, ovary, colon) or homogenate thereof.

For example, the biological sample used can be from any source such as a serum sample or a tissue sample e.g. lung. For instance, when looking for evidence of metastatic the disease or disorder, one would look at major sites of the disease or disorder metastasis, e.g. the brain, liver, bones and adrenal glands for lung cancer; the liver for pancreatic cancer or the lungs, brain and bones for skin cancer.

Alternatively the presence of NID1, or one or more fragments thereof, or the presence of nucleic acid encoding NID1 or the presence of the activity of NID1 may be detected by analysis in situ.

In certain embodiments, methods of diagnosis described herein may be at least partly, or wholly, performed in vitro or ex vivo.

Suitably the presence of NID1, or one or more fragments thereof, or the presence of nucleic acid encoding NID1 or the presence of the activity of NID1 is detected quantitatively.

For example, quantitative detection comprises: contacting a biological sample with an affinity molecule that is specific for NID1, said affinity molecule optionally being conjugated to a detectable label; and detecting whether binding has occurred between the affinity molecule and at least one species in the sample, said detection being performed either directly or indirectly.

Alternatively, the presence of NID1, or one or more fragments thereof, or the presence of nucleic acid encoding NID1 or the presence of the activity of NID1 may be detected quantitatively by means involving use of an imaging technology.

In another embodiment, the method of the disclosure involves use of immunohistochemistry on e.g. lung sections in order to determine the presence of NID1, or one or more fragments thereof, or the presence of nucleic acid encoding NID1 or the presence of the activity of NID1, and thereby to localize e.g. the disease or disorder cells.

In one embodiment, the presence of NID1 or one or more epitope-containing fragments thereof is detected, for example using an affinity molecule capable of specific binding to NID1 or one or more fragments thereof, such as an antibody.

In another embodiment the activity of NID1 is detected.

5.1 Use in Clinical Studies

The diagnostic methods and compositions of the present disclosure can assist in monitoring a clinical study, e.g. to evaluate drugs for therapy of the disease or disorder. In one embodiment, candidate molecules are tested for their ability to restore NID1 levels in a subject having e.g. the disease or disorder to levels found in subjects free from the disease or disorder or, in a treated subject, to preserve NID1 levels at or near non-lung cancer values.

In another embodiment, the methods and compositions of the present disclosure are used to screen candidates for a clinical study to identify individuals having e.g. the disease or disorder; such individuals can then be excluded from the study or can be placed in a separate cohort for treatment or analysis.

5.2 Protein and Nucleic Acids

The disclosure provides a method of treating or preventing e.g. the disease or disorder, comprising administering to a subject in need of such treatment or prevention a therapeutically effective amount of nucleic acid encoding NID1 or one or more fragments or derivatives thereof, for example in the form of a vaccine.

In another aspect there is provided a method of treating or preventing e.g. the disease or disorder comprising administering to a subject in need of such treatment or prevention a therapeutically effective amount of nucleic acid that inhibits the function or expression of NID1.

The methods (and/or other DNA aspects disclosed herein) of the disclosure may, for example include wherein the nucleic acid is a NID1 anti-sense nucleic acid or ribozyme.

Thus, the disclosure includes the use of nucleic acid encoding NID1 or one or more fragments or derivatives thereof, in the manufacture of a medicament for treating or preventing e.g. the disease or disorder.

There is also provided the use of nucleic acid that inhibits the function or expression of NID1 in the manufacture of a medicament for treating or preventing e.g. one or more of the disease or disorder.

DNA encoding the polypeptide consisting of an amino acid sequence that is substantially identical to the amino acid sequence of NID1 or DNA encoding the polypeptide consisting of an amino acid sequence derived from the amino acid sequence of NID1 by deletion, substitution, or addition of one or more amino acids composing a portion of the amino acid sequence can be easily produced by an appropriate combination of, for example, a site-directed mutagenesis method, a gene homologous recombination method, a primer elongation method, and the PCR method known by persons skilled in the art. In addition, at this time, a possible method for causing a polypeptide to have substantially equivalent biological activity is substitution of homologous amino acids (e.g. polar and nonpolar amino acids, hydrophobic and hydrophilic amino acids, positively-charged and negatively charged amino acids, and aromatic amino acids) among amino acids composing the polypeptide. Furthermore, to maintain substantially equivalent biological activity, amino acids within functional domains contained in the polypeptide of the present disclosure are preferably conserved.

Furthermore, examples of DNA of the present disclosure include DNA comprising a nucleotide sequence that encodes the amino acid sequence of NID1 and DNA hybridizing under stringent conditions to the DNA and encoding a polypeptide (protein) having biological activity (function) equivalent to the function of the polypeptide consisting of the amino acid sequence of NID1. Under such conditions, an example of such DNA capable of hybridizing to DNA comprising the nucleotide sequence that encodes the amino acid sequence of NID1 is DNA comprising a nucleotide sequence that has a degree of overall mean homology with the entire nucleotide sequence of the DNA, such as approximately 80% or more, preferably approximately 90% or more, and more preferably approximately 95% or more. Hybridization can be carried out according to a method known in the art such as a method described in Current Protocols in Molecular Biology (edited by Frederick M. Ausubel et al., 1987) or a method according thereto. Here, "stringent conditions" are, for example, conditions of approximately "1×SSC, 0.1% SDS, and 37° C., more stringent conditions of approximately "0.5×SSC, 0.1% SDS, and 42° C., or even more stringent conditions of approximately "0.2×SSC, 0.1% SDS, and 65° C. With more stringent hybridization conditions, the isolation of a DNA having high homology with a probe sequence can be expected. The above combinations of SSC, SDS, and temperature conditions are given for illustrative purposes. Stringency similar to the above can be achieved by persons skilled in the art using an appropriate combination of the above factors or other factors (for example, probe concentration, probe length, and reaction time for hybridization) for determination of hybridization stringency.

Recombinant NID1 polypeptide may be prepared by processes well known in the art from genetically engineered host cells comprising expression systems. Accordingly, the present disclosure also relates to expression systems which comprise a NID1 polypeptide or nucleic acid, to host cells which are genetically engineered with such expression systems and to the production of NID1 polypeptide by recombinant techniques. For recombinant NID1 polypeptide production, host cells can be genetically engineered to incorporate expression systems or portions thereof for nucleic acids. Such incorporation can be performed using methods well known in the art, such as, calcium phosphate transfection, DEAD-dextran mediated transfection, transfection, microinjection, cationic lipid-mediated transfection, electroporation, transduction, scrape loading, ballistic introduction or infection (see e.g. Davis et al., Basic Methods in Molecular Biology, 1986 and Sambrook et al., Molecular Cloning: A Laboratory Manual, $2^{nd}$ Ed., Cold Spring Harbor laboratory Press, Cold Spring Harbor, N.Y., 1989).

As host cells, for example, bacteria of the genus *Escherichia, Streptococci, Staphylococci, Streptomyces,* bacteria of the genus *Bacillus,* yeast, *Aspergillus* cells, insect cells, insects, and animal cells are used. Specific examples of bacteria of the genus *Escherichia,* which are used herein, include *Escherichia coli* K12 and DH1 (Proc. Natl. Acad. Sci. U.S.A., Vol. 60, 160 (1968)), JM103 (Nucleic Acids Research, Vol. 9, 309 (1981)), JA221 (Journal of Molecular Biology, Vol. 120, 517 (1978)), and HB101 (Journal of Molecular Biology, Vol. 41, 459 (1969)). As bacteria of the genus *Bacillus,* for example, *Bacillus subtilis* MI114 (Gene, Vol. 24, 255 (1983)) and 207-21 (Journal of Biochemistry, Vol. 95, 87 (1984)) are used. As yeast, for example, *Saccharomyces cerevisiae* AH22, AH22R-, NA87-11A, DKD-5D, and 20B-12, *Schizosaccharomyces pombe* NCYC1913 and NCYC2036, and *Pichia pastoris* are used. As insect cells, for example, *Drosophila* S2 and *Spodoptera* Sf9 cells are used. As animal cells, for example, COS-7 and Vero monkey cells, CHO Chinese hamster cells (hereinafter abbreviated as CHO cells), dhfr-gene-deficient CHO cells, mouse L cells, mouse AtT-20 cells, mouse myeloma cells, rat GH3 cells, human FL cells, COS, HeLa, C127,3T3, HEK 293, BHK and Bowes melanoma cells are used.

Cell-free translation systems can also be employed to produce recombinant polypeptides (e.g. rabbit reticulocyte lysate, wheat germ lysate, SP6/T7 in vitro T&T and RTS 100 *E. Coli* HY transcription and translation kits from Roche Diagnostics Ltd., Lewes, UK and the TNT Quick coupled Transcription/Translation System from Promega UK, Southampton, UK).

The appropriate nucleic acid sequence may be inserted into an expression system by any variety of well-known and routine techniques, such as those set forth in Sambrook et al., supra. Appropriate secretion signals may be incorporated into the NID1 polypeptide to allow secretion of the translated protein into the lumen of the endoplasmic reticulum, the periplasmic space or the extracellular environment. These signals may be endogenous to the NID1 polypeptide or they may be heterologous signals. Transformation of the host cells can be carried out according to methods known in the art. For example, the following documents can be referred to: Proc. Natl. Acad. Sci. U.S.A., Vol. 69, 2110 (1972); Gene, Vol. 17, 107 (1982); Molecular & General Genetics, Vol. 168, 111 (1979); Methods in Enzymology, Vol. 194, 182-187 (1991); Proc. Natl. Acad. Sci. U.S.A.), Vol. 75, 1929 (1978); Cell Technology, separate volume 8, New Cell Technology, Experimental Protocol. 263-267 (1995) (issued by Shujunsha); and Virology, Vol. 52, 456 (1973).

5.3 Production of anti-NID1 Molecules

In one aspect, the disclosure provides an affinity or immunoaffinity molecule which is capable of specific binding to NID1 or a fragment thereof, for example an affinity molecule which contains or is conjugated to a detectable label or contains or is conjugated to a therapeutic moiety, such as a cytotoxic moiety. The affinity agent may, for example, be an antibody. The affinity molecule may be an isolated affinity molecule or a purified affinity molecule.

In certain embodiments, the affinity molecule for use in the disclosure may bind to an epitope on NID1, e.g. one or more of the portions of SEQ ID NO: 39 (Genbank accession No. NP_002499). In certain embodiments, the affinity molecule specifically binds to extracellular NIDO domain, G2 domain, etc. of NID1 of SEQ ID NO: 40 (Genbank accession no. NP_002499). See FIG. 25A.

According to those skilled in the art, immunoaffinity molecules include but are not limited to—monoclonal antibodies, phage display antibodies and smaller antibody-derived molecules such as Affibodies, Domain Antibodies (dAbs), Nanobodies, UniBodies, DARPins, Anticalins, Duocalins, Avimers or Versabodies. In general, in applications according to the present disclosure where the use of antibodies is stated, other affinity molecules (e.g. Affibodies, Domain Antibodies, Nanobodies, UniBodies, DARPins, Anticalins, Duocalins, Avimers or Versabodies) may be employed. Such substances are capable of immunospecifically binding to NID1. Where appropriate, the term "affinity molecules" shall be construed to embrace immunoaffinity molecules and other substances capable of specific binding to NID1 including but not limited to ligands, lectins, streptavidins, antibody mimetics and synthetic binding agents.

5.3.1 Production of Antibodies to NID1

According to the disclosure NID1, a NID1 analog, a NID1-related protein or a fragment or derivative of any of the foregoing may be used as an immunogen to generate antibodies which immunospecifically bind such an immunogen. Such immunogens can be isolated by any convenient means, including the methods described above. The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3.sup.rd Edition, W. E. Paul, ed., Raven Press, N.Y. (1993); Wilson (1994) J. Immunol. Methods 175:267-273; Yarmush (1992) J. Biochem. Biophys. Methods 25:85-97. The term antibody includes antigen-binding portions, i.e., "antigen binding sites" (e.g. fragments, subsequences, complementarity determining regions (CDRs)) that retain capacity to bind antigen, including (i) a Fab fragment, a monovalent fragment consisting of the VL, VH, CL and CH1 domains; (ii) a F(ab').sub.2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody". Antibodies of the disclosure include, but are not limited to polyclonal, monoclonal, bispecific, humanized or chimeric antibodies, single chain antibodies, Fab fragments and F(ab')$_2$ fragments, fragments produced by a Fab expression library, anti-idiotypic(anti-Id) antibodies, and epitope-binding fragments of any of the above. The immunoglobulin molecules of the disclosure can be of any class (e.g. IgG, IgE, IgM, IgD and IgA such as IgG) or subclass of immunoglobulin molecule.

The term "specifically binds" or "binds specifically" (or "immunospecifically binds") is not intended to indicate that an antibody binds exclusively to its intended target. Rather, an antibody "specifically binds" if its affinity for its intended target is typically about 5-fold greater when compared to its affinity for a non-target molecule. Suitably there is no significant cross-reaction or cross-binding with undesired substances, especially naturally occurring proteins or tissues of a healthy person or animal. Preferably the affinity of the antibody will be at least about 5 fold, preferably 10 fold, more preferably 25-fold, even more preferably 50-fold, and most preferably 100-fold or more, greater for a target molecule than its affinity for a non-target molecule. In some embodiments, specific binding between an antibody or other binding agent and an antigen means a binding affinity of about $10^{-6}M$-$10^{-7}M$, $10^{-7}M$-$10^{-8}M$, $10^{-8}M$-$10^{-9}M$, $10^{-10}M$-$10^{-11}M$. Antibodies may, for example, bind with affinities of about $10^{-6}M$-$10^{-7}M$, $10^{-7}M$-$10^{-8}M$, $10^{-8}M$-$10^{-9}M$, $10^{-10}M$-$10^{-11}M$.

Affinity is calculated as $K_d = k_{off}/k_{on}$ ($k_{off}$ is the dissociation rate constant, $k_{on}$ is the association rate constant and $K_d$ is the equilibrium constant. Affinity can be determined at equilibrium by measuring the fraction bound (r) of labelled ligand at various concentrations (c). The data are graphed using the Scatchard equation: $r/c = K(n-r)$: where r=moles of bound ligand/mole of receptor at equilibrium; c=free ligand concentration at equilibrium; K=equilibrium association constant; and n=number of ligand binding sites per receptor molecule. Antibody affinity measurement by Scatchard analysis is well known in the art, see, e.g. van Erp et al., J. Immunoassay 12: 425-43, 1991; Nelson and Griswold, Comput. Methods Programs Biomed. 27: 65-8, 1988.

In one embodiment, any publicly available antibodies that recognize gene products of genes encoding NID1 may be used. In another embodiment, methods known to those skilled in the art are used to produce antibodies that recognize NID1, a NID1 analog, a NID1-related polypeptide, or a fragment or derivative of any of the foregoing. One skilled in the art will recognize that many procedures are available for the production of antibodies, for example, as described in Antibodies, A Laboratory Manual, Ed Harlow and David Lane, Cold Spring Harbor Laboratory (1988), Cold Spring Harbor, N.Y. One skilled in the art will also appreciate that binding fragments or Fab fragments which mimic antibodies can also be prepared from genetic information by various procedures (Antibody Engineering: A Practical Approach (Borrebaeck, C., ed.), 1995, Oxford University Press, Oxford; J. Immunol. 149, 3914-3920 (1992)).

In one embodiment, antibodies to a specific domain of NID1 are produced. In a specific embodiment, specific fragments of NID1 are used as immunogens for antibody production.

When producing the antibodies, screening for the desired antibody can be accomplished by techniques known in the art, e.g. ELISA (enzyme-linked immunosorbent assay). For example, to select antibodies which recognize a specific domain of NID1, one may assay generated hybridomas for a product which binds to a NID1 fragment containing such domain. For selection of an antibody that specifically binds a first NID1 homolog but which does not specifically bind to (or binds less avidly to) a second NID1 homolog, one can select on the basis of positive binding to the first NID1 homolog and a lack of binding to (or reduced binding to) the second NID1 homolog. Similarly, for selection of an antibody that specifically binds NID1 but which does not specifically bind to (or binds less avidly to) a different isoform of the same protein (such as a different glycoform having the same core peptide as NID1), one can select on the basis of positive binding to NID1 and a lack of binding to (or reduced binding to) the different isoform (e.g. a different glycoform). Thus, the present disclosure provides an antibody (such as a monoclonal antibody) that binds with greater affinity (for example at least 2-fold, such as at least 5-fold, particularly at least 10-fold greater affinity) to NID1 than to a different isoform or isoforms of NID1.

Polyclonal antibodies which may be used in the methods of the disclosure are heterogeneous populations of antibody molecules derived from the sera of immunized animals. Unfractionated immune serum can also be used. Various procedures known in the art may be used for the production of polyclonal antibodies to NID1, a fragment of NID1, a NID1-related polypeptide, or a fragment of a NID1-related polypeptide. For example, one way is to purify polypeptides of interest or to synthesize the polypeptides of interest using, e.g. solid phase peptide synthesis methods well known in the art. See, e.g. Guide to Protein Purification, Murray P. Deutcher, ed., Meth. Enzymol. Vol 182 (1990); Solid Phase Peptide Synthesis, Greg B. Fields ed., Meth. Enzymol. Vol 289 (1997); Kiso et al., Chem. Pharm. Bull. (Tokyo) 38: 1192-99, 1990; Mostafavi et al., Biomed. Pept. Proteins Nucleic Acids 1: 255-60, 1995; Fujiwara et al., Chem. Pharm. Bull. (Tokyo) 44: 1326-31, 1996. The selected polypeptides may then be used to immunize by injection various host animals, including but not limited to rabbits, mice, rats, etc., to generate polyclonal or monoclonal antibodies. If NID1 is purified by gel electrophoresis, NID1 can be used for immunization with or without prior extraction from the polyacrylamide gel. Various adjuvants (i.e. immunostimulants) may be used to enhance the immunological response, depending on the host species, including, but not limited to, complete or incomplete Freund's adjuvant, a mineral gel such as aluminum hydroxide, surface active substance such as lysolecithin, pluronic polyol, a polyanion, a peptide, an oil emulsion, keyhole limpet hemocyanin, dinitrophenol, and an adjuvant such as BCG (bacille Calmette-Guerin) or corynebacterium parvum. Additional adjuvants are also well known in the art.

For preparation of monoclonal antibodies (mAbs) directed toward NID1, a fragment of NID1, a NID1-related polypeptide, or a fragment of a NID1-related polypeptide, any technique which provides for the production of antibody molecules by continuous cell lines in culture may be used. For example, the hybridoma technique originally developed by Kohler and Milstein (1975, Nature 256:495-497), as well as the trioma technique, the human B-cell hybridoma technique (Kozbor et al., 1983, Immunology Today 4:72), and the EBV-hybridoma technique to produce human monoclonal antibodies (Cole et al., 1985, in Monoclonal Antibodies and Cancer Therapy, Alan R. Liss, Inc., pp. 77-96). Such antibodies may be of any immunoglobulin class including IgG, IgM, IgE, IgA, IgD and any subclass thereof. The hybridoma producing the mAbs of the disclosure may be cultivated in vitro or in vivo. In an additional embodiment of the disclosure, monoclonal antibodies can be produced in germ-free animals utilizing known technology (PCT/US90/02545, incorporated herein by reference).

The monoclonal antibodies include but are not limited to human monoclonal antibodies and chimeric monoclonal antibodies (e.g. human-mouse chimeras). A chimeric antibody is a molecule in which different portions are derived from different animal species, such as those having a human immunoglobulin constant region and a variable region derived from a murine mAb, (see, e.g. Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarity determining regions (CDRs) from the non-human species and a framework region from a human immunoglobulin molecule, (see, e.g. Queen, U.S. Pat. No. 5,585,089, which is incorporated herein by reference in its entirety.)

Chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125, 023; Better et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Canc. Res. 47:999-1005; Wood et al., 1985, Nature 314: 446-449; and Shaw et al., 1988, J. Natl. Cancer Inst. 80:1553-1559; Morrison, 1985, Science 229:1202-1207; Oi et al., 1986, BioTechniques 4:214; U.S. Pat. No. 5,225,539; Jones et al., 1986, Nature 321:552-525; Verhoeyan et al. (1988) Science 239:1534; and Beidler et al., 1988, J. Immunol. 141:4053-4060.

Completely human antibodies are particularly desirable for therapeutic treatment of human subjects. Such antibodies can be produced using transgenic mice which are incapable of expressing endogenous immunoglobulin heavy and light chain genes, but which can express human heavy and light chain genes. The transgenic mice are immunized in the normal fashion with a selected antigen, e.g. all or a portion of NID1. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g. U.S. Pat. Nos. 5,625,126; 5,633,425; 5,569,825; 5,661,016; and 5,545,806.

Completely human antibodies which recognize a selected epitope can be generated using a technique referred to as "guided selection". In this approach a selected non-human monoclonal antibody, e.g. a mouse antibody, is used to guide the selection of a completely human antibody recognizing the same epitope. (Jespers et al., (1994) BioTechnology 12:899-903).

Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988).

The disclosure further provides for the use of bispecific antibodies, which can be made by methods known in the art. Traditional production of full-length bispecific antibodies is based on the coexpression of two immunoglobulin heavy chain-light chain pairs, where the two chains have different specificities (Milstein et al., 1983, Nature 305:537-539). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, published 13 May 1993, and in Traunecker et al., 1991, EMBO J. 10:3655-3659.

The disclosure provides functionally active fragments, derivatives or analogs of the anti-NID1 immunoglobulin molecules. Functionally active means that the fragment, derivative or analog is able to elicit anti-anti-idiotype antibodies (i.e., tertiary antibodies) that recognize the same antigen that is recognized by the antibody from which the fragment, derivative or analog is derived. Specifically, in a preferred embodiment the antigenicity of the idiotype of the immunoglobulin molecule may be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art.

The present disclosure provides antibody fragments such as, but not limited to, F(ab')$_2$ fragments and Fab fragments. Antibody fragments which recognize specific epitopes may be generated by known techniques. F(ab')$_2$ fragments consist of the variable region, the light chain constant region and the CH1 domain of the heavy chain and are generated by pepsin digestion of the antibody molecule. Fab fragments are generated by reducing the disulfide bridges of the F(ab')$_2$ fragments. The disclosure also provides heavy chain and light chain dimers of the antibodies of the disclosure, or any minimal fragment thereof such as Fvs or single chain antibodies (SCAs) (e.g. as described in U.S. Pat. No. 4,946,778; Bird, 1988, Science 242:423-42; Huston et al., 1988, Proc. Natl. Acad. Sci. USA 85:5879-5883; and Ward et al., 1989, Nature 334:544-54), or any other molecule with the same specificity as the antibody of the disclosure. Single chain antibodies are formed by linking the heavy and light chain fragments of the Fv region via an amino acid bridge, resulting in a single chain polypeptide. Techniques for the assembly of functional Fv fragments in *E. coli* may be used (Skerra et al., 1988, Science 242:1038-1041).

In other embodiments, the disclosure provides fusion proteins of the immunoglobulins of the disclosure (or functionally active fragments thereof), for example in which the immunoglobulin is fused via a covalent bond (e.g. a peptide bond), at either the N-terminus or the C-terminus to an amino acid sequence of another protein (or portion thereof, preferably at least 10, 20 or 50 amino acid portion of the protein) that is not the immunoglobulin. Preferably the immunoglobulin, or fragment thereof, is covalently linked to the other protein at the N-terminus of the constant domain. As stated above, such fusion proteins may facilitate purification, increase half-life in vivo, and enhance the delivery of an antigen across an epithelial barrier to the immune system.

The immunoglobulins include analogs and derivatives that are modified, i.e., by the covalent attachment of any type of molecule as long as such covalent attachment does not impair immunospecific binding. For example, but not by way of limitation, the derivatives and analogs of the immunoglobulins include those that have been further modified, e.g. by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, etc. Additionally, the analog or derivative may contain one or more non-classical amino acids.

The foregoing antibodies can be used in methods known in the art relating to the localization and activity of NID1, e.g. for imaging this protein, measuring levels thereof in appropriate physiological samples, in diagnostic methods, etc.

5.3.2 Expression of Antibodies

The antibodies of the disclosure can be produced by any method known in the art for the synthesis of antibodies, in particular, by chemical synthesis or by recombinant expression, and are preferably produced by recombinant expression techniques.

In one embodiment, recombinant expression of antibodies, or fragments, derivatives or analogs thereof, requires construction of a nucleic acid that encodes the antibody. If the nucleotide sequence of the antibody is known, a nucleic acid encoding the antibody may be assembled from chemically synthesized oligonucleotides (e.g. as described in Kutmeier et al., 1994, BioTechniques 17:242), which, briefly, involves the synthesis of overlapping oligonucleotides containing portions of the sequence encoding antibody, annealing and ligation of those oligonucleotides, and then amplification of the ligated oligonucleotides by PCR.

The antibodies that are generated by these methods may then be selected by first screening for affinity and specificity with the purified polypeptide of interest and, if required, comparing the results to the affinity and specificity of the antibodies with polypeptides that are desired to be excluded from binding. The screening procedure can involve immobilization of the purified polypeptides in separate wells of microtiter plates. The solution containing a potential antibody or groups of antibodies is then placed into the respective microtiter wells and incubated for about 30 min to 2 h. The microtiter wells are then washed and a labelled secondary antibody (for example, an anti-mouse antibody conjugated to alkaline phosphatase if the raised antibodies are mouse antibodies) is added to the wells and incubated for about 30 min and then washed. Substrate is added to the wells and a color reaction will appear where antibody to the immobilized polypeptide(s) is present.

The antibodies so identified may then be further analyzed for affinity and specificity in the assay design selected. In the development of immunoassays for a target protein, the purified target protein acts as a standard with which to judge the sensitivity and specificity of the immunoassay using the antibodies that have been selected. Because the binding affinity of various antibodies may differ; certain antibody pairs (e.g. in sandwich assays) may interfere with one another sterically, etc., assay performance of an antibody may be a more important measure than absolute affinity and specificity of an antibody.

Those skilled in the art will recognize that many approaches can be taken in producing antibodies or binding fragments and screening and selecting for affinity and specificity for the various polypeptides.

For therapeutic applications, antibodies (particularly monoclonal antibodies) may suitably be human or humanized animal (e.g. mouse) antibodies. Animal antibodies may be raised in animals using the human protein (e.g. NID1) as immunogen. Humanization typically involves grafting CDRs identified thereby into human framework regions. Normally some subsequent retromutation to optimize the conformation of chains is required. Such processes are known to persons skilled in the art.

5.3.3 Affinity Molecule Modifications

In a preferred embodiment, anti-NID1 molecules such as antibodies or fragments thereof are conjugated to a diagnostic moiety (such as a detectable label) or a therapeutic moiety. The antibodies can be used for diagnosis or to determine the efficacy of a given treatment regimen. Detection can be facilitated by coupling the antibody to a detectable substance (label). Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics according to the present disclosure. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc, $^{68}$Ga may also be employed.

As indicated above affinity molecules, such as antibodies for use in the disclosure, may be conjugated to a therapeutic moiety, such as a cytotoxin, a drug (e.g. an immunosuppressant) or a radiotoxin. Such conjugates are referred to herein as "immunoconjugates". Immunoconjugates that include one or more cytotoxins are referred to as "immunotoxins". A cytotoxin or cytotoxic agent includes any agent that is detrimental to (e.g. kills) cells. Examples include taxol, cytochalasin B, gramicidin D, ethidium bromide, emetine, mitomycin, etoposide, tenoposide, vincristine, vinblastine, 41umanized41, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g. methotrexate, 6-mercaptopurine, 6-thioguanine, cytarabine, 5-fluorouracil 41umanized41e), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, and anthramycin (AMC)), and anti-mitotic agents (e.g. vincristine and vinblastine). Other examples of therapeutic cytotoxins that can be conjugated to an antibody of the disclosure include duocarmycins, calicheamicins, maytansines and auristatins, and derivatives thereof. An example of a calicheamicin antibody conjugate is commercially available (Mylotarg®; American Home Products).

Cytotoxins can be conjugated to antibodies of the disclosure using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g. cathepsins B, C, D).

Examples of cytotoxins are described, for example, in U.S. Pat. Nos. 6,989,452, 7,087,600, and 7,129,261, and in PCT Application Nos. PCT/US2002/17210, PCT/U52005/017804, PCT/US2006/37793, PCT/U52006/060050, PCT/U52006/060711, WO2006/110476, and in U.S. Patent Application No. 60/891,028, all of which are incorporated herein by reference in their entirety. For further discussion of types of cytotoxins, linkers and methods for conjugating therapeutic agents to antibodies, see also Saito, G. et al. (2003) Adv. Drug Deliv. Rev. 55:199-215; Trail, P. A. et al. (2003) Cancer Immunol. Immunother. 52:328-337; Payne, G. (2003) Cancer Cell 3:207-212; Allen, T. M. (2002) Nat. Rev. Cancer 2:750-763; Pastan, I. and Kreitman, R. J. (2002) Curr. Opin. Investig. Drugs 3:1089-1091; Senter, P. D. and Springer, C. J. (2001) Adv. Drug Deliv. Rev. 53:247-264.

Affinity molecules can also be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine131, indium111, yttrium90 and lutetium177. Methods for preparing radioimmunoconjugates are established in the art. Examples of radioimmunoconjugates are commercially available, including Zevalin® (IDEC Pharmaceuticals) and Bexxar.RTM. (Corixa Pharmaceuticals), and similar methods can be used to prepare radioimmunoconjugates using the antibodies of the disclosure.

The disclosure also provides for fully human, or 42umanized antibodies that induce antibody-directed cell-mediated cytotoxicity (ADCC). A fully human antibody is one in which the protein sequences are encoded by naturally occurring human immunoglobulin sequences, either from isolated antibody-producing human B-lymphocytes, or from transgenic murine B-lymphocytes of mice in which the murine immunoglobulin coding chromosomal regions have been replaced by orthologous human sequences. Transgenic antibodies of the latter type include, but are not restricted to, HuMab (Medarex, Inc, CA) and XenoMouse (Abgenix Inc., CA). A 42umanized antibody is one in which the constant region of a non-human antibody molecule of appropriate antigen specificity, is replaced by the constant region of a human antibody, preferably of the IgG subtype, with appropriate effector functions (Morrison et al., 1984, Proc. Natl. Acad. Sci. 81:851-855; Neuberger et al., 1984, Nature 312:604-608; Takeda et al., 1985, Nature 314:452-454). Appropriate effector functions include ADCC, which is a natural process by which fully-human antibodies or humanized antibodies, when bound to targets on the surface of cancer cells, switch on the cell killing properties of lymphocytes that are part of the normal immune system. These active lymphocytes, called Natural Killer (NK) cells, use a cytotoxic process to destroy living cells to which the antibodies are bound. ADCC activity may be detected and quantified by measuring release of Europium (Eu.sup.3+) from Eu.sup.3+labelled, living cells in the presence of an antigen-specific antibody and peripheral blood mononuclear cells extracted from an immunocompetent, living human subject. The ADCC process is described in detail in Janeway Jr. C. A. et al., Immunobiology, 5$^{th}$ ed., 2001, Garland Publishing, ISBN 0-8153-3642-X; Pier G. B. et al., Immunology, Infection, and Immunity, 2004, p 246-5; Albanell J. et al., Advances in Experimental Medicine and Biology, 2003, 532:p2153-68 and Weng, W.-K. et al., Journal of Clinical Oncology, 2003, 21:p 3940-3947. Suitable methods for the detection and quantification of ADCC can be found in Blomberg et al., Journal of Immunological Methods. 1986, 86:p 225-9; Blomberg et al., Journal of Immunological Methods. 1986, 21; 92:p 117-23 and Patel & Boyd, Journal of Immunological Methods. 1995, 184:p 29-38.

5.4 Diagnosis of Cancer

According to another aspect of the disclosure, there is provided a method of detecting, diagnosing and/or screening for or monitoring the progression of cancer e.g. the disease or disorder or of monitoring the effect of e.g. an anti-cancer drug or therapy directed towards the disease or disorder in a subject which comprises detecting the presence or level of antibodies capable of immunospecific binding to NID1, or one or more epitope-containing fragments thereof or which comprises detecting a change in the level thereof in said subject.

According to another aspect of the disclosure there is also provided a method of detecting, diagnosing and/or screening for cancer e.g. the disease or disorder in a subject which comprises detecting the presence of antibodies capable of immunospecific binding to NID1, or one or more epitope-containing fragments thereof in said subject, in which (a) the presence of an elevated level of antibodies capable of immunospecific binding to NID1 or said one or more epitope-containing fragments thereof in said subject as compared with the level in a healthy subject or (b) the presence of a detectable level of antibodies capable of immunospecific binding to NID1 or said one or more epitope-containing fragments thereof in said subject as compared with a corresponding undetectable level in a healthy subject indicates the presence of said cancer in said subject.

One particular method of detecting, diagnosing and/or screening for cancer, e.g. the disease or disorder comprises: bringing into contact with a biological sample to be tested NID1, or one or more epitope-containing fragments thereof; and detecting the presence of antibodies in the subject capable of immunospecific binding to NID1, or one or more epitope-containing fragments thereof.

According to another aspect of the disclosure there is provided a method of monitoring the progression of cancer, e.g. the disease or disorder or of monitoring the effect of e.g. an anti-cancer drug or therapy directed towards the disease or disorder in a subject which comprises detecting the presence of antibodies capable of immunospecific binding to NID1, or one or more epitope-containing fragments thereof in said subject at a first time point and at a later time point, the presence of an elevated or lowered level of antibodies capable of immunospecific binding to NID1, or one or more epitope-containing fragments thereof in said subject at the later time point as compared with the level in said subject at said first time point, indicating the progression or regression of said cancer, or the effect or non-effect of said anti-cancer drug or therapy in said subject.

The presence of antibodies capable of immunospecific binding to NID1, or one or more epitope-containing fragments thereof is typically detected by analysis of a biological sample obtained from said subject (exemplary biological samples are mentioned above, e.g. the sample is a sample of lung, pancreas and skin tissue, or else a sample of blood or saliva). The method typically includes the step of obtaining said biological sample for analysis from said subject. The antibodies that may be detected include IgA, IgM and IgG antibodies.

In accordance with the present disclosure, test samples of e.g. lung, serum, plasma or urine obtained from a subject suspected of having or known to have the disease or disorder can be used for diagnosis or monitoring. In one embodiment, a change in the abundance of NID1 in a test sample relative to a control sample (from a subject or subjects free from the disease or disorder) or a previously determined reference range indicates the presence of the disease or disorder. In another embodiment, the relative abundance of NID1 in a test sample compared to a control sample or a previously determined reference range indicates a subtype of the disease or disorder (e.g. small cell carcinoma; squamous cell lung carcinoma; endocrine tumors of the lung or squamous cell). In yet another embodiment, the relative abundance of NID1 in a test sample relative to a control sample or a previously determined reference range indicates the degree or severity of the disease or disorder (e.g. metastasis or the extent of metastasis to various organs). In any of the aforesaid methods, detection of NID1 may optionally be combined with detection of one or more of additional biomarkers for the disease or disorder. Any suitable method in the art can be employed to measure the level of NID1, including but not limited to kinase assays, immunoassays to detect and/or visualize the NID1 (e.g. Western blot, immunoprecipitation followed by sodium dodecyl sulfate polyacrylamide gel electrophoresis, immunocytochemistry, etc.). In a further embodiment, a change in the abundance of mRNA encoding NID1 in a test sample relative to a control sample or a previously determined reference range indicates the presence of the disease or disorder. Any suitable hybridization assay can be used to detect NID1 expression by detecting and/or visualizing mRNA encoding the NID1 (e.g. Northern assays, dot blots, in situ hybridization, etc.).

In another embodiment of the disclosure, labelled antibodies (or other affinity molecules), derivatives and analogs thereof, which specifically bind to NID1 can be used for diagnostic purposes to detect, diagnose, or monitor the disease or disorder. Preferably, the disease or disorder are detected in an animal, more preferably in a mammal and most preferably in a human.

5.5 Screening Assays

The disclosure provides methods for identifying agents (e.g. candidate compounds or test compounds) that bind to NID1 or have a stimulatory or inhibitory effect on the expression or activity of NID1. The disclosure also provides methods of identifying agents, candidate compounds or test compounds that bind to a NID1-related polypeptide or a NID1 fusion protein or have a stimulatory or inhibitory effect on the expression or activity of a NID1-related polypeptide or a NID1 fusion protein. Examples of agents, candidate compounds or test compounds include, but are not limited to, nucleic acids (e.g. DNA and RNA), carbohydrates, lipids, proteins, peptides, peptidomimetics, small molecules and other drugs. Agents can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, 1997, Anticancer Drug Des. 12:145; U.S. Pat. Nos. 5,738,996; and 5,807,683, each of which is incorporated herein in its entirety by reference).

5.6 Treatment and Prevention of Disease or Disorder

The disease or disorder, for example, are treated or prevented by administration to a subject suspected of having or known to have one or more of the disease or disorder or to be at risk of developing one or more of the disease or disorder of a compound that modulates (i.e. increases or decreases) the level or activity (i.e. function) of NID1 that is differentially present in the serum or tissue of subjects having one or more of the disease or disorder compared with serum or tissue of subjects free from the disease or disorder. In one embodiment, the disease or disorder are treated or prevented by administering to a subject suspected of having or known to have one or more of the disease or disorder or to be at risk of developing the disease or disorder a compound that downregulates (i.e. decreases) the level or activity (i.e. function) of NID1 that is increased in the serum or tissue of subjects having one or more of the disease or disorder. Examples of such a compound include, but are not limited to, NID1 antisense oligonucleotides, ribozymes, antibodies (or other affinity molecules) directed against NID1, and compounds that inhibit the enzymatic activity of NID1. Other useful compounds e.g. NID1 antagonists and small molecule NID1 antagonists, can be identified using in vitro assays.

Cancer, e.g. the disease or disorder, may also be treated or prevented by administration to a subject suspected of having or known to have such cancer, or to be at risk of developing such cancer, of a compound that downregulates the level or activity (i.e. function) of NID1 that are increased in the serum or tissue of subjects having such cancer.

5.7 Vaccine Therapy

Another aspect of the disclosure is an immunogenic composition, suitably a vaccine composition, comprising NID1 or an epitope containing fragment thereof, or nucleic acid encoding NID1 or a fragment thereof optionally together with an immunostimulant.

There is also provided a method of raising an immune response which comprises administering to a subject such compositions and a method for treating or preventing cancer e.g. the disease or disorder which comprises administering to a subject in need thereof a therapeutically effective amount of such compositions and such compositions for use in preventing or treating the disease or disorder.

Thus, NID1 may be useful as antigenic material, and may be used in the production of vaccines for treatment or prophylaxis of cancer, e.g. the disease or disorder. Such material can be "antigenic" and/or "immunogenic". Generally, "antigenic" is taken to mean that the protein is capable of being used to raise antibodies (or other affinity molecules) or indeed is capable of inducing an antibody response in a subject or experimental animal "Immunogenic" is taken to mean that the protein is capable of eliciting an immune response such as a protective immune response in a subject or experimental animal. Thus, in the latter case, the protein may be capable of not only generating an antibody response but, in addition, non-antibody based immune responses "Immunogenic" also embraces whether the protein may elicit an immune-like response in an in-vitro setting e.g. a T-cell proliferation assay. The generation of an appropriate immune response may require the presence of one or more adjuvants and/or appropriate presentation of an antigen.

Vaccine compositions according to the disclosure may be either a prophylactic or therapeutic vaccine composition.

5.8 Inhibition of NID1 to Treat Disease or Disorder

In one embodiment of the disclosure, cancer, e.g. the disease or disorder is treated or prevented by administration of a compound that antagonizes (inhibits) the level and/or function of NID1 which is elevated in the serum or tissue of subjects having such cancer as compared with serum or tissue of subjects free from such cancer.

Compounds useful for this purpose include but are not limited to anti-NID1 antibodies (or other affinity molecules, and fragments and derivatives containing the binding region thereof), NID1 antisense or ribozyme nucleic acids. Other compounds that inhibit NID1 function can be identified by use of known in vitro assays, e.g. assays for the ability of a test compound to inhibit binding of NID1 to another protein or a binding partner, or to inhibit a known NID1 function.

Such inhibition may, for example, be assayed in vitro or in cell culture, but genetic assays may also be employed. They can also be used to detect levels of NID1 before and after the administration of the compound. Suitable in vitro or in vivo assays are utilized to determine the effect of a specific compound and whether its administration is indicated for treatment of the affected tissue, as described in more detail below.

In a specific embodiment, a compound that inhibits NID1 function (activity) is administered therapeutically or prophylactically to a subject in whom an increased serum or tissue level or functional activity of NID1 (e.g. greater than the normal level or desired level) is detected as compared with serum or tissue of subjects with e.g. the disease or disorder who do not receive treatment according to the disclosure or to bring the level or activity to that found in subjects free from such cancer, or a predetermined reference range. Methods standard in the art can be employed to measure the increase in NID1 level or function, as outlined above. Suitable NID1 inhibitor compositions may, for example, include small molecules, i.e. molecules of 1000 daltons or less. Such small molecules can be identified by the screening methods described herein.

5.9 Therapeutic and Prophylactic Compositions and their Use

The disclosure provides methods of treatment (and prophylaxis) comprising administering to a subject an effective amount of a compound of the disclosure (e.g. NID1 protein, an affinity molecule capable of specific binding to NID1 or a fragment thereof. or a nucleic acid encoding NID1). In a particular aspect, the compound is substantially purified (e.g. substantially free from substances that limit its effect or produce undesired side-effects).

Formulations and methods of administration that can be employed when the compound comprises a nucleic acid are described above; additional appropriate formulations and routes of administration are described below.

Various delivery systems are known and can be used to administer a compound of the disclosure, e.g. encapsulation in liposomes, microparticles, microcapsules, recombinant cells capable of expressing the compound, receptor-mediated endocytosis (see, e.g. Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g. oral mucosa, rectal and intestinal mucosa, etc.) and may be administered together with other biologically active agents. Administration can be systemic or local. In addition, it may be desirable to introduce the pharmaceutical compositions of the disclosure into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g. by use of an inhaler or nebulizer, and formulation with an aerosolizing agent.

In a specific embodiment, it may be desirable to administer the pharmaceutical compositions of the disclosure locally to the area in need of treatment; this may be achieved, for example, and not by way of limitation, by local infusion during surgery, topical application, e.g. by injection, by means of a catheter, or by means of an implant, said implant being of a porous, non-porous, or gelatinous material, including membranes, such as sikalastic membranes, or fibers. In one embodiment, administration can be by direct injection into e.g. lung, pancreas and skin tissue or at the site (or former site) of a malignant tumor or neoplastic or pre-neoplastic tissue.

In another embodiment, the compound can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In yet another embodiment, the compound can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., 1983, Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the therapeutic target, e.g. the disease or disorder thus requiring only a fraction of the systemic dose (see, e.g. Goodson, in Medical Applications of Controlled Release, supra, vol. 2, pp. 115-138 (1984)). Other controlled release systems are discussed in the review by Langer (1990, Science 249:1527-1533).

The present disclosure also provides pharmaceutical compositions. Such compositions comprise a therapeutically effective amount of a compound of the disclosure, and a pharmaceutically acceptable carrier. In a specific embodiment, the term "pharmaceutically acceptable" means suitable for approval by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatine, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, for example in purified form, together with a suitable amount of carrier so as to provide the form for proper administration to the subject. The formulation should suit the mode of administration.

In one embodiment, for example where one or more antibodies are employed, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the disclosure can be formulated as neutral or salt forms. Pharmaceutically acceptable salts, where appropriate, include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the compound of the disclosure which will be effective in the treatment of cancer, for example, the disease or disorder can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each subject's circumstances. However, suitable dosage ranges for intravenous administration are generally about 20-500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The disclosure also provides a pharmaceutical pack or kit comprising one or more containers filled with one or more of the ingredients of the pharmaceutical compositions of the disclosure. Optionally associated with such container(s) can be a notice in the form prescribed by a governmental agency regulating the manufacture, use or sale of pharmaceuticals or biological products, which notice reflects (a) approval by the agency of manufacture, use or sale for human administration, (b) directions for use, or both.

Thus, in one aspect the kit comprises the antibodies employed in the disclosure, for example the antibodies may be lyophilized for reconstitution before administration or use. Where the kit is for use in therapy/treatment such as cancer the antibody or antibodies may be reconstituted with an isotonic aqueous solution, which may optionally be provided with the kit. In one aspect the kit may comprise a polypeptide such as an immunogenic polypeptide employed in the disclosure, which may for example be lyophilized The latter kit may further comprise an adjuvant for reconstituting the immunogenic polypeptide.

In yet a further embodiment, the disclosure provides a medicament comprising, separately or together: (a) an affinity molecule which binds to NID1, and (b) an anti-cancer agent or other active agent, for simultaneous, sequential or separate administration in the treatment of cancer, preferably in the treatment of one of the disease or disorder.

5.10 Determining the Abundance of NID1 by Imaging Technology

An dvantage of determining abundance of NID1 by imaging technology may be that such a method is non-invasive (save that reagents may need to be administered) and there is no need to extract a sample from the subject.

Suitable imaging technologies include positron emission tomography (PET) and single photon emission computed tomography (SPECT). Visualization of NID1 using such techniques requires incorporation or binding of a suitable label e.g. a radiotracer such as $^{18}F$, $^{11}C$ or $^{123}I$. Radiotracers or other labels may be incorporated into NID1 by administration to the subject (e.g. by injection) of a suitably labelled specific ligand. Alternatively, they may be incorporated into a binding affinity molecule (e.g. antibody) specific for NID1 which may be administered to the subject (e.g. by injection). For discussion of use of Affibodies for imaging see e.g. Orlova A, Magnusson M, Eriksson T L, Nilsson M, Larsson B, Hoiden-Guthenberg I, Widstrom C, Carlsson J, Tolmachev V, Stahl S, Nilsson F Y, Tumor imaging using a picomolar affinity HER2 binding Affibody molecule, Cancer Res. 2006 Apr. 15; 66(8):4339-48).

5.11 Diagnosis and Treatment of Cancer Using Immunohistochemistry

Immunohistochemistry is an excellent detection technique and may therefore be very useful in the diagnosis and treatment of disease or disorder Immunohistochemistry may be used to detect, diagnose, or monitor cancers such as those mentioned above, through the localization of NID1 antigens in tissue by the use of labelled antibodies (or other affinity molecules), derivatives and analogs thereof, which specifically bind to NID1, as specific reagents through antigen-antibody interactions that are visualized by a marker such as fluorescent dye, enzyme, radioactive element or colloidal gold.

The advancement of monoclonal antibody technology has been of great significance in assuring the place of immunohistochemistry in the modern accurate microscopic diagnosis of human neoplasms. The identification of disseminated neoplastically transformed cells by immunohistochemistry allows for a clearer picture of cancer invasion and metastasis, as well as the evolution of the tumor cell associated immunophenotype towards increased malignancy. Future antineoplastic therapeutical approaches may include a variety of individualized immunotherapies, specific for the particular immunophenotypical pattern associated with each individual patient's neoplastic disease. For further discussion see e.g. Bodey B, The significance of immunohistochemistry in the diagnosis and therapy of neoplasms, Expert Opin Biol Ther. 2002 April; 2(4):371-93.

6. EXAMPLES

Figures 9A, 9B:
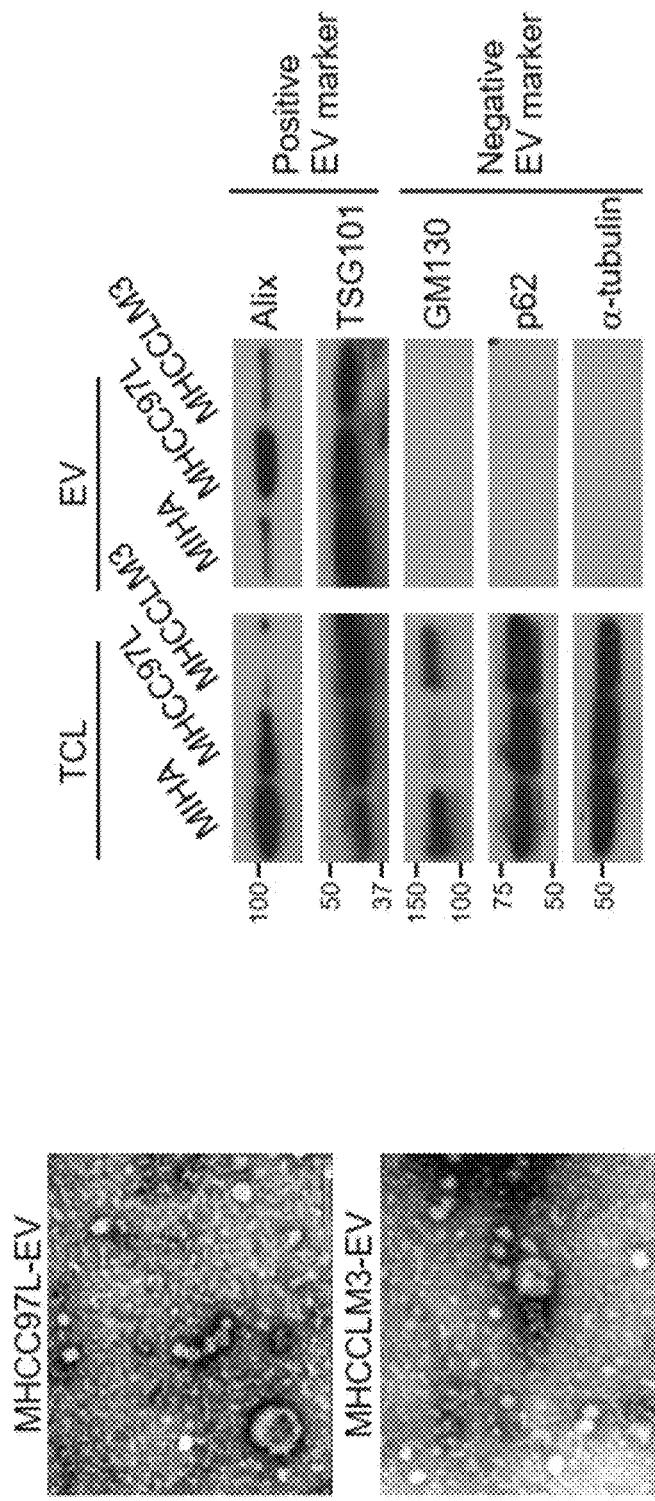
Figures 9C, 9D:
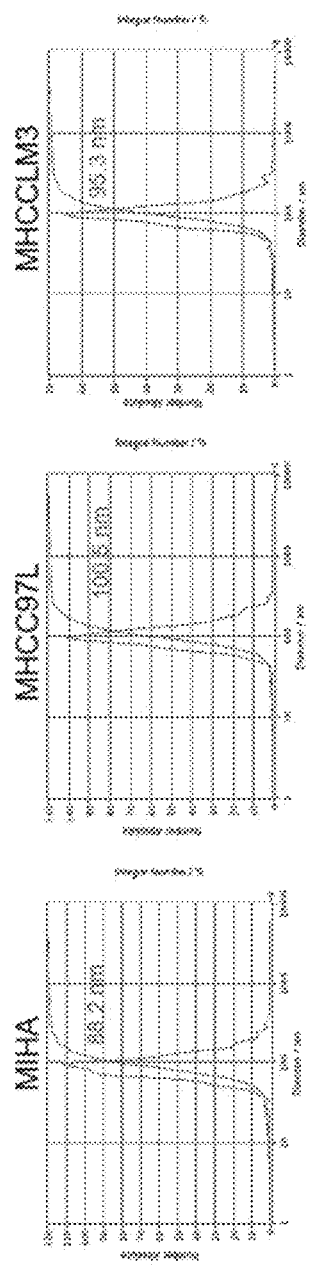

6.1 EV Secretion from Metastatic HCC Cells Promotes Liver Tumor Formation and Metastasis to the Lungs The properties of EVs derived from the metastatic HCC cell lines MHCC97L and MHCCLM3 (MHCC97L- and MHCCLM3-EVs) and their effects on target cells were investigated. Both cell lines were established from metastatic lesions of HCC patients with lung metastasis.[17] EVs from the immortalized normal liver cell line MIHA (MIHA-EVs) were included for functional comparison. The size, integrity and purity of the isolated EVs were validated (FIG. 9A, 9B, 9D). The relative amount of EV protein obtained was significantly higher in the medium of metastatic cells than in the medium of normal cells (FIG. 9C). EVs from metastatic cells significantly augmented both the migratory and invasive properties of naive LO2 liver cells and PLC/PRF/5 HCC cells (FIG. 1A). Internalization of PKH26-labeled EVs was observed in recipient cells after incubation (FIG. 10).

Using an EV education mouse model[6] comprising the repeated EV injection prior to the implantation of HCC tumor seeds in the liver (FIG. 1B), we observed that compared to mice treated with MIHA-EVs, mice administered MHCC97L-EVs showed enhanced growth of the primary tumor in the liver (FIG. 1C and 1D) and increased distant metastasis to the lungs (FIG. 1E). Tipifarnib, a farnesyl-transferase inhibitor, was identified as a potent inhibitor of EV biogenesis and secretion.[18] Tipifarnib has been shown to inhibit tumorigenesis of thyroid and breast cancers.[19, 20] In our mouse model, treatment with tipifarnib reduced EV secretion from MHCC97L cells by up to 50% (FIG. 11A). Injection of MHCC97L cells in the livers of mice pretreated with tipifarnib resulted in a significant delay in tumor development (FIG. 11B). These data suggest that EV secretion is crucial to liver tumor formation and distant metastasis.

Figure 2A:
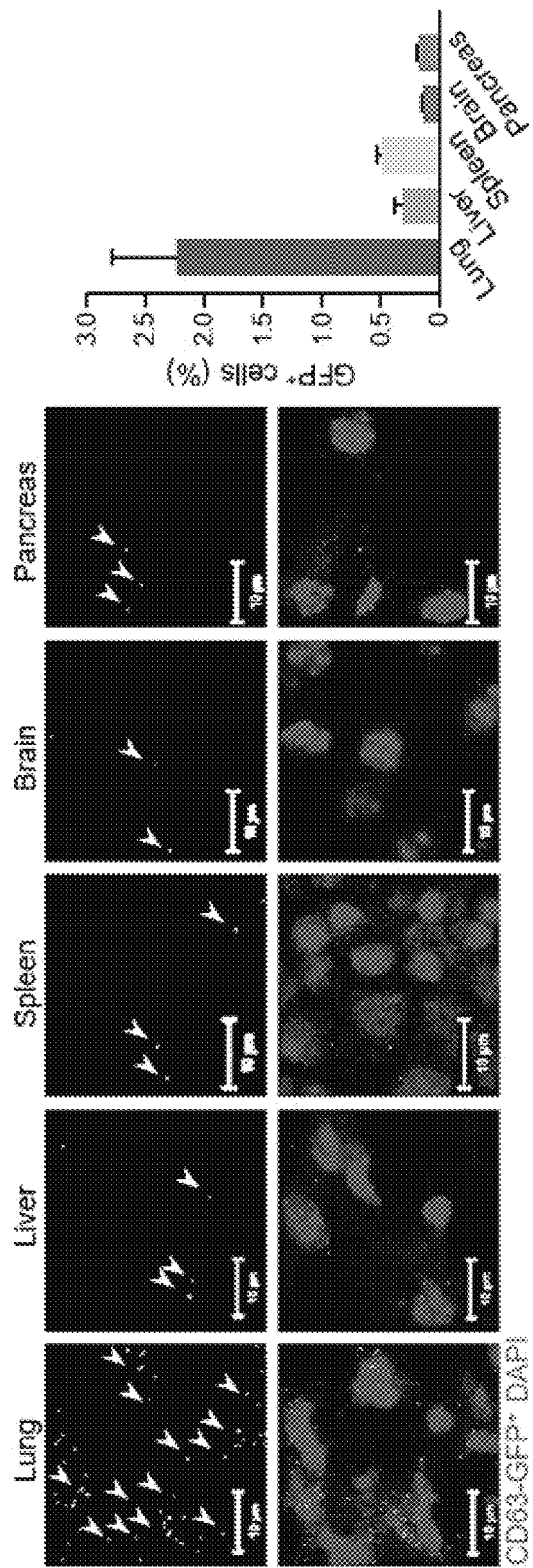
Figure 2C:
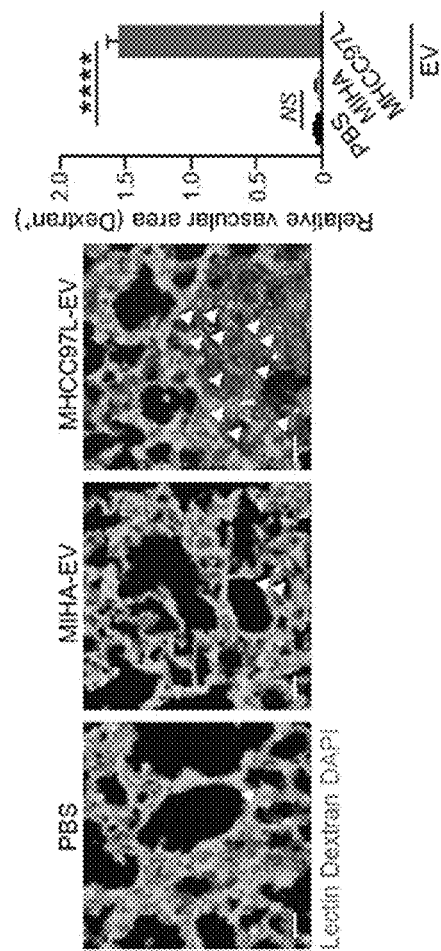
Figure 2B:
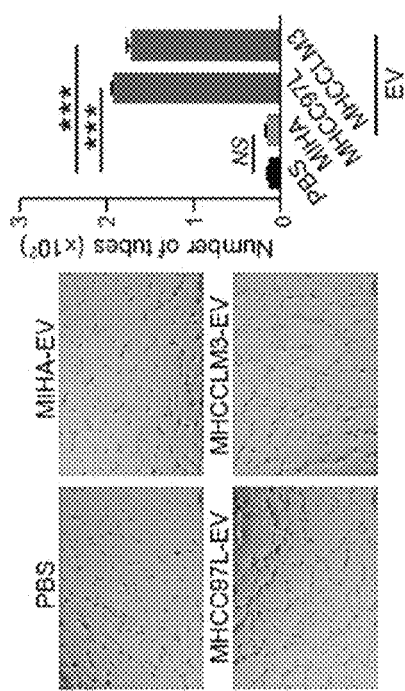
Figure 2E:
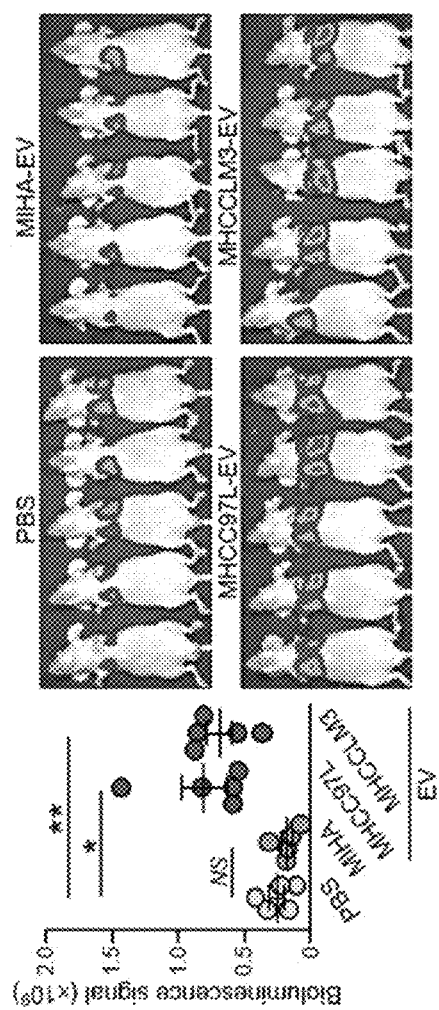
Figure 2D:
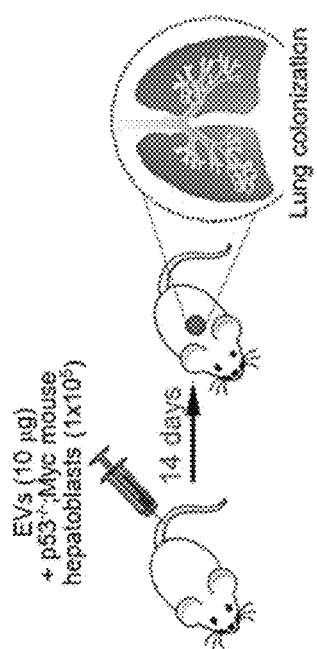
Figure 2G:
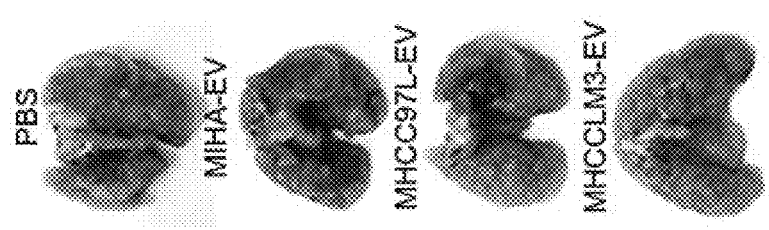
Figure 2F:
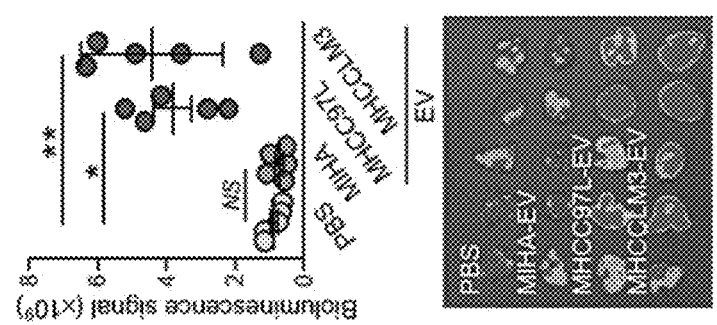
Figure 2H:
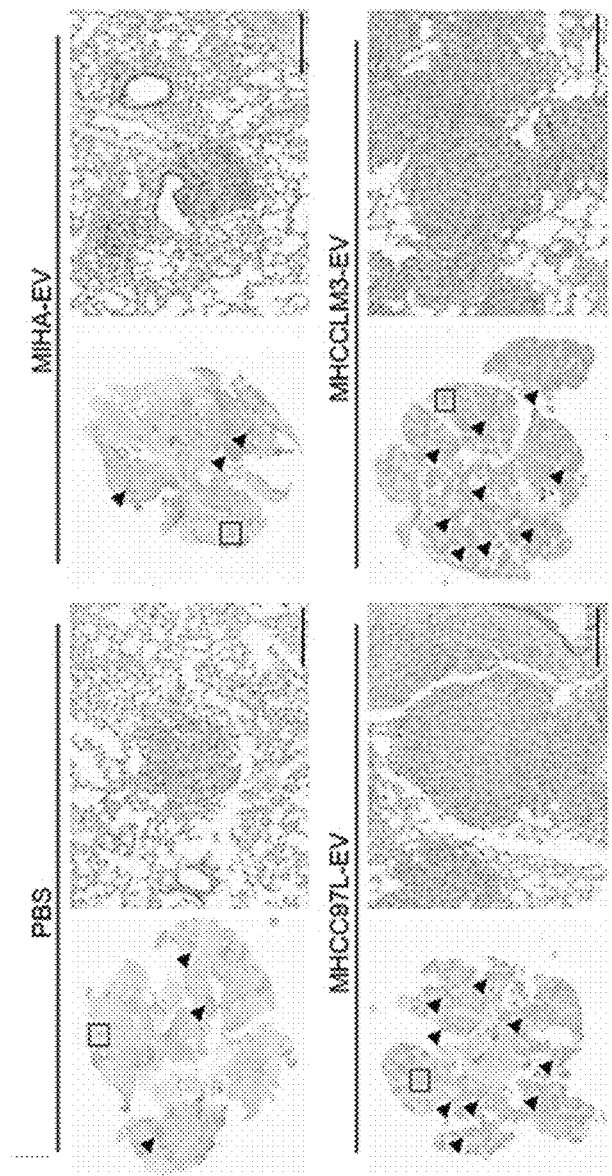

6.2 Metastatic HCC-Derived EVs Promote Angiogenesis and Facilitate the Colonization of Tumor Cells in the Lungs We further explored how EVs cultivate a supportive microenvironment to facilitate metastasis. Intravenously injected MHCC97L-derived EVs labeled with CD63-GFP or PKH67 were predominantly localized in the lungs and livers of mice (FIG. 2A; FIG. 12). Destabilization and increased permeability of the vasculature in the lungs are early events in pre-metastatic niche formation.[21] Indeed, compared to MIHA-EVs, MHCC97L- and MHCCLM3-EVs promoted HUVECs to form capillary-like structures (FIG. 2B). MHCC97L-EVs also enhanced the pulmonary endothelial permeability in mice, as indicated by the larger area of dextran staining (FIG. 2C). Coinjection of murine p53−/−; Myc-transduced hepatoblasts with MHCC97L- and MHCCLM3-EVs but not MIHA-EVs in mice resulted in enhanced colonization of hepatoblasts to lungs as revealed by the elevated bioluminescence signals and formation of tumor nodules in the lungs (FIGS. 2D-2G). Histological examination of the lungs revealed a profound increase in the number of metastatic lesions in mice injected with MHCC97L- and MHCCLM3-EVs (FIG. 2H).

Figure 3C:
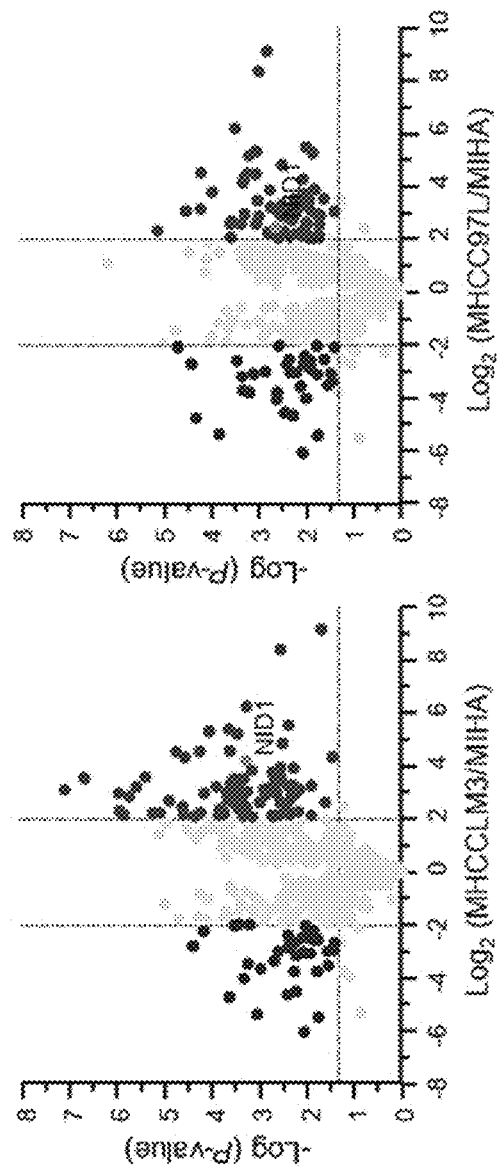
Figures 3D, 3E:
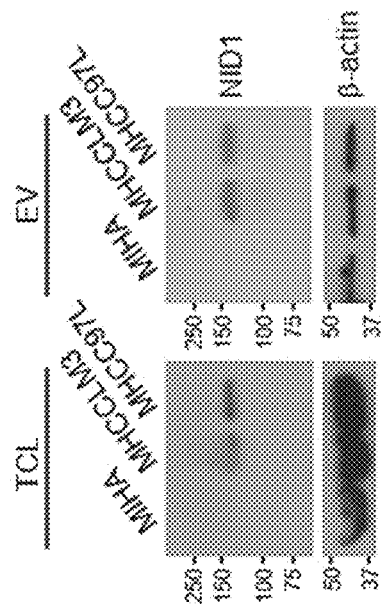
Figure 13A:
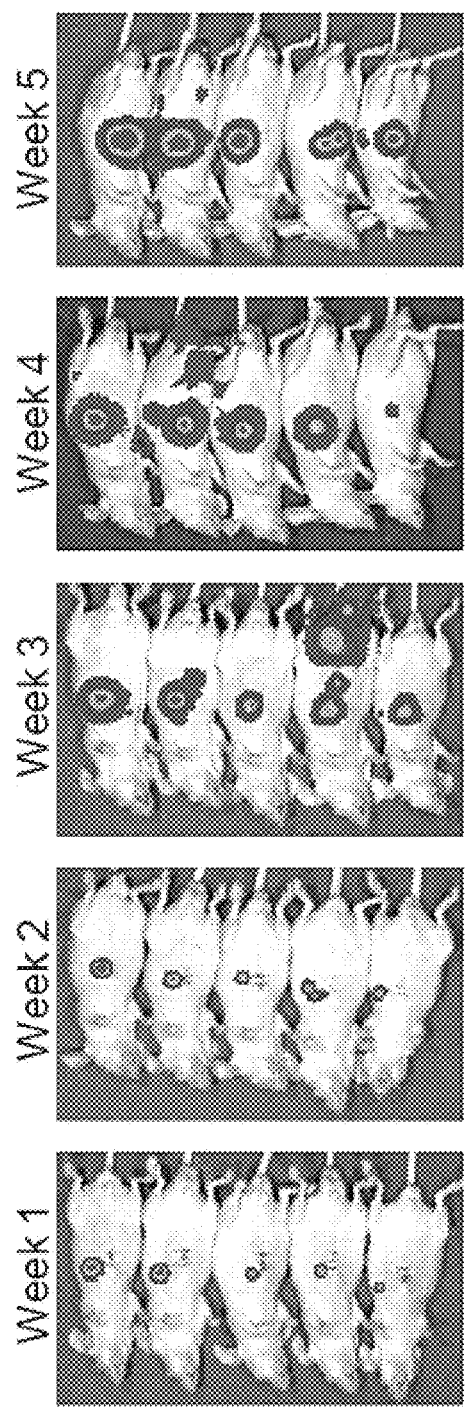
Figure 13E:
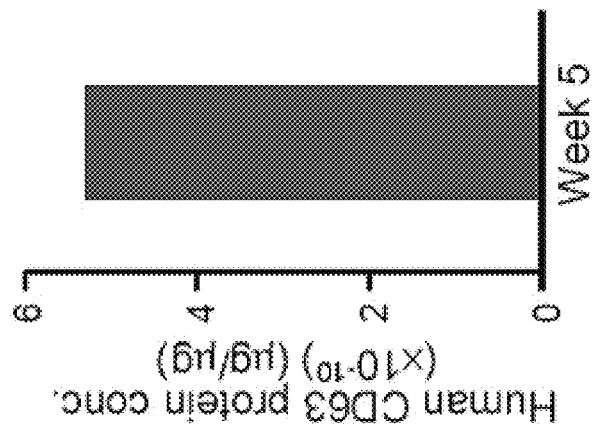
Figure 13D:
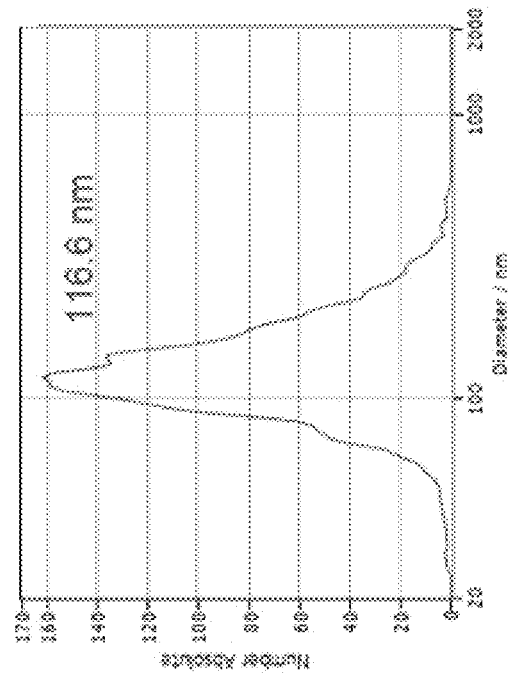

6.3 The EV-NID1 Level is Positively Correlated with the Metastatic Potential of Parental Cells To comprehensively elucidate the differential biological activity of EVs, the proteomic compositions of MIHA-, MHCC97L- and MHCCLM3-EVs were determined using mass spectrometry (FIG. 21). A total of 1040, 995 and 918 were identified in EVs of MIHA, MHCCLM3 and MHCC97L cells, respectively (FIG. 3A). Among these proteins, 611 were identified in common between EVs of 3 cell lines irrespective of their metastatic potentials. MHC-CLM3- and MHCC97L-EVs shared 807 common proteins which were 3 and 5 times, respectively, more than proteins commonly detected with MIHA-EVs. Analysis of these common proteins revealed their major cellular distribution in exosome, focal adhesion and cytosol by FunRich software (FIG. 3B). Volcano plots revealed EVs proteins of MHC-CLM3 and MHCC97L cells that were differentially expressed by at least 4-fold when compared to EVs of normal liver cells with P-value less than 0.05 (FIG. 3C). In total, 118 and 115 significantly modulated proteins were identified in MHCCLM3- and MHCC97L-EVs, respectively. Top 10 significantly upregulated EV proteins of MHCCLM3 were shown in FIG. 3D. Among which, NID1 which has accumulating evidence about its role in cancer was chosen for further investigation. NID1 is a major structural protein of the basement membrane and ECM. Its role in cancer metastasis has been described in ovarian and endometrial cancer;[22-24] however, its role in HCC remains uncertain, and the significance and existence of NID1 in EVs of HCC have never been reported. NID1 expression in total cell lysate and in EVs from MHCC97L and MHCCLM3 cells but not from MIHA cells was validated (FIG. 3E). The level of EV-NID1 also correlated well with the metastatic potential of HCC cells (FIG. 3F). In a mouse model of liver implantation of MHCC97L cells in which the development of liver tumors was monitored weekly by bioluminescence imaging (FIGS. 13A-13C), the level of NID1 in circulating EVs was higher in tumor-bearing mice than in mice prior to tumor cell inoculation and increased with the intensity of bioluminescence (FIG. 3G; FIG. 13). These findings indicate that the level of EV-NID1 reflects the metastatic ability of cells and tumor burden in mice.

Figure 4B:
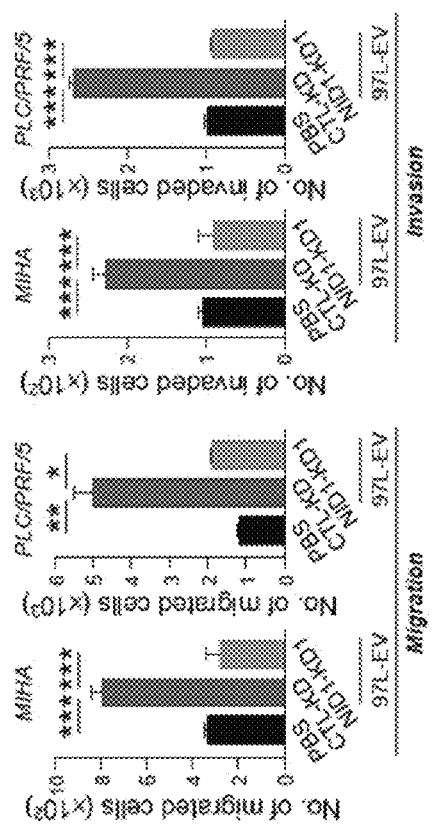
Figure 4A:
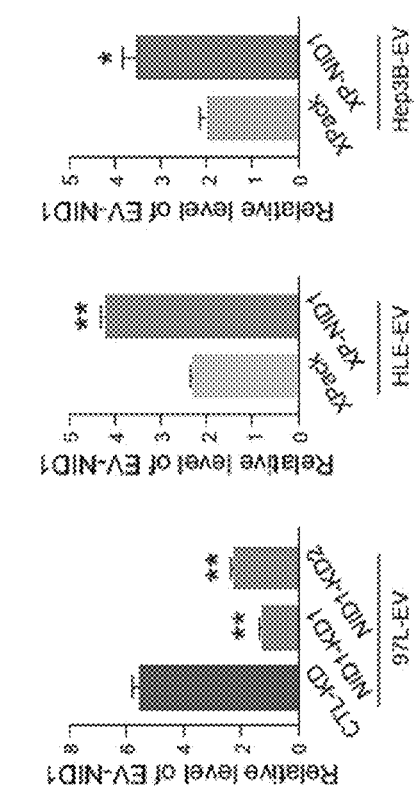
Figure 4E:
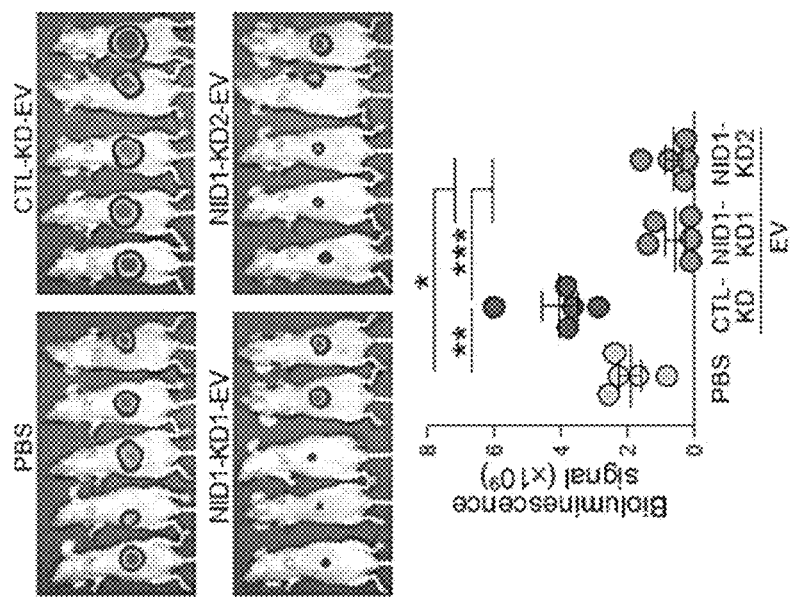
Figures 14A, 14B, 14C:
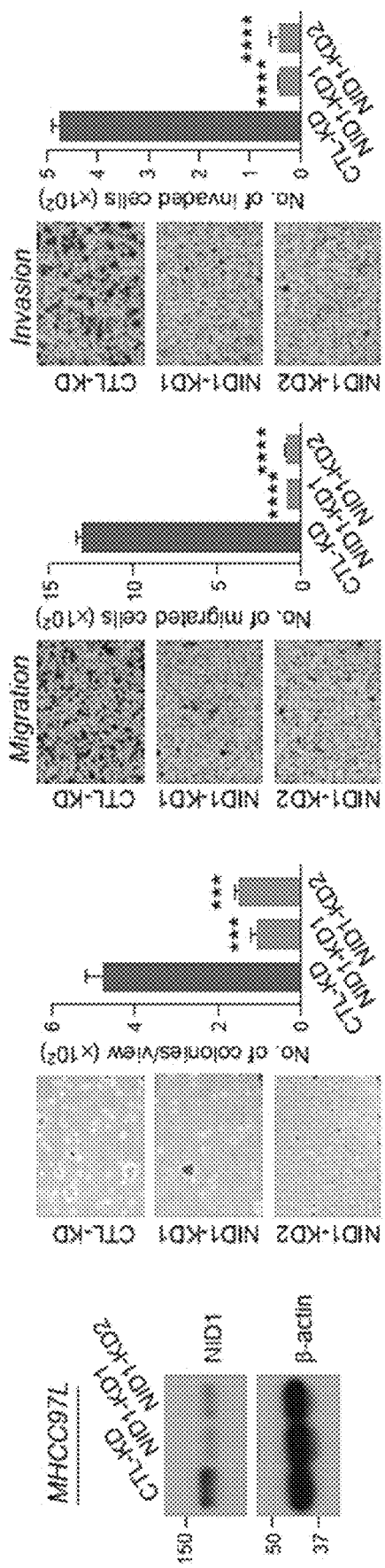
Figures 14D, 14E:
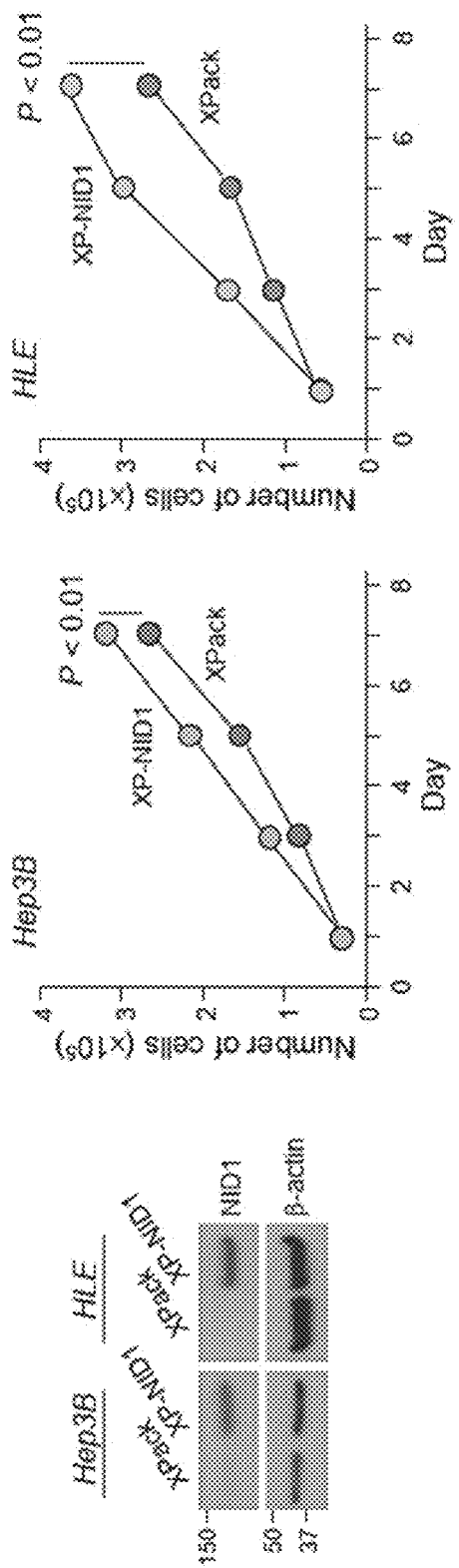
Figure 14F:
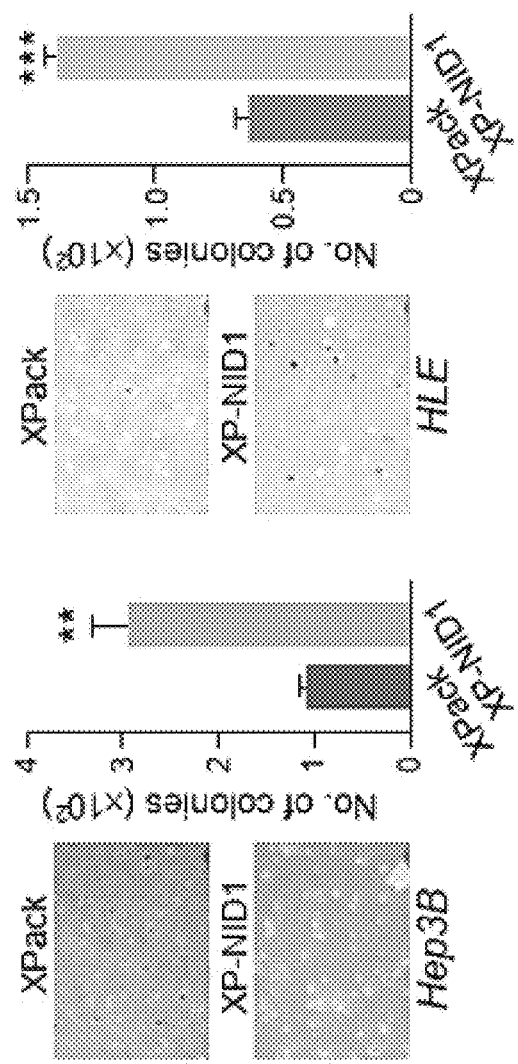
Figure 14G:
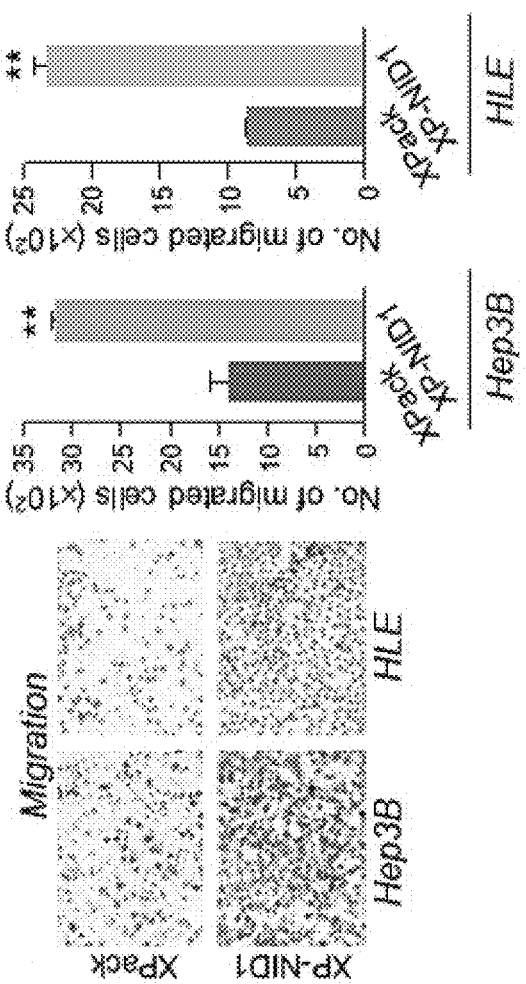
Figure 14H:
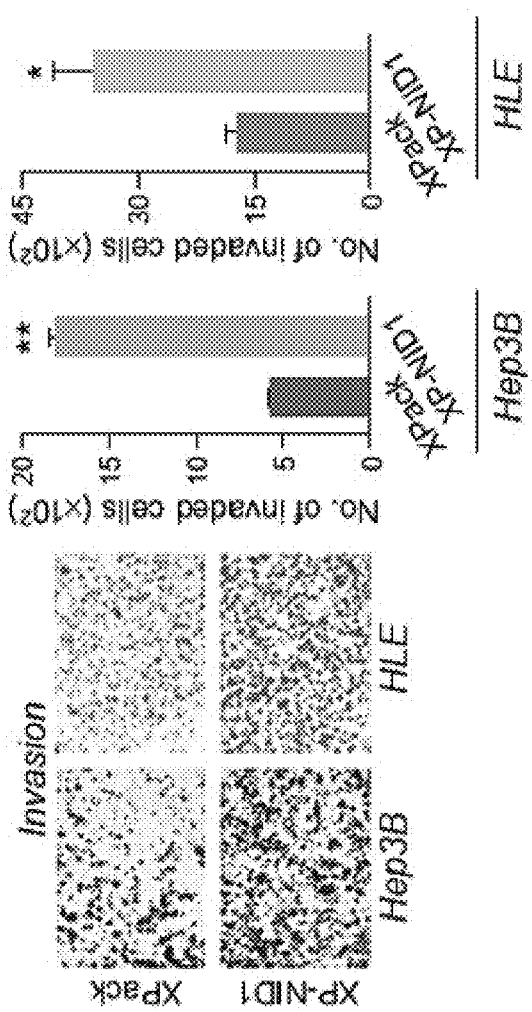
Figures 15A, 15B:
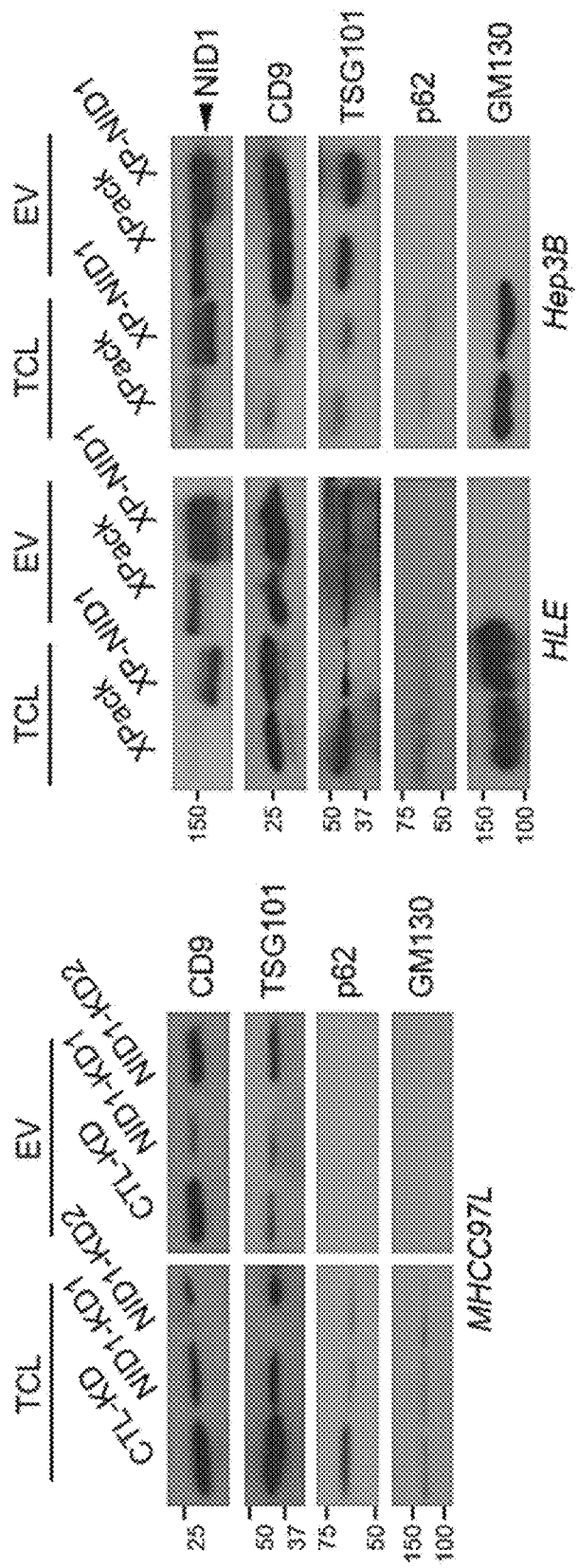
Figure 15C:
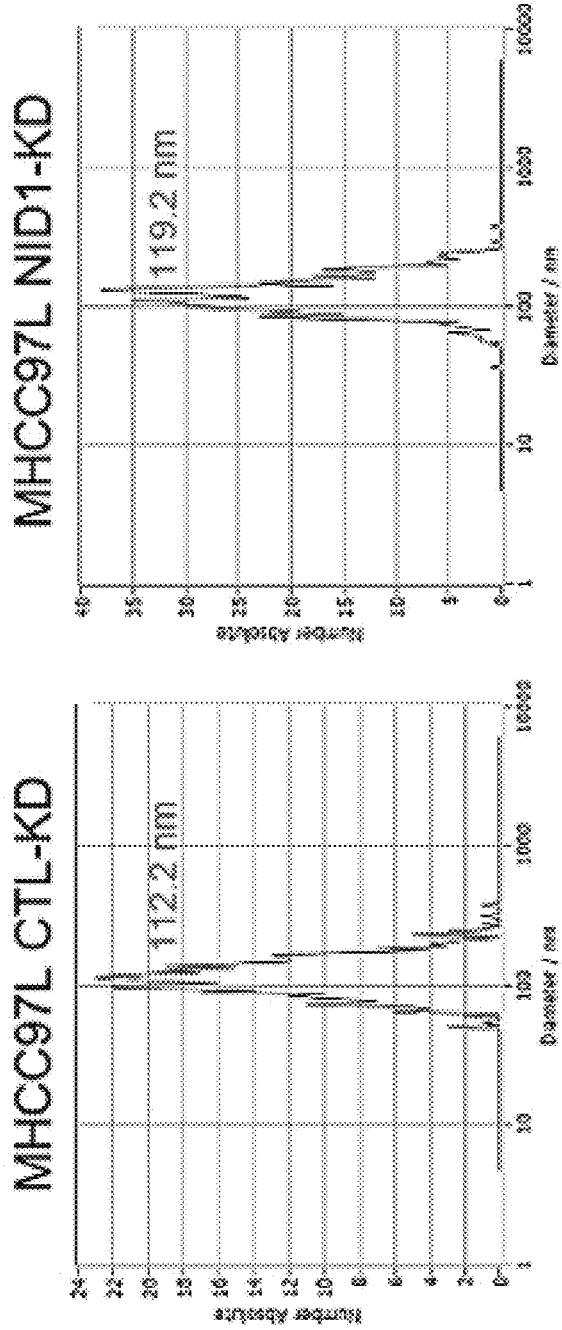
Figure 15D:
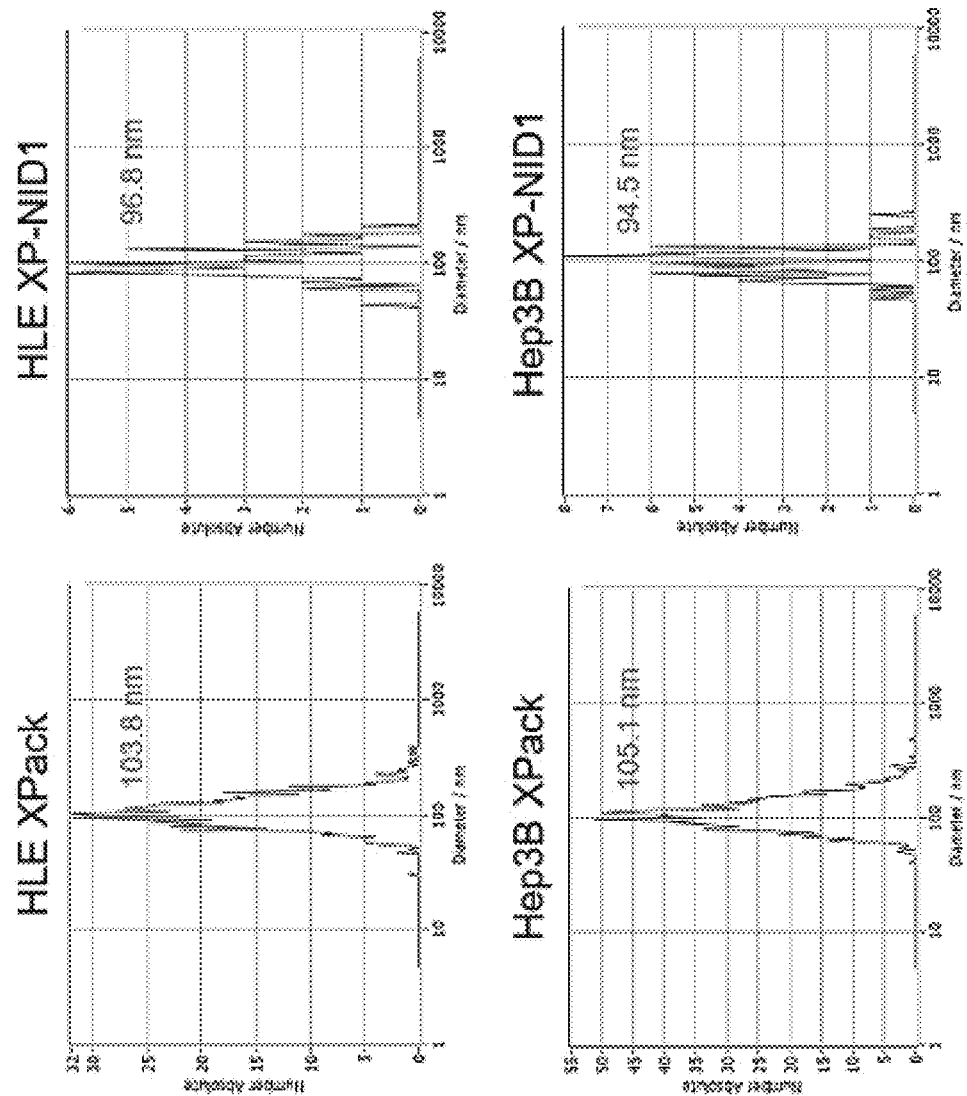

6.4 EV-NID1 Promotes Pre-Metastatic Niche Formation and Distant Metastasis to the Lungs To determine the role of NID1 in HCC, NID1 expression was knocked down in MHCC97L cells and engineered to be expressed in EVs from Hep3B and HLE cells using an expression vector with an EV targeting signal (FIGS. 14A and 14D). Knockdown of NID1 resulted in diminished ability of the tumor cells to grow, migrate and invade (FIGS. 14B-14C). Conversely, overexpression of EV-NID1 showed opposing effects (FIGS. 14E-14H). EVs collected from these stable clones were validated (FIG. 15). The reduced NID1 level in EVs from cells with NID1 knockdown (NID1-KD1 and NID1-KD2) and elevated NID1 level in EVs from cells overexpressing NID1 (XP-NID1) were revealed by enzyme-linked immunosorbent assay (ELISA) (FIG. 4A) and immunoblotting (FIG. 15B). Treatment with EVs from nontarget control cells (CTL-KD-EVs) enhanced the migration and invasiveness of naïve cells. However, this enhancement was abolished in cells treated with NID1-KD-EV (FIG. 4B). XP-NID1-EVs displayed a more potent effect on promoting cell motility and invasion than did EVs derived from vector control cells (XPack-EVs) (FIGS. 4C and 4D). Consistent with the effect of parental MHCC97L-EVs, CTL-KD-EVs demonstrated the positive effect on liver tumor formation and distant metastasis in the EV treatment model. The augmented metastasis to the lungs was not observed in mice injected with NID1-KD-EVs (FIGS. 4E-4G). These functional characterizations provide evidence about the imperative activity of EV-NID1 in tumor growth and metastasis.

Figures 5A, 5B:
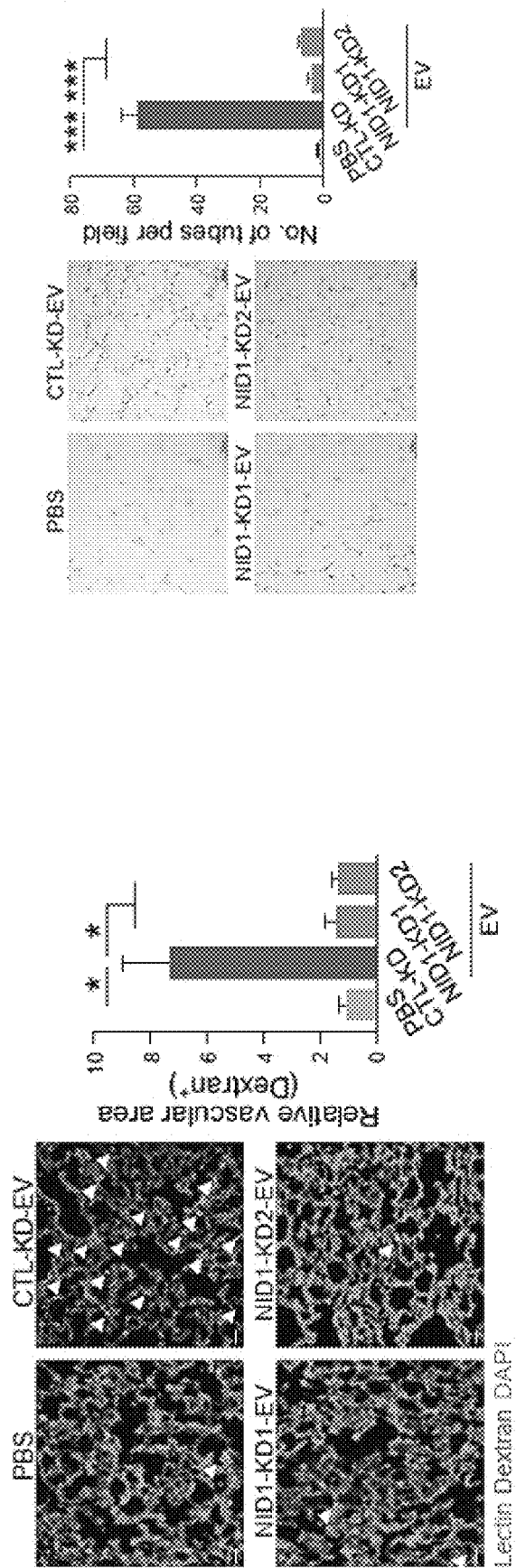
Figure 5C:
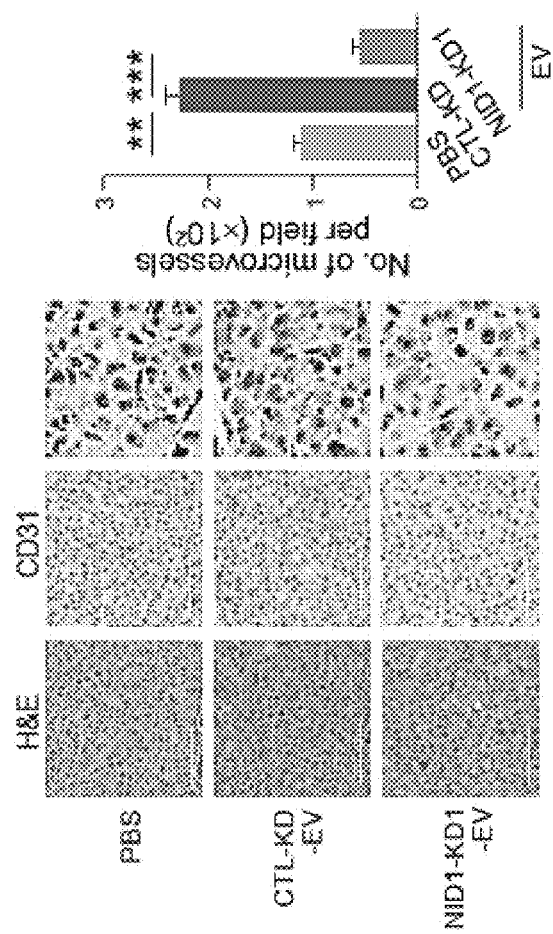
Figure 5D:
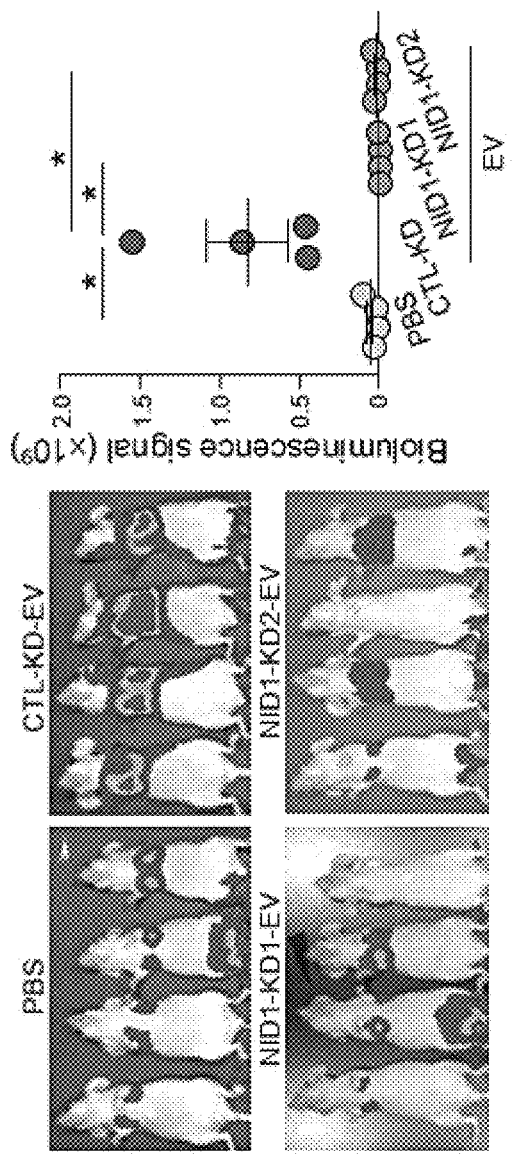
Figure 5E:
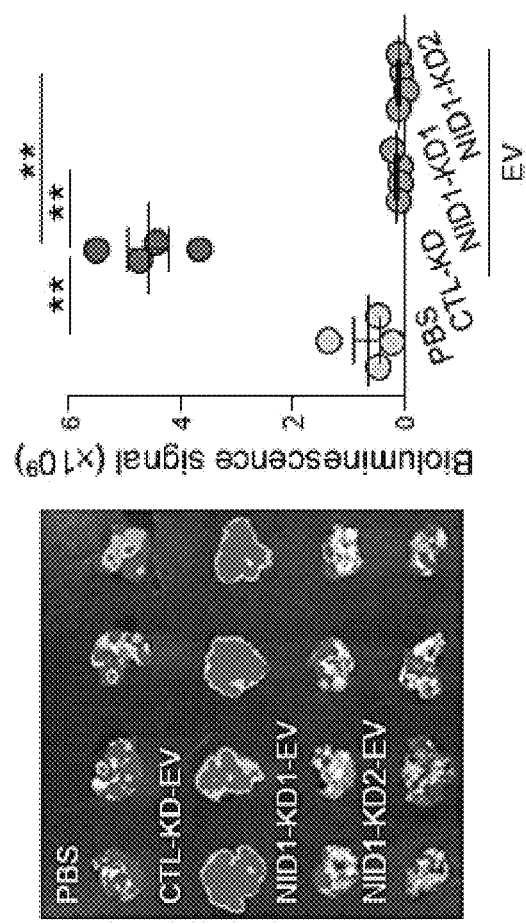
Figure 5F:
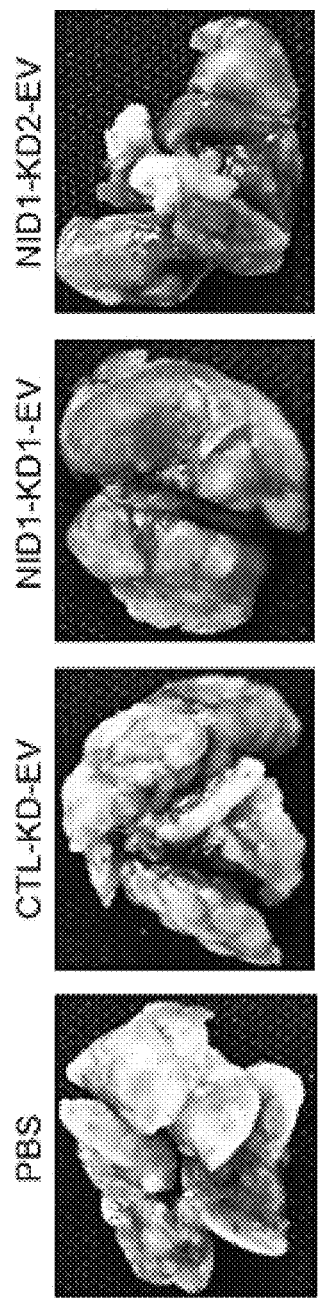
Figure 5G:
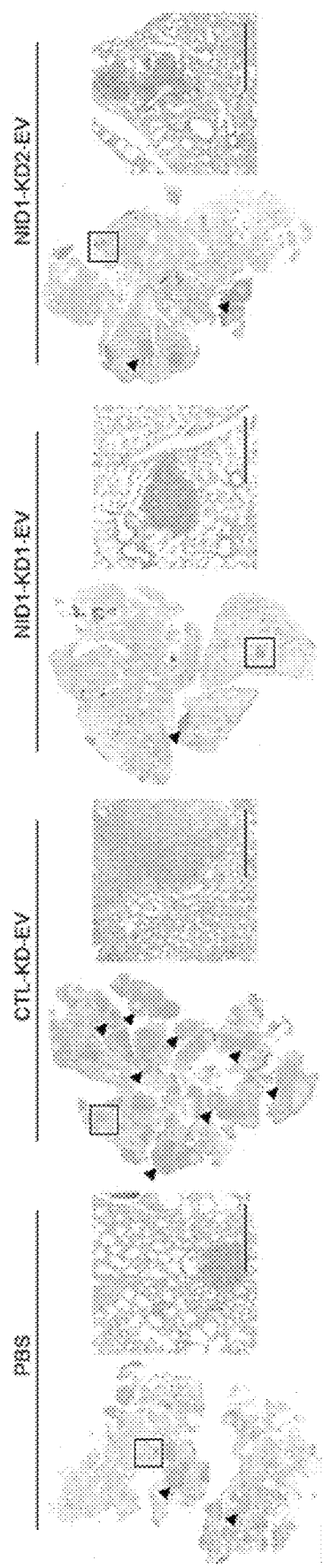
Figures 16A, 16B:
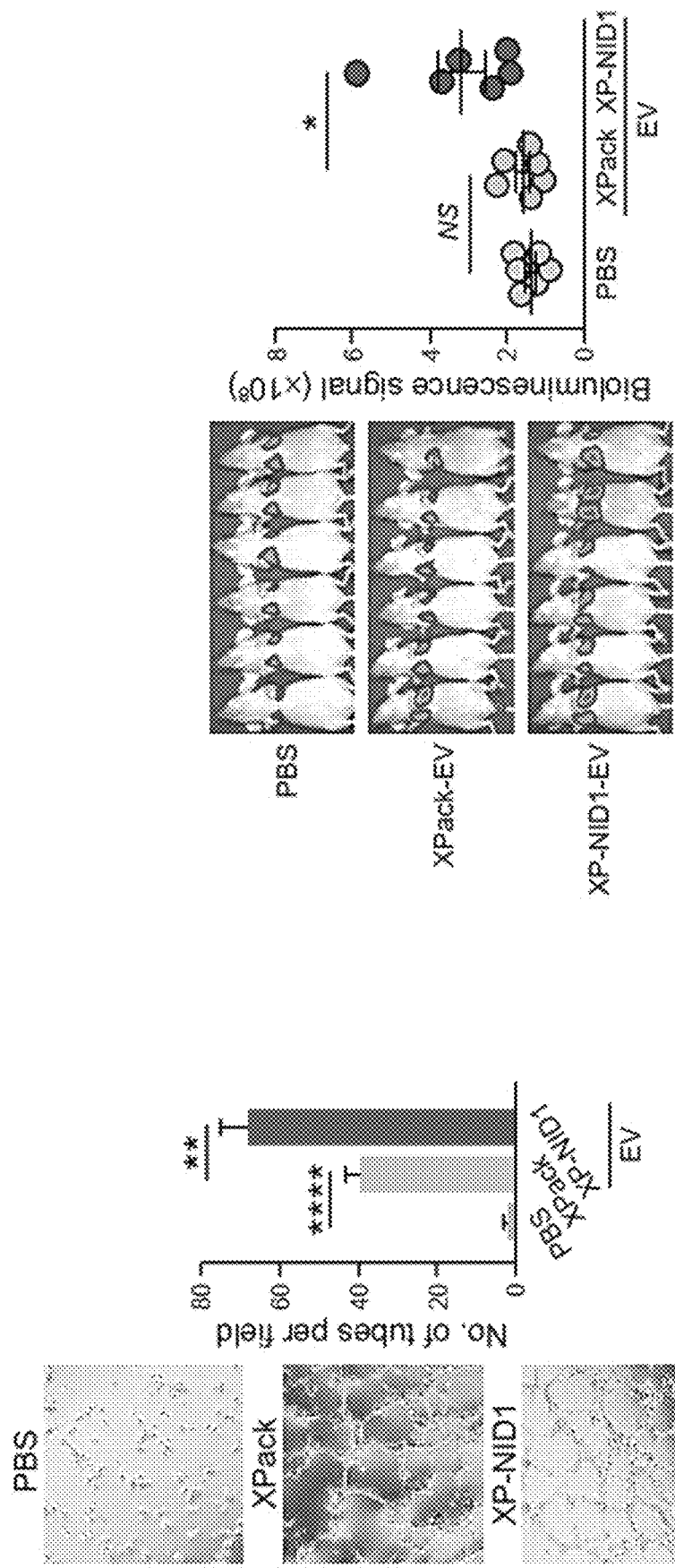
Figure 16C:
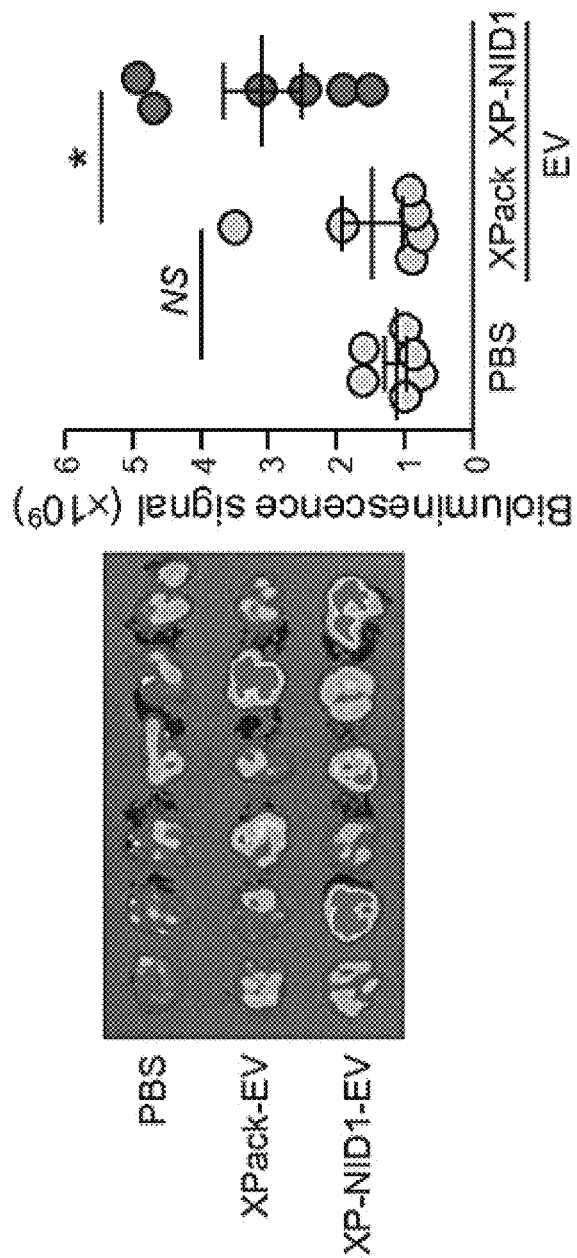
Figure 16D:
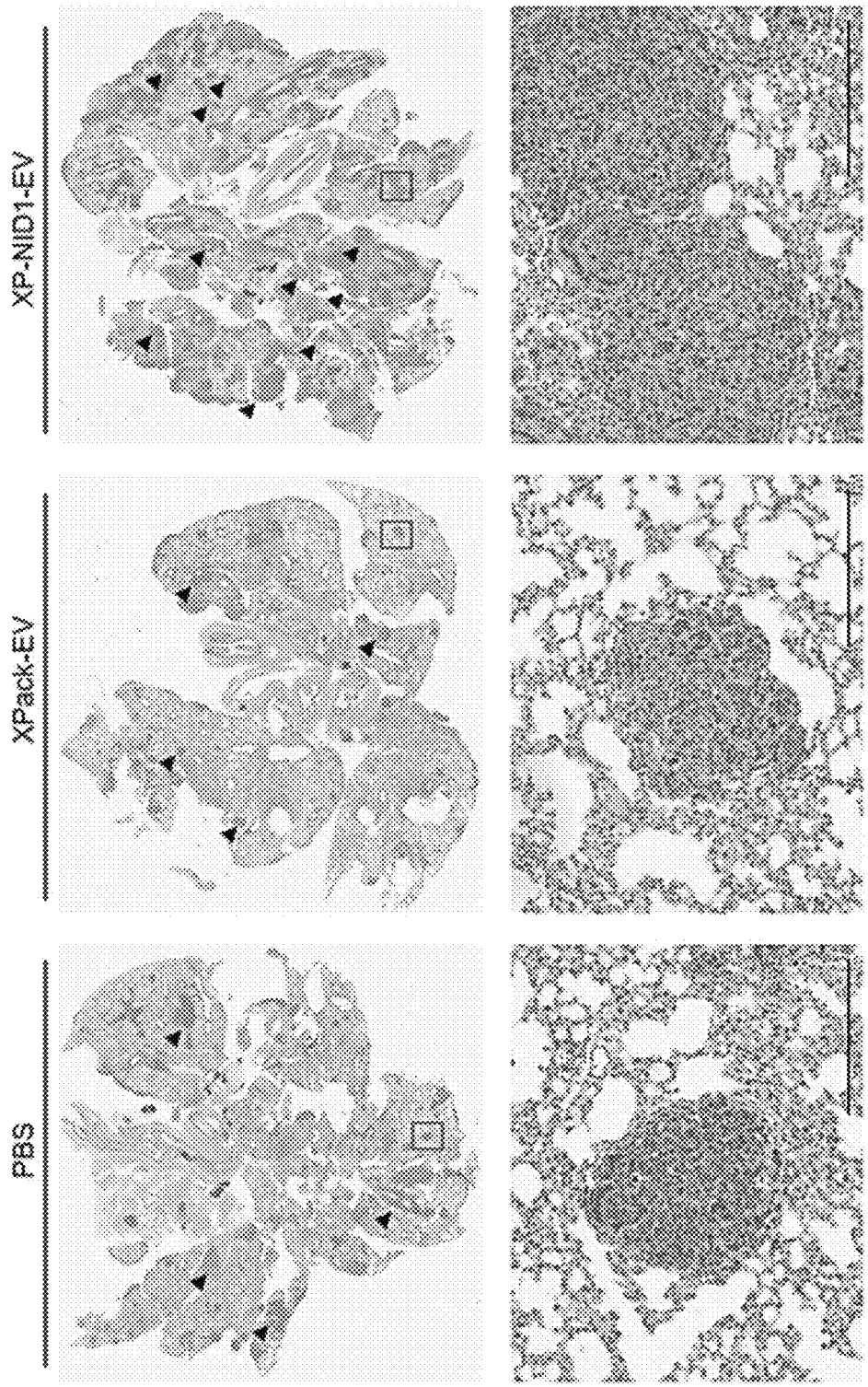

The role of EV-NID1 in modulating the microenvironment in lungs was examined. MHCC97L CTL-KD-EVs enhanced vascular permeability when compared to untreated mice. However, the enhancing effect was not observed in mice injected with NID1-KD-EVs (FIG. 5A). In addition, NID1 knockdown cells resulted in the release of EVs that abolished the promotion of tube-like structure formation of HUVECs and microvessel formation in the Matrigel plug angiogenesis assay (FIGS. 5B and 5C), while XP-NID1-EVs promoted the formation of tube-like structures in endothelial cells (FIG. 16A). Compared to cells injected with PBS, mice injected with p53−/−; Myc hepatoblasts and CTL-KD-EVs showed a profound increase in the colonization of hepatoblasts to the lungs, whereas the colonization of hepatoblasts in the lungs was largely diminished in mice injected with NID1-KD-EVs (FIG. 5D-5G). Conversely, in mice injected with XP-NID1-EVs, augmented colonization of hepatoblasts in the lungs was observed (FIGS. 16B-17D). Taken together, these findings suggest the role of EV-NID1 in destabilizing the vascular architecture and promoting angiogenesis in the lung, thereby facilitating tumor cell colonization.

6.5 EV-NID1 Activates Pulmonary Fibroblasts to Secrete TNFR1

Recruitment of other cell types to prepare a favorable microenvironment for the survival and growth of disseminated metastatic cells at distant sites is a hallmark of the pre-metastatic niche.[25] Immunohistochemistry revealed positive α-SMA staining in the metastatic lesions in the lungs of mice injected with MHCC97L CTL-KD-EVs but not in either untreated mice or mice injected with NID1-KD-EVs, suggesting that the activation of pulmonary fibroblasts induced by EVs is NID1-dependent (FIG. 6A). In accordance with the findings that S100A4-positive fibroblasts induce an angiogenic microenvironment for metastatic colonization,[26] NID1-KD-EVs upregulated the expression of S100A4 and promoted the growth of MRC-5 human lung fibroblasts (FIG. 6B; FIG. 17A). The uptake of EVs by MRC-5 was detected after incubation with EVs (FIG. 6C).

Figures 6D, 6E:
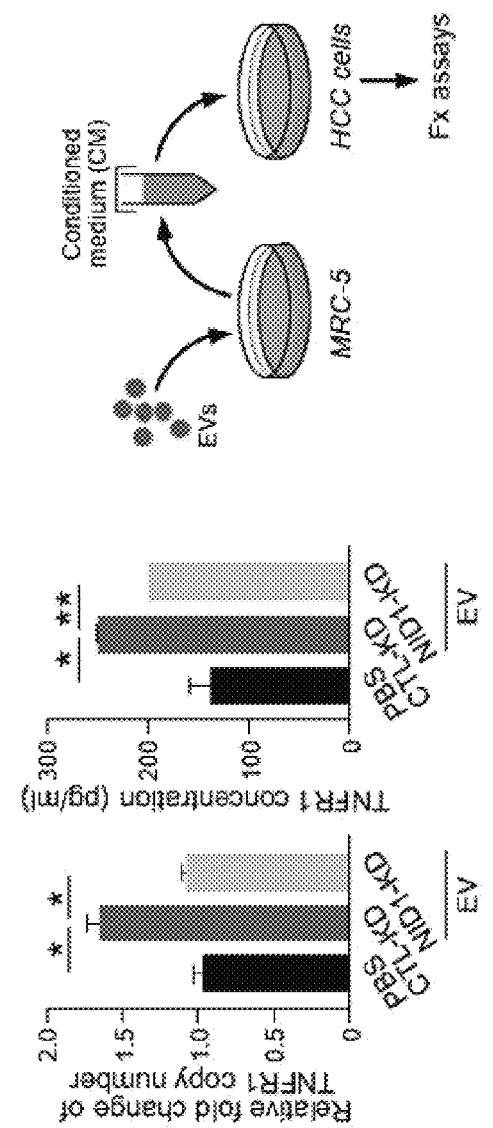

Cytokines, crucial regulators of cell-cell signaling, play critical roles in modulating the tumor microenvironment.[27] To identify cytokines secreted by EV-NID1-stimulated lung fibroblasts, a cytokine array was employed to measure the expression of cytokines in MRC-5 cells treated with CTL-KD- or NID1-KD-EVs. Cytokines that are potentially involved in tumor microenvironment modulation were shortlisted (FIG. 22). Upregulation of tumor necrosis factor receptor 1 (TNFR1) mRNA was detected in MRC-5 cells stimulated with CTL-KD-EVs but not in cells treated with NID1-KD-EVs. A similar trend of soluble TNFR1 (sTNFR1) level in the conditioned medium of MRC-5 cells was observed (FIG. 6D).

Figure 6F:
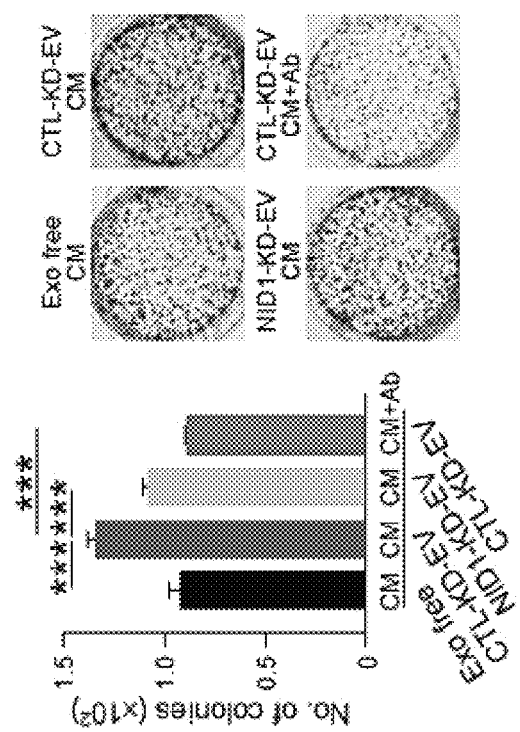
Figure 6G:
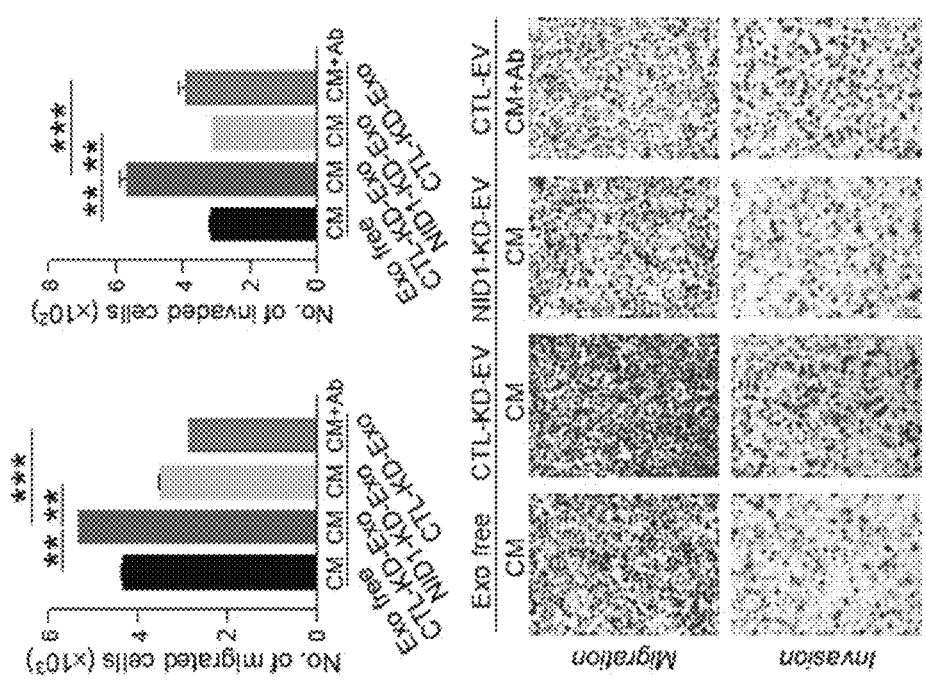
Figure 6H:
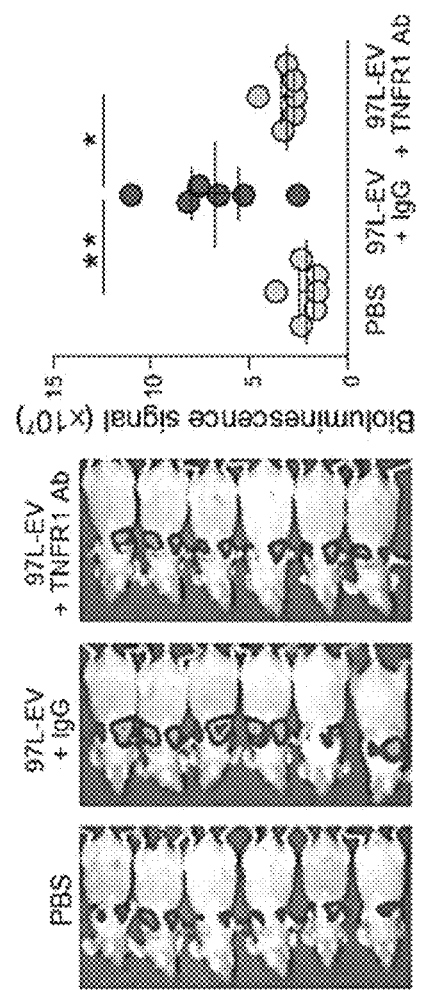
Figure 61:
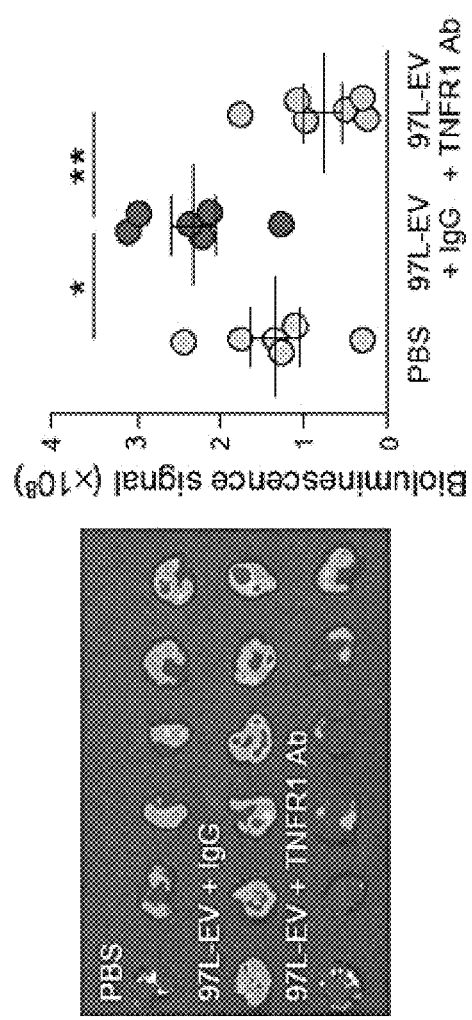
Figure 6J:
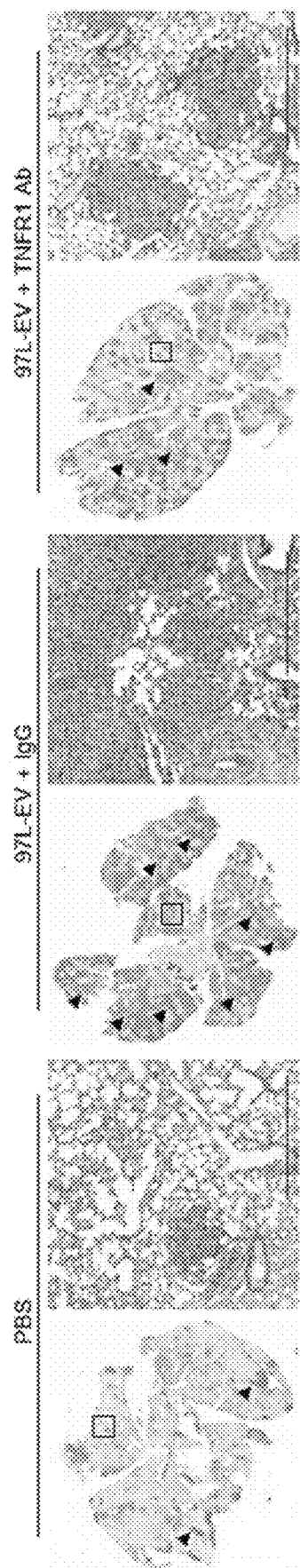

Functionally, the conditioned medium of MRC-5 cells was demonstrated to induce colony formation and promote migration and invasiveness of PLC/PRF/5 cells. The stimulatory effect was further enhanced when MRC-5 cells were pretreated with CTL-KD-EVs. However, this effect was hindered when MRC-5 cells were either pretreated with NID1-KD-EVs or incubated with anti-TNFR1 antibody (FIGS. 6E-6G). A consistent effect of MRC-5 medium on Hep3B cells was observed (FIGS. 17B-17C). The crucial role of sTNFR1 in metastasis was further demonstrated by the largely attenuated MHCC97L-EV- and MHCCLM3-EV-induced colonization of murine p53−/−; Myc hepatoblasts into the lungs of animals injected with anti-TNFR1 antibody (FIGS. 6H-6J; FIG. 18).

6.6 Levels of EV-NID1 and Serum TNFR1 Correlate with Tumor Stage of HCC

Figure 7A:
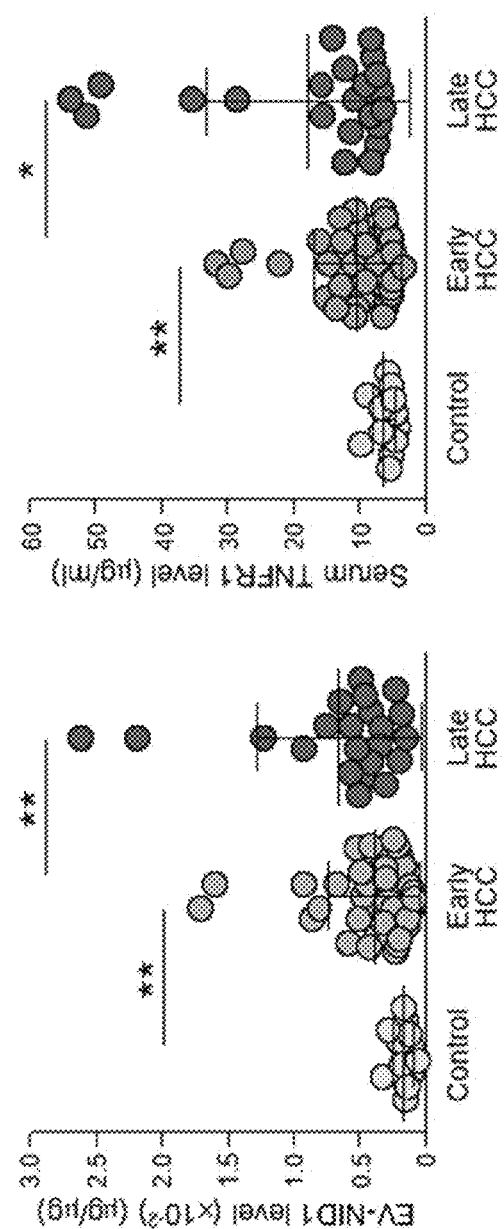
Figure 7D:
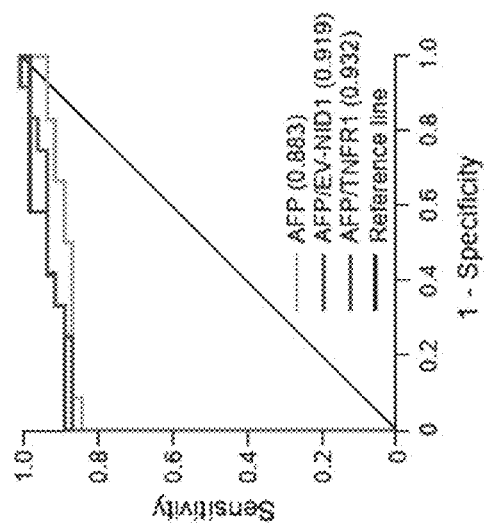

In the mouse model with the implantation of MHCC97L cells, the levels of EV-NID1 increased with the luciferase signal intensity, which reflects the tumor burden in the mice HCC (FIG. 3G and FIG. 13A-13B). To further evaluate the potential application of EV-NID1 as a biomarker for HCC detection, the circulating EVs obtained from non-HCC control subjects and HCC patients with early and late stage disease were validated prior to the analysis of NID1 level (FIG. 19). As shown in FIG. 7A, the results revealed EV-NID1 levels in control subjects ranging from 0.0005-0.0032 µg/µg with a mean level of 0.0014 µg/µg. Compared to control subjects, early stage patients showed a significantly higher overall level of EV-NID1 (mean, 0.0038 µg/µg; range, 0.0007-0.0172 µg/µg; P=0.0037). Late stage patients displayed an even higher EV-NID1 level (mean, 0.0066 µg/µg; range, 0.0013-0.0264 µg/µg; P=0.0072) than early stage patients. Serum TNFR1 showed concomitant upregulation with the HCC stages, and TNFR1 levels increased progressively from the control group (mean, 6.39 µg/ml; range, 4.65-10.26 µg/ml) to the early stage group (mean, 10.56 µg/ml; range, 5.00-32.42 µg/ml; P=0.0079 vs control group) and late stage group (mean, 18.06 µg/ml; range, 6.73-54.77 µg/ml; p=0.0179 vs early stage). The level of EV-NID1 was well correlated with serum TNFR1 level (P=0.0676) (FIG. 7B). The positive association between HCC tumor stage and both EV-NID1 and TNFR1 levels suggests the application of these molecules as noninvasive biomarkers for HCC.

Figure 7C:
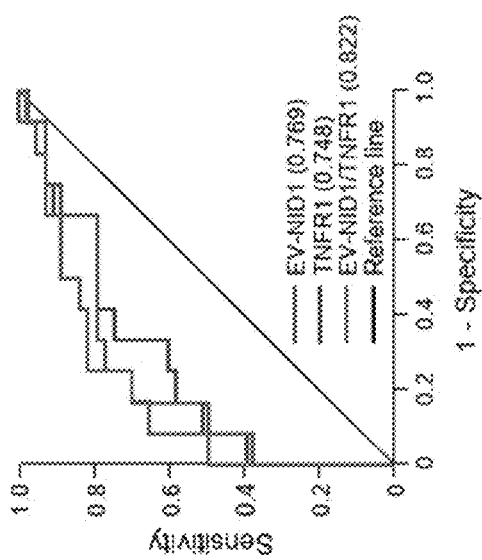
Figure 7B:
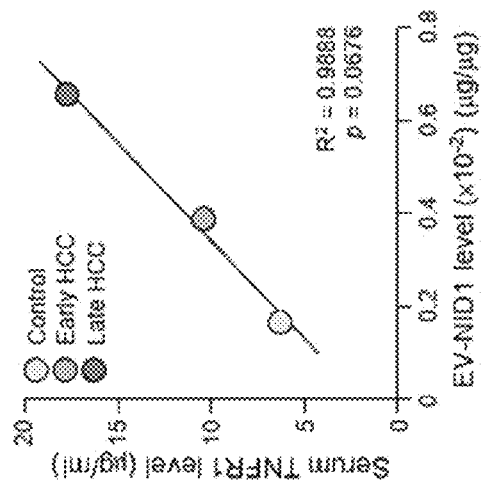
Figure 7E:
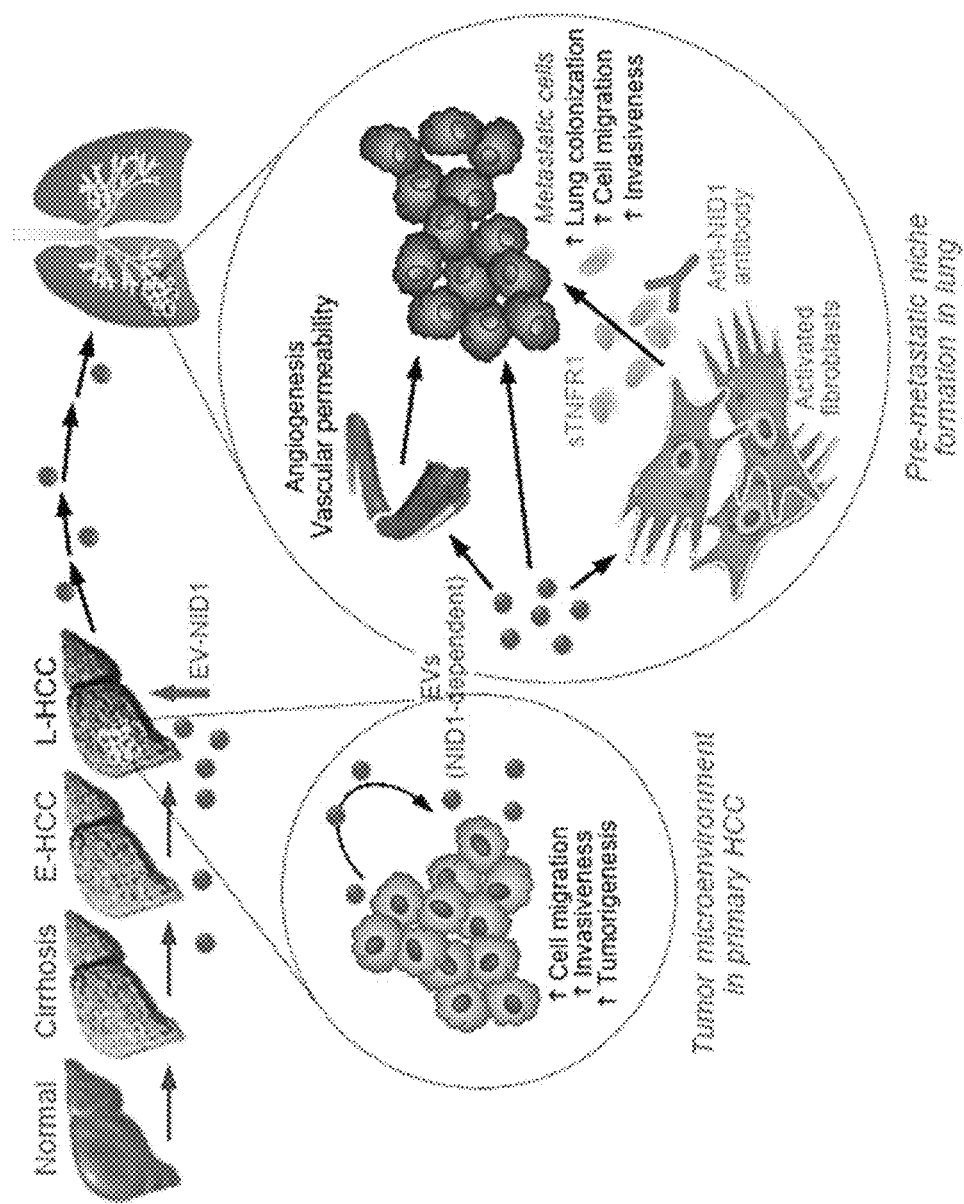

Receiver operating characteristic (ROC) analysis was employed to evaluate the diagnostic value of EV-NID1 and serum TNFR1 in HCC (FIG. 7C). When comparing control subjects to early stage patients, analysis of EV-NID1 resulted in an area under the curve (AUC) of 0.769±0.068 with a 95% confidence interval of 0.636-0.903 (P=0.0046). In addition, the AUC for serum TNFR1 was 0.748±0.070 with a 95% confidence interval of 0.611-0.885 (P=0.0091). These data indicated the effectiveness of EV-NID1 and serum TNFR1 for discriminating HCC patients and control subjects. ROC analysis of combined EV-NID1 and TNFR1 revealed greater sensitivity and specificity than either marker alone, with an AUC of 0.822. ROC analysis of alpha fetal protein (AFP), a biomarker of HCC, measured in the same cohort of sera revealed an AUC of 0.883. ROC analysis of combined AFP and EV-NID1 or TNFR1 demonstrated an enhanced sensitivity and specificity than AFP alone (FIG. 7D). These findings suggest that EV-NID1 and TNFR1 together with AFP may be utilized as an effective biomarker for the early detection of HCC. Taken together, our results showed a progressive increase in EV-NID1 levels during HCC progression. Mechanistically, EV-NID1 promotes the formation of a pre-metastatic niche by activating pulmonary fibroblasts to secrete TNFR1 to facilitate the colonization, growth, migration and invasion of incoming HCC cells in the lungs (FIG. 7E).

Figure 8A:
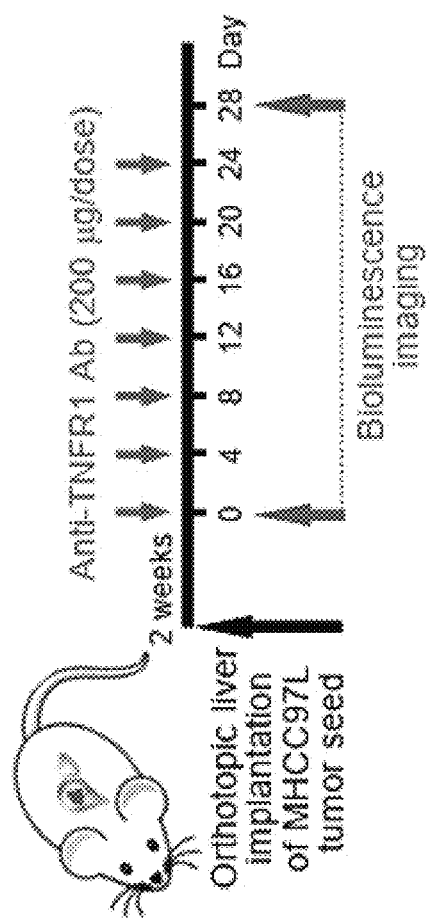
Figure 8B:
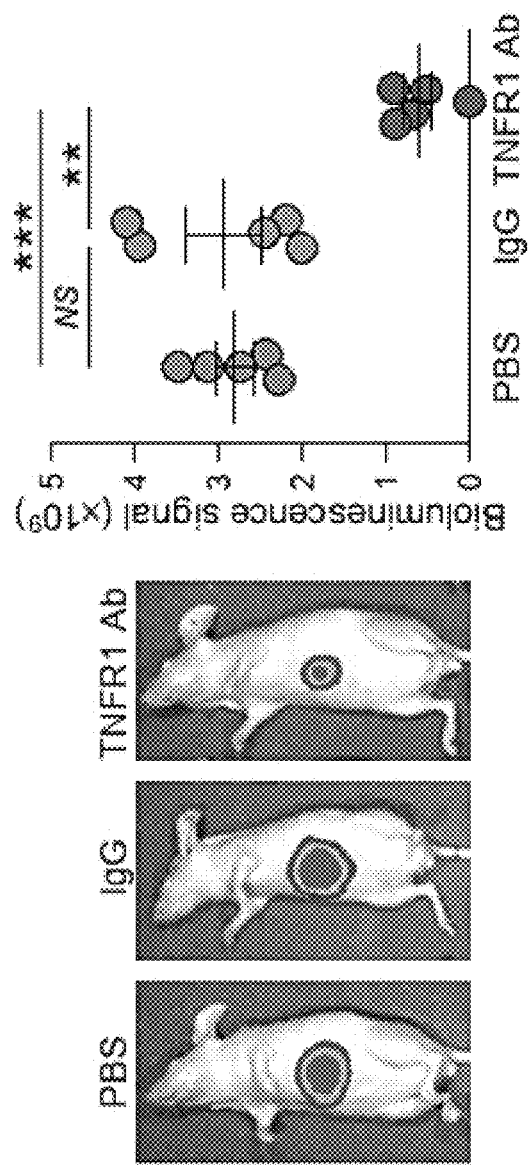
Figure 8C:
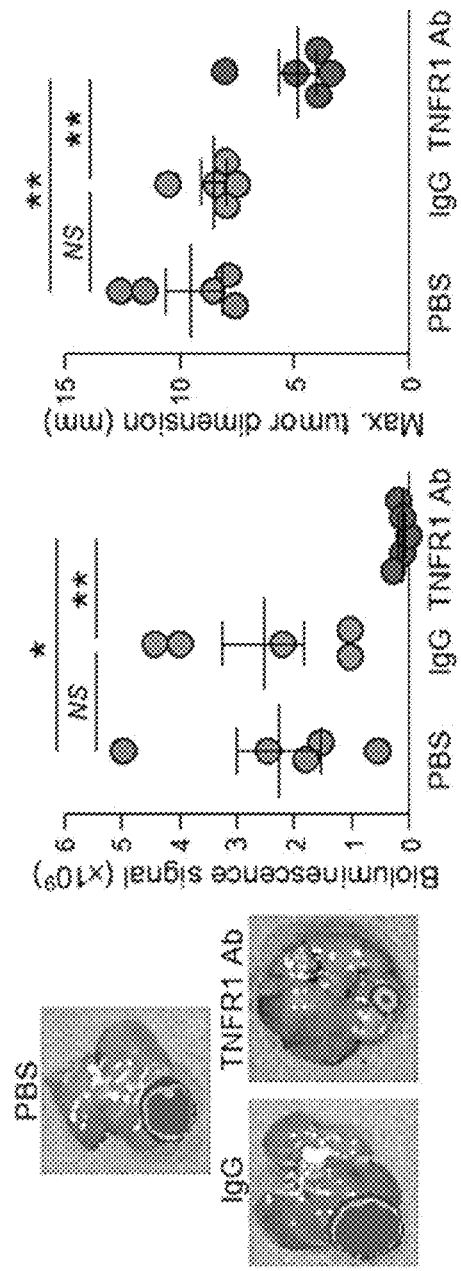
Figure 8D:
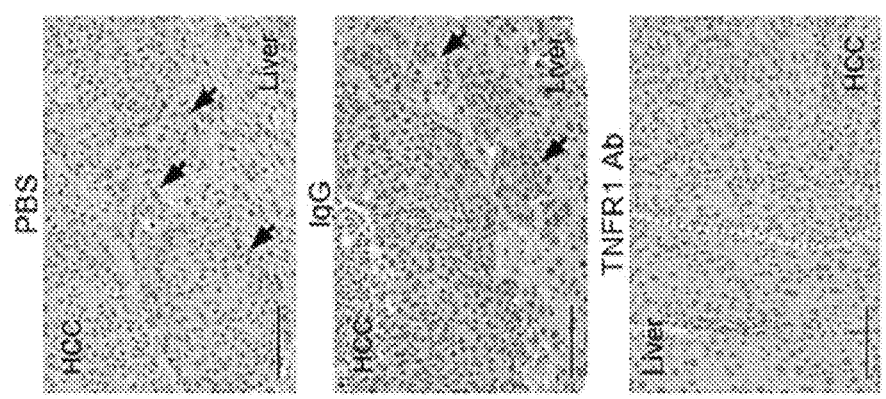
Figure 8F:
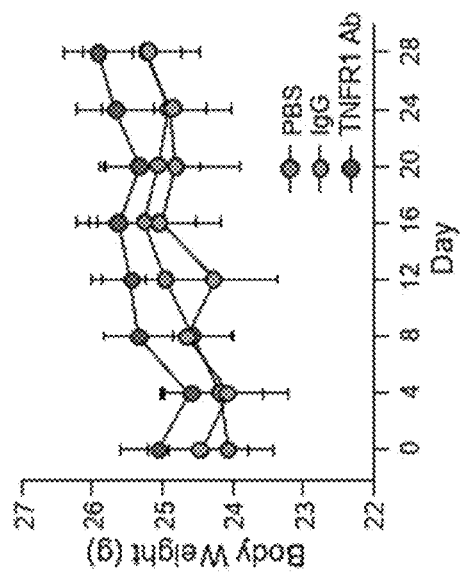
Figure 8E:
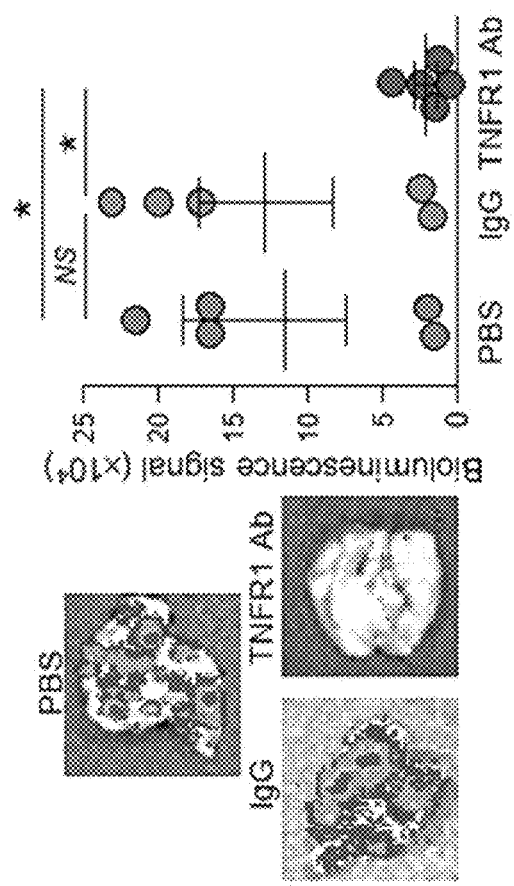

6.7 Antimetastatic Effect of TNFR1 Neutralizing Antibody as Potential Treatment for HCC Our findings showed that sTNFR1 was crucial to HCC metastasis; therefore, neutralization of serum TNFR1 could potentially block the communication between cancer cells and the target tissue microenvironment, leading to the suppression of metastasis. The therapeutic effect of the anti-TNFR1 antibody was tested in mice implanted with metastatic MHCC97L cells in the liver (FIG. 8A). Administration of anti-TNFR1 antibody suppressed primary tumor growth compared to treatment with PBS or control IgG (FIGS. 8B and 8C). Histological examination revealed that liver tumors of the control and IgG group showed expansive tumor growth fronts, while bulging of the contour was observed in liver tumors of anti-TNFR1 antibody-administered mice (FIG. 8D). Three out of five mice in both PBS and IgG group had metastasis to lungs in contrast to none of the mice treated with anti-TNFR1 antibody showed distant metastasis to lungs (FIG. 8E). It was noted that mice in all the experimental groups did not show signs of distress or significant changes in body weight (FIG. 8F). Our findings provide preclinical evidence supporting the efficient blockage of oncogenic signaling mediated by HCC EVs using an anti-TNRF1 antibody.

7.1 Discussion

EVs mediate intercellular communication via the transfer of their EV components to both neighboring and distant cells. The uptake of oncogenic EV contents leads to augmented aggressiveness of recipient cells. In HCC, tumor-derived EVs have been shown to enhance the migratory ability and invasiveness of immortalized hepatocytes[28] and induce cancer progression through promotion of epithelial-mesenchymal-transition (EMT).[29] The transfer of HCC-derived EV miRNAs to recipient cells promotes angiogenesis,[30] cell motility,[31] vascular permeability,[32] and multidrug resistance[33] and activates cell signaling.[3] Indeed, our findings showed that HCC cells treated with tipifarnib, a farnesyltransferase inhibitor identified to be an inhibitor of EV biogenesis,[18] displayed reduced EV secretion in vitro and formed smaller tumors in mouse liver, suggesting that EV release from HCC cells is crucial for tumor development and progression. The functionality of EVs is determined by the composition of their content. EV miR-1247-3p released by HCC cells has been shown to activate CAFs to foster lung metastasis.[34] A recent study reported the effect of EV miR-23a-3p on HCC cells in attenuating antitumor immunity by upregulating PD-L1 expression in macrophages.[35] In addition to containing oncogenic miRNAs, EVs can also contain tumor suppressor miRNAs. For instance, miR-451a, which inhibits HCC by inducing apoptosis and blocking angiogenesis,[36] has been shown to be downregulated in circulating EVs from HCC patients. miR-451. Another tumor suppressor, miR-1251/b, has been shown to inhibit tumor-associated macrophage-mediated cancer stemness in HCC cells.[37] Tangible results have been reported on the functional diversity of EV miR-NAs; nevertheless, the functional potential of EV proteins in HCC has not been well documented. Sugar metabolism-regulated proteins have been described as differentially expressed proteins, with a fold change of 1.5, found in EVs of MHCC97L and MHCCLM3 cells when compared to in EVs of Hep3B cells.[38] Although we used a fold change of 4 to distinguish differentially expressed proteins, most of the upregulated EV proteins that are involved in glycolysis, gluconeogenesis and pentose phosphate pathway identified by the study are also found to be upregulated in our dataset. In addition, we also detected the presence of well-known exosomal proteins such as Cav1, Met and S100 family members in EVs of metastatic cells, as previously reported.[28]

Using proteomic profiling, we identified NID1 as a protein enriched in EVs from metastatic HCC cells. NID1, formerly known as entactin, is an essential structural component of the basement membrane and ECM. The strategic subcellular localization of NID1 enables it to mediate cell attachment and communication between cells and ECM. NID1 has been shown to activate the ERK/MAPK signaling pathway to promote EMT and chemoresistance.[22] The functional capacity of NID1 in cancer metastasis has been revealed in breast, melanoma, ovarian and endometrial cancers.[22-24] In contrast, TMPRSS2-induced invasion of prostate cancer cells has been shown to be mediated by NID1 degradation.[39] NID1 secreted from endothelial cells inhibits breast cancer cell migration.[40] Despite the evidence implicating the complex roles of NID1 in different cancers, its involvement in HCC remains unclear. Here, we showed for the first time the presence of NID1 in EVs of HCC cells, suggesting its unexplored functions in intercellular communications during hepatocarcinogenesis. Although NID1 has been found in EVs of melanoma cells, nasopharyngeal carcinoma cells and urine of healthy individuals,[41-43] yet their roles in human cancers and normal physiology have not been reported. In the current study, comprehensive functional characterization showed the capability of EV-NID1 released by metastatic HCC cells to modulate the microenvironment in distant organs to support the growth and motility of disseminated HCC cells.

The enhanced expression of S100A4 in EV-treated MRC-5 cells and prominent α-SMA staining in metastatic lesions in lungs of mice inoculated with HCC EVs indicate fibroblast activation by EVs derived from metastatic HCC cells. We further identified TNFR1 to be transcriptionally enhanced and secreted by MRC-5 cells activated by EV-NID1. At present, how NID1 activates the transcription of TNFR1 remains unknown. In silico analysis revealed the presence of two putative NF-κB binding sites in the promoter region -1517 and -1890 of TNFR1, suggesting the unexplored effect of NID1 in the activation of NF-κB pathway. The demonstration about the transcriptional regulation of TNFR1 by NF-κB induced by NID1 requires further investigation. TNFR1 signaling has been shown to perpetuate HCC tumor growth and tumor-associated inflammation.[44] Both full-length and cleaved sTNFR1 are released by various cell types. Full-length TNFR1, which is produced independent of cleavage by receptor sheddases, has been detected in EVs.[45] The soluble form released by shedding of the ectodomain of TNFR1 has been shown to be mediated by ADAM17 proteolytic cleavage.[46] Hypoxia and endoplasmic reticulum stress upregulate ADAM17 expression and therefore contribute to enhanced sTNFR1 release. However, the function of sTNFR1 has not been fully understood. ADAM17-mediated shedding of TNFR1 in hepatocytes suppresses proapoptotic signaling during hepatic stress,[47] and the increased level of sTNFR1 secreted by ADAMS-null fibroblasts inhibits apoptosis of melanoma cells.[48] In the clinical context, sTNFR1 levels are elevated in patients with glioblastoma and endometrial cancer.[49, 50] In accordance with the mechanistic findings revealed in this study, the level of sTNFR1 progressively increases from non-HCC individuals to patients with early stage HCC to patients with late stage HCC. In contrast, a higher level of sTNFR1 is associated with better survival in lung cancer patients with and without chronic obstructive pulmonary disease[51]. In addition to its role in cancer, sTNFR1 is strongly associated with other diseases, such as cardiovascular mortality[52] and nonrelapse mortality after hematopoietic cell transplantation.[53]

EVs are regarded as a molecular signature of the parental cells and provide insight about the origin and functions of the parental cells. Recent advances in liquid biopsies hold the promise of assessing EV content for clinical diagnostics. Thus, EVs are regarded as noninvasive sources of biomarkers for the detection and prognosis of various diseases. NID1 levels have been found to be higher in metastatic cancer patients than in patients without metastasis,[24] and ovarian cancer patients have been shown to display an enhanced level of plasma NID1.[54] A recent study reported the detection of NID1 in the saliva of patients with oral cavity squamous cell carcinoma (OSCC).[55] The level of NID1 is well correlated with advanced stages of OSCC and poor survival of OSCC patients. Our study showed that the NID1 level in circulating EVs from mice increased progressively with the bioluminescence signal, which reflects the tumor burden in the animals. Furthermore, analysis of NID1 levels in clinical samples revealed that the level of EV-NID1 was higher in patients with HCC than in control individuals. Together with our findings on serum TNFR1 levels in control subjects and HCC patients, ROC analysis revealed that EV-NID1 and serum TNFR1 levels in combination may be a useful biomarker for HCC. It is intriguing to note that the NID1 transcript level showed no significant difference between nontumorous liver tissues from patient cohort and available from the TCGA database of liver cancer as well as other solid tumors such as colon, breast and lung cancers (FIG. 20). According to the information of the Human Protein Atlas, the protein level of NID1 in liver, colon and lung and breast cancers are undatable or weakly positive. It is worthwhile to understand how NID1 is particularly packaged and secreted in the form of EVs by cancer cells.

A preclinical study reported that administration of anti-TNFR1 antibody in mice grafted with melanoma cells potentiates the effect of anti-PD-1 antibody in suppressing tumor growth. In the same study, TNFR1-deficient mice injected with melanoma cells displayed a significantly enhanced anti-PD-1 response compared to that in wild-type mice[56]. TNF is an antitumor agent; however, the clinical application of TNF is limited by its induction of systemic cytotoxicity. The lethality of TNF in tumor-bearing mice is mitigated by the application of anti-TNFR1 antibody, thus facilitating the design of a safe TNF-based antitumor therapeutic strategy.[57] Here, we showed in a mouse model that anti-TNFR1 antibody significantly suppressed liver tumor formation and distant metastasis to the lungs. HCC is often diagnosed at an advanced stage; therefore, most HCC patients are precluded from curative treatment options. Sorafenib is the first-line therapy for patients with inoperable liver cancer; unfortunately, the ability of sorafenib to shrink tumors is modest, and its systemic toxicity is high. More importantly, most patients are highly refractory to sorafenib.[58] New molecular targeted agents, such as regorafenib and lenvatinib, are not superior to sorafenib in terms of the overall survival of HCC patients. Supported by our current findings and previous studies about the crucial role of TNFR1 in tumorigenesis, blocking TNFR1 with neutralizing antibodies or antagonists either alone or in combination with other therapeutic agents may be envisaged to expand upon the current limited treatments for HCC.

In summary, our study demonstrated the functionality and clinical implications of EV-NID1 in HCC. We also revealed that blocking EV-mediated communication between cancer cells and the target tissue microenvironment with an anti-TNFR1 antibody could diminish the malignant phenotype of HCC.

7.2 Experimental Procedures

Cell Culture: Human HCC cell lines, Hep3B and PLC/PRF/5 and other human cell lines, human umbilical vein endothelial cell line (HUVEC), MRC-5 human lung fibroblasts and human 293FT, were purchased from American Type Culture Collection (ATCC) and cultured according to the ATCC recommendations. For other HCC cell lines, HLE was obtained from Japanese Collection of Research Bioresources (JRCB, Japan) and MHCC97L and MHCCLM3 were obtained from Cancer Institute, Fudan University, China H2P and H2M were provided by Xin-Yuan Guan, The University of Hong Kong, Hong Kong[56]. Human immortalized normal liver cell lines were also used. LO2 was obtained from the Institute of Virology, Chinese Academy of Medical Sciences, Beijing, China and MIHA was provided by Jayanta Roy-Chowdhury, Albert Einstein College of Medicine, New York[57]. Murine p53−/−; Myc hepatoblasts was provided by Scott Lowe, Memorial Sloan Kettering Cancer Center, New York[58]. These cell lines were cultured according to provider's recommendations. All cell lines were tested routinely before use to avoid mycoplasma contamination.

Isolation of EVs from Conditioned Medium of Cell Culture and Blood of Mouse and Patients: For EV isolation from cell culture supernatants, cells were cultured in media supplemented with 10% EV-depleted fetal bovine serum (FBS). EV-depleted FBS was prepared by overnight centrifugation at 100,000×g at 4° C. (Beckman Coulter, Avanti JXN-30). Supernatants were collected from cells cultured in medium with EV-depleted FBS for 72-hr and EVs were purified by differential centrifugation. In brief, culture supernatants were centrifuged at 2,000×g for 15 min to remove cell debris and dead cells (Thermo Fisher Scientific, Heraeus Multifuge X3FR). Microvesicles were removed after centrifugation at 20,000×g for 30 min at 4° C. (Beckman Coulter, Avanti JXN-30). Supernatants were then centrifuged at 100,000×g for 2 hr at 4° C. (Beckman Coulter, Avanti JXN-30) to pellet the EVs. The EVs were washed with PBS and collected by ultracentrifugation at 100,000×g for 2 hr at 4° C. (Beckman Coulter, Avanti JXN-30). Mouse blood was obtained by cardiac puncture at the endpoint. Blood was also provided by non-liver disease individuals and HCC patients. To collect circulating EVs, blood was first centrifuged at 1,500×g for 30 min to obtain serum (Thermo Scientific, Heraeus Multifuge X3R). Purification of circulating EVs from serum was performed using the ExoQuick PLUS™ Exosome Purification Kit for Serum & Plasma (System Biosciences). The serum was first centrifuged at 16,500×g for 45 min (Eppendorf, 5430R) to pellet large vesicles. EVs were then purified using the purification kit according to manufacturer's protocol.

Validation of Isolated EVs: Proteins were extracted from isolated EVs and subjected to immunoblotting using anti-Alix, anti-CD9, anti-TSG101, anti-GM130, anti-p62 and anti-α-tubulin antibodies. To examine the integrity of the isolated EVs, purified EVs suspended in PBS were dropped on formvar carbon-coated nickel grids. After staining with 2% uranyl acetate, grids were air-dried and visualized using Philips CM100 Transmission Electron Microscope (FEI Company). The size range of EVs was measured by ZetaView® BASIC NTA PMX-120 (Particles Metrix GmbH).

Animal Studies: All animal studies were carried out under the research protocol CULATR 4394-17, 4611-18, 4847-18 and 5012-19 approved by the Committee of the Use of Live Animals in Teaching and Research (CULATR) at The University of Hong Kong. All animal work and procedures were followed strictly according to the Animals (Control of Experiments) Ordinance (Hong Kong) and the Institute's guidance from Laboratory Animal Unit, Li Ka Shing Faculty of Medicine, The University of Hong Kong. BALB/cAnN-nu mice were used in experiments with animals. All mice were provided by and housed in specific pathogen free area in the Laboratory Animal Unit.

EV Education Model: Male 6-week old BALB/cAnN-nu mice were injected intravenously with 15 μg EVs or PBS as control once per week for 3 weeks. At the end of education, mice were subjected to orthotopic liver implantation. To obtain tumor seed for orthotopic liver implantation, $1 \times 10^6$ luciferase-labeled MHCC97L cells were inoculated into the right flank of male 4-week old BALB/cAnN-nu mice. After 2 weeks, mice were killed by euthanasia agent and tumor mass harvested was cut into small pieces of about 1 mm$^3$ in size. Mice to be implanted with tumor seed were anesthetized and laparotomy was performed to expose the liver for tumor seed implantation. To monitor tumor development, mice received intraperitoneal injection with D-luciferin (GoldBio) were subjected to weekly bioluminescence imaging. Images were captured and the bioluminescence signal was quantified using IVIS Spectrum imaging system (Perkin Elmer). At the end of experiment, the mice were sacrificed and their lungs and livers were excised for histological analysis.

Labeling of EVs for Uptake Analysis: EVs were fluorescently labeled with either PKH67 or PKH26 Membrane Dye Labeling Kit (Sigma Aldrich) according to manufacturer's protocol. Labeled EVs were washed with PBS and collected by ultracentrifugation as described above. To examine uptake of EVs by cells, $1 \times 10^5$ cells were treated with 10 μg labeled EVs for 24 hr. After incubation, cells treated with EVs were fixed with 4% formaldehyde in PBS and stained with DAPI before examined under widefield fluorescence microscope (Leica) or laser scanning confocal microscopy (Carl Zeiss LSM700).

Tissue Distribution of EVs: Male 6-week old BALB/cAnN-nu mice were injected intravenously with 15 μg CD63-GFP$^+$ EVs or PKH67-labelled EVs. Each mouse was anesthetized and perfused to collect lung, liver, spleen, brain and pancreas. Tissue sections from different organs were stained with DAPI and examined under confocal microscopy. Five random fields of each section were captured and 3 sections per organ were examined Images were processed by ZEN software (Version 6.0.0.309) and the percentage of EV-positive cells was quantified by ImageJ software (Version 1.50i).

Pulmonary Leakiness Assay: Male 6-week old BALB/cAnN-nu mice were injected intravenously with 15 μg EVs or PBS as control. Twenty hr after EV injection, mice were injected intravenously with Texas Red lysine-fixable dextran (70,000 MW, Thermo Fisher Scientific) at 100 mg/kg. After 3 hr, mice were injected intravenously with Alexa Fluor concanavalin A (Thermo Fisher Scientific) at 10 mg/kg. Ten min later, each mouse was anesthetized and perfused with PBS and followed by 4% formaldehyde in PBS. Lung tissues were excised and immersed in 30% glucose in PBS overnight. Tissues were cryosectioned at 12 μm thickness. Tissue sections were stained with DAPI (Thermo Fisher Scientific) and examined under confocal microscopy for vascular leakage. Five random fields of each section were captured and 3 sections per lung were examined Images were processed by ZEN software and the area of dextran was quantified by Image J software.

Lung Colonization Study: For lung colonization model, $1 \times 10^5$ murine p53−/−; Myc hepatoblasts together with 10 μg EVs or PBS were injected intravenously into male 6-week old BALB/cAnN-nu mice. The mice were subjected to weekly bioluminescence imaging. At the end of experiment, ex vivo bioluminescence imaging of lungs was performed, and dissected lungs were subjected to histological analysis.

Sample preparation for proteomic analysis: Lysate in 8 M urea/100 mM Tris-HCl buffer was incubated at 60° C. for 10 mM Dithiothreitol (DTT) was then added to the samples at a final concentration of 5 mM and incubated for 20 mM at room temperature. Then iodoacetamide was added to a final concentration of 25 mM and incubated in the dark for 30 mM. Subsequently, trypsin was added at a ratio of 1:50 (trypsin:protein) after dilution of buffer to 1 M of urea and incubated at 37° C. for 16 hr. The proteolysis was quenched by addition of 5% formic acid. The digested samples were desalted using C18 STAGE tips and concentrated by SpeedVac (Thermo Savant).

Liquid chromatography tandem MS (LC-MS/MS) analysis: The protein digest samples were analyzed with a UPLC-MS/MS setup. The analytical column was a 25 cm column (360 μm outer diameter, 50 μm inner diameter, 1.9 μm C18 packing material, Pepsep). The mobile phases consisted of A (0.1% formic acid in water) and B (0.1% formic acid in 80% ACN). Each sample (containing 2 μg peptides) (with technical triplicates) was loaded onto the analytical column by the auto-sampler of the UPLC (EASY-nLC™ 1200, Thermo Scientific™) eluted with a gradient of 7% to 10% B for 20 min, followed by a gradient of 10% to 14% B for 30 minutes and subsequently eluted with a gradient of 14% to 27% B for 80 min then eluted with a gradient of 27% to 45% for 30 minutes at a flow rate of 200 nl/min For the MS analysis, Orbitrap Fusion™ Tribrid™ Mass Spectrometer (Thermo Scientific™) was operated in a data-dependent mode cycling through a high-resolution (120,000 at 400 m/z) full scan $MS^1$ (375-1,500 m/z) followed by HCD $MS^2$ scans on the most abundant ions from the immediately preceding full scan in a cycle time of 3 s. The selected ions were isolated with a 1.6-Da mass window and put into an exclusion list for 60 s after they were first selected for HCD.

Data analysis: Raw files generated during LC-MS/MS analysis were searched against the Uniprot Human database (Downloaded on 23 Mar. 2020, 188,357 entries) with MaxQuant search engine (version 1.6.5.0). In which the search was specified to trypsin digestion (allowed up to two missed cleavages), oxidation of methionine as a dynamic modification, and iodoacetamide derivative of cysteine as a static modification. The mass tolerance for MS1 was 20 ppm for first search; 4.5 ppm for main search and for MS2 was 20 ppm. With a decoy search strategy, the peptide false discovery rate (FDR) was set to 1%. Label-free quantification (LFQ) option was enabled with normalization and only those proteins with non-zero LFQ intensities in all the three replicates were interpreted. Statistical analyses were performed with a two-tailed Student's t-test (MS Excel), with changes showing $P<0.05$ considered as statistically significant. The mass spectrometry proteomics data have been deposited to the ProteomeXchange Consortium via the PRIDE[62] partner repository with the dataset identifier PXD019566.

Enzyme-Linked Immunosorbent Assay: Human NID1 ELISA Kit (Abnova) was used to determine NID1 expression in EVs extracted from sera of mouse and patients as well as cell culture medium. The isolated EVs were lyzed and the proteins were subjected to the measurement of NID1. Human AFP ELISA Kit (Solarbio) and Human TNFR1 (Sino Biological) were used to determine level of AFP and TNFR1 in serum of patients. The level of EV-NID1 was expressed as amount of NID1 over EV protein amount (μg/μg) (w/w) and TNFR1 and AFP levels were expressed as TNFR1 and AFP amount per serum volume (ng/ml).

Construction of NID1 Expression Plasmid: NID1 was expressed in the EVs of cells using XPack™ EV Protein Engineering Technology (System Biosciences). NID1 fragment (nucleotides 21-3123; Accession No. BC045606.1) was released from NID1/Entactin cDNA ORF Clone (Sino Biological) and subcloned into CMV-XP-MCS-EF1αα-

Puro Cloning Lentivector (System Biosciences) via XhoI and EcoRI sites. NID1 fragment (nucleotides 3124-3357) was amplified by PCR using primers NID1-3111F and NID1-stopR using Human NID1/Entactin cDNA ORF Clone in cloning vector (Sino Biological) as template. Sequences of primers NID1-311F and NID1-stopR were listed in FIG. 23. The PCR fragment was purified, digested by restriction enzymes and subcloned into CMV-XP-MCS-EF1α-Puro Cloning Lentivector carrying NID1 fragment (nucleotides 3124-3357) via EcoRI and PstI sites. The amplified NID1 region was confirmed by DNA sequencing.

Establishment of NID1 Knockdown and EV-Targeting NID1 Stable Clones: MHCC97L NID1 knockdown stable clones (NID1-KD1 and NID1-KD2) were established using Human NID1 MISSION shRNA Plasmid DNA (Sigma-Aldrich). Non-target control clone (CTL-KD) was generated using MISSION™ non-target shRNA control vector (Sigma-Aldrich). FuGENE® 6 Transfection Reagent (Promega) was used to transfect shRNA plasmid with the addition of MISSION® Lentiviral Packaging Mix into HEK293FT cells. The viral supernatant was collected, centrifuged and filtered. For the viral infection of MHCC97L, viral supernatant and polybrene transduction enhancer (8 μg/ml) were added. Twenty-four hours after transduction, MHCC97L was selected by puromycin (Thermo Fisher Scientific). NID1 was expressed in the EVs of HLE and Hep3B by XPack™ EV Protein Engineering Technology (System Biosciences). XPack CMV-XP-MCS-EF1α-Puro Cloning Lentivector carrying Xpack-NID1 fragment was used to establish EV-targeting NID1 clone (XP-NID1). Empty XP-MCS-EF1α-Puro vector was used to establish vector control clone (XPack).

EV Treatment of MRC-5 Cells: MRC-5 cells were seeded at a density of $2 \times 10^5$ in 6-well plates and subjected to 72-hr 10 μg EV treatment one day after seeding. After incubation with EVs, the cells were washed by PBS twice and cultured in complete medium for another 72 hr. The conditioned medium was then used to treat HCC cells for different functional assays. HCC cells were treated with EVs for 72 hr before subjected to functional assays.

Cytokine Array: Conditioned medium of MRC-5 pre-treated with PBS, MHCC97L CTL-KD- and NID1-KD-EV were collected after 72 hr in EV depleted medium. The collected conditioned media were incubated with Human Cytokine Array C1000 (RayBiotech) containing 120 human cytokine specific antibodies. Chemiluminescent signals were detected by ECL™ Western Blotting Detection Reagents. Relative cytokine intensities were normalized to the signal intensity of the control spots on the same membrane. Ratios among groups were calculated for the different cytokines by ImageJ software. Protein candidates were selected and confirmed by quantitative real-time PCR analysis. Sequence of primers was listed in FIG. 23.

Treatment using Anti-TNFR1 Antibody in Mouse Model: BALB/cAnN-nu mice implanted with luciferase-labeled MHCC97L tumor seed as described above was monitored using bioluminescence imaging. When the luciferase signal of mice reached $1.75 \times 10^7 \pm 10\%$, they were randomized for treatment with PBS (200 μl), IgG antibody (200 μg in 200 μl PBS) or anti-TNFR1 antibody (200 μg in 200 μl PBS) once every 4 days by intraperitoneal injection for a total of 28 days. At the end of the treatment, mice were subjected to bioluminescence imaging. The mice were then sacrificed and their lungs and livers were obtained for histological analysis.

Human Samples: Blood samples were collected from individuals with non-liver diseases (as control subjects), and patients with early and late HCC who had not received any treatment. Information of blood donors was listed in FIG. 24. The collection of blood samples was carried out at Queen Mary Hospital, Hong Kong and Zhujiang Hospital, Guangzhou, China. Informed consent was obtained from all donors. The collection and use of blood samples was approved by the Institutional Review Board of The University of Hong Kong/Hospital Authority Hong Kong West Cluster (HKU/HA HKW IRB) and Zhujiang Hospital of Southern Medical University. All experiments involving blood samples from all donors were performed in accordance with relevant ethical regulations.

Statistics: The data of all assays was calculated as mean±standard error of mean (SEM). Student's t-test performed by GraphPad Prism 6 were used for the statistical analysis. Pearson correlation test was used to analyze the correlation between EV-NID1 and serum TNFR1 levels. The ROC curve was done to detect the AUC which reflects the accuracy of EV-NID1 (μg/μg) and TNFR1 (ng/ml) alone or in combination with AFP (μg/L) as diagnostic biomarkers to discriminating between the healthy control group from the early HCC group. The variables with P<0.05 were analyzed by logistic regressions by IBM SPSS Statistics 25. P-value of less than 0.05 was considered as statistically significant.

Western Blot Analysis

Protein lysates were obtained by cell lysis with NETN lysis buffer (0.1% NP40, 25 mM Tris-HCl, 50 mM $NaCl_2$, 0.2 mM EDTA), supplemented with 10% cOmplete™ protease inhibitor cocktail and 10% PhosStop phosphatase inhibitor cocktail (Roche Applied Science). Bradford reagent (Bio-Rad Corporation) using bovine serum albumin as standard concentration was used to quantify protein amount. A total of 30 μg of protein per lane was resolved by SDS-PAGE, followed by a wet transfer to PVDF membranes (Amersham) for immunoblotting. Chemiluminescent signals were detected by ECL™ Western Blotting Detection Reagents (Amersham).

Immunohistochemistry and H&E

Formalin-fixed, paraffin-embedded tissue was sectioned with a thickness of 5 μm and deparaffinized in xylene, followed by rehydration in a gradient of alcohols (100%, 95% 70%) and distilled water. Antigen retrieval was conducted by immersing the sections in pre-heated EnVision™ FLEX Target Retrieval Solution, High pH (Agilent). The sections were microwaved for further 15 mins and allowed to cool down in the retrieval solution for at least 20 minutes at room temperature. After blocking the endogenous peroxidase by EnVision™ FLEX Peroxidase-Blocking Reagent, the sections were subjected to incubation with primary and secondary antibodies. Signal detection was facilitated by the addition of Dako REAL EnVision™ Detection System and DAB chromogen for 30 mins and 2 mins respectively at room temperature. The specimen section was also stained with hematoxylin and eosin stain. NanoZoomer Digital Pathology System (Hamamatsu) was used to process slides and to create high-quality digital images for analysis.

Enzyme-Linked Immunosorbent Assay

Human CD63 ELISA Kit (Aviva Systems Biology) was used to determine CD63 expression in EVs extracted from sera of mouse and patients. The isolated EVs were lyzed and the proteins were subjected to the measurement of CD63. The level of EV-CD63 was expressed as amount of CD63 over EV protein amount (μg/μg) (w/w).

Tipifarnib Treatment of Cells

To examine the effect of Tipifarnib (AdooQ Bioscience) in EV secretion, MHCC97L was treated with 1 μM Tipifarnib for 48-hr. After replenished with EV-depleted medium, EVs were isolated from the conditioned medium of Tipifarnib-treated MHCC97L after 72 hr. The amount of isolated EVs was quantified. To study the ability of HCC cells with reduced EV secretion to form tumor, $1\times10^6$ Tipifarnib-treated MHCC97L cells were resuspended in 100% Matrigel and inoculated into left lobe of the livers of 6-week old male BALB/cAnN-nu mice. After 6 weeks post injection, mice were sacrificed and liver tumor volume was measured using a caliper and calculated using the formula: volume=$L\times W^2\times 0.5$ (L, the largest diameter; W, the smallest diameter).

Treatment of Cells with EVs prior to Functional Assays

HCC and HUVEC cells were seeded at a density of $1\times10^5$ in 6-well plate and incubated with 10 μg EV for 72-hr after seeding. After incubation with EVs, the cells analyzed by functional assays.

Soft Agar Assay

Molten top agar (0.4% agarose, 2×DMEM, 20% FBS) mixed with $2\times10^4$ cells was overlaid on top of the bottom agar (1% agarose, 2×DMEM, 20% FBS) in 60-mm culture plate. The cell cultures were allowed to grow for 3-4 weeks. At the end of the experiment, the number of colonies was counted under inverted light microscope. Five fields were randomly selected, and number of colonies was counted.

Migration and Invasion Assays

Transwell® Permeable Supports (Corning) were used in the migration and invasion assays. For invasion assay, BD Matrigel™ Basement Membrane Matrix (BD Bioscience) was used to coat the transwell inserts prior to seeding of cells. For both assays, $7\times10^4$ cells were resuspended in serum-free medium and seeded in the upper chamber of transwells. Medium with 10% FBS was added in the bottom chamber as chemoattractant. After incubation for a pre-determined period, cells that passed through the transwell membrane were fixed and stained with crystal violet. Four fields were randomly selected and number of migrated and invaded cells was counted.

Tube Formation Assay

Growth factor-reduced Matrigel (Corning) was allowed to polymerize in a 12-well plate and EV pretreated HUVEC cells were seeded at a density of $5\times10^4$ per well in Medium 200 (Gibco™). The number of capillary tubes formed was counted in 5 random fields under a 10× objective lens using Nikon Eclipse Ts2 microscope. Images of tube formation were analyzed by NIS-Elements L imaging software (Nikon Instruments Inc.).

In Vivo Angiogenesis

PLC/PRF/5 cells of $1.5\times10^5$ were mixed with 250 μl Growth factor-reduced Matrigel (BD Bioscience) at 4° C. and injected subcutaneously (s.c.) into the back of BALB/cAnN-nu mice. Seven days after implantation, mice were sacrificed. Matrigel plugs were removed and subjected to H&E staining and immunohistochemistry staining of endothelial cell using anti-CD31 antibody (Abcam).

Quantitative Real-Time PCR Analysis

Total RNA was extracted from MRC-5 cells using RNeasy Mini Kit (QIAGEN) according to the manufacturer's instructions. Reverse transcription was performed using SuperScript™ VILO™ cDNA Synthesis Kit (Invitrogen). Real-time PCR was conducted using SYBR Green PCR Master Mix (Thermo Fisher Scientific) and performed on Applied Biosystems 7500 Fast Real-Time PCR System (Applied Biosystems). The analysis was performed in triplicate and hypoxanthine guanine phosphoribosyl transferase I (HPRT) level was used as a reference gene for the normalization of cytokine expression in different samples. The expression of cytokine is expressed as copy number per HPRT. The fold change of cytokine expression in MRC-5 treated with CTL-KD-EV and NID1-KD1-EV relative to that in MRC-5 treated with PBS is also calculated.

REFERENCES

1. D. F. Quail, J. A. Joyce, Nat Med 2013, 19, 1423.
2. J. Skog, T. Wurdinger, S. van Rijn, D. H. Meijer, L. Gainche, M. Sena-Esteves, W. T. Curry, Jr., B. S. Carter, A. M. Krichevsky, X. O. Breakefield, Nat Cell Biol 2008, 10, 1470.
3. T. Kogure, W. L. Lin, I. K. Yan, C. Braconi, T. Patel, Hepatology 2011, 54, 1237.
4. K. Al-Nedawi, B. Meehan, J. Micallef, V. Lhotak, L. May, A. Guha, J. Rak, Nat Cell Biol 2008, 10, 619.
5. J. Paggetti, F. Haderk, M. Seiffert, B. Janji, U. Distler, W. Ammerlaan, Y. J. Kim, J. Adam, P. Lichter, E. Solary, G. Berchem, E. Moussay, Blood 2015, 126, 1106.
6. B. Costa-Silva, N. M. Aiello, A. J. Ocean, S. Singh, H. Zhang, B. K. Thakur, A. Becker, A. Hoshino, M. T. Mark, H. Molina, J. Xiang, T. Zhang, T. M. Theilen, G. Garcia-Santos, C. Williams, Y. Ararso, Y. Huang, G. Rodrigues, T. L. Shen, K. J. Labori, I. M. Lothe, E. H. Kure, J. Hernandez, A. Doussot, S. H. Ebbesen, P. M. Grandgenett, M. A. Hollingsworth, M. Jain, K. Mallya, S. K. Batra, W. R. Jarnagin, R. E. Schwartz, I. Matei, H. Peinado, B. Z. Stanger, J. Bromberg, D. Lyden, Nat Cell Biol 2015, 17, 816.
7. H. Peinado, M. Aleckovic, S. Lavotshkin, I. Matei, B. Costa-Silva, G. Moreno-Bueno, M. Hergueta-Redondo, C. Williams, G. Garcia-Santos, C. Ghajar, A. Nitadori-Hoshino, C. Hoffman, K. Badal, B. A. Garcia, M. K. Callahan, J. Yuan, V. R. Martins, J. Skog, R. N. Kaplan, M. S. Brady, J. D. Wolchok, P. B. Chapman, Y. Kang, J. Bromberg, D. Lyden, Nat Med 2012, 18, 883.
8. N. Erez, M. Truitt, P. Olson, S. T. Arron, D. Hanahan, Cancer Cell 2010, 17, 135.
9. A. Costa, Y. Kieffer, A. Scholer-Dahirel, F. Pelon, B. Bourachot, M. Cardon, P. Sirven, I. Magagna, L. Fuhrmann, C. Bernard, C. Bonneau, M. Kondratova, I. Kuperstein, A. Zinovyev, A. M. Givel, M. C. Parrini, V. Soumelis, A. Vincent-Salomon, F. Mechta-Grigoriou, Cancer Cell 2018, 33, 463.
10. M. Kraman, P. J. Bambrough, J. N. Arnold, E. W. Roberts, L. Magiera, J. O. Jones, A. Gopinathan, D. A. Tuveson, D. T. Fearon, Science 2010, 330, 827.
11. E. Y. Lau, J. Lo, B. Y. Cheng, M. K. Ma, J. M. Lee, J. K. Ng, S. Chai, C. H. Lin, S. Y. Tsang, S. Ma, I. O. Ng, T. K. Lee, Cell Rep 2016, 15, 1175.
12. A. Mazzocca, E. Fransvea, F. Dituri, L. Lupo, S. Antonaci, G. Giannelli, Hepatology 2010, 51, 523.
13. C. J. Hanley, M. Mellone, K. Ford, S. M. Thirdborough, T. Mellows, S. J. Frampton, D. M. Smith, E. Harden, C. Szyndralewiez, M. Bullock, F. Noble, K. A. Moutasim, E. V. King, P. Vijayanand, A. H. Mirnezami, T. J. Underwood, C. H. Ottensmeier, G. J. Thomas, J Natl Cancer Inst 2018, 110, 109.
14. X. Y. Yang, D. Zhang, Q. F. Zou, F. Fan, F. Shen, Med Oncol 2013, 30, 593.
15. J. Ji, T. Eggert, A. Budhu, M. Forgues, A. Takai, H. Dang, Q. Ye, J. S. Lee, J. H. Kim, T. F. Greten, X. W. Wang, Hepatology 2015, 62, 481.
16. A. Duseja, Journal of clinical and experimental hepatology 2014, 4, S74.

17. F. X. Sun, Z. Y. Tang, K. D. Lui, S. L. Ye, Q. Xue, D. M. Gao, Z. C. Ma, International journal of cancer 1996, 66, 239.
18. A. Datta, H. Kim, L McGee, A. E. Johnson, S. Talwar, J. Marugan, N. Southall, X. Hu, M. Lal, D. Mondal, M. Ferrer, A. B. Abdel-Mageed, Sci Rep 2018, 8, 8161.
19. M. E. Balasis, K. D. Forinash, Y. A. Chen, W. J. Fulp, D. Coppola, A. D. Hamilton, J. Q. Cheng, S. M. Sebti, Clinical cancer research: an official journal of the American Association for Cancer Research 2011, 17, 2852.
20. B. R. Untch, V. Dos Anjos, M. E. R. Garcia-Rendueles, J. A. Knauf, G. P. Krishnamoorthy, M. Saqcena, U. K. Bhanot, N. D. Socci, A. L. Ho, R. Ghossein, J. A. Fagin, Cancer Res 2018, 78, 4642.
21. Y. Huang, N. Song, Y. Ding, S. Yuan, X. Li, H. Cai, H. Shi, Y. Luo, Cancer Res 2009, 69, 7529.
22. Y. Zhou, Y. Zhu, X. Fan, C. Zhang, Y. Wang, L. Zhang, H. Zhang, T. Wen, K. Zhang, X. Huo, X. Jiang, X. Bu, Y. Zhang, Oncotarget 2017, 8, 33110.
23. N. Pedrola, L. Devis, M. Llaurado, I. Campoy, E. Martinez-Garcia, M. Garcia, L. Muinelo-Romay, L. Alonso-Alconada, M. Abal, F. Alameda, G. Mancebo, R. Carreras, J. Castellvi, S. Cabrera, A. Gil-Moreno, X. Matias-Guiu, J. L. Iovanna, E. Colas, A. Reventos, A. Ruiz, Clinical & experimental metastasis 2015, 32, 467.
24. M. Aleckovic, Y. Wei, G. LeRoy, S. Sidoli, D. D. Liu, B. A. Garcia, Y. Kang, Genes Dev 2017, 31, 1439.
25. H. Peinado, H. Zhang, I. R. Matei, B. Costa-Silva, A. Hoshino, G. Rodrigues, B. Psaila, R. N. Kaplan, J. F. Bromberg, Y. Kang, M. J. Bissell, T. R. Cox, A. J. Giaccia, J. T. Erler, S. Hiratsuka, C. M. Ghajar, D. Lyden, Nat Rev Cancer 2017, 17, 302.
26. J. T. O'Connell, H. Sugimoto, V. G. Cooke, B. A. MacDonald, A. I. Mehta, V. S. LeBleu, R. Dewar, R. M. Rocha, R. R. Brentani, M. B. Resnick, E. G. Neilson, M. Zeisberg, R. Kalluri, Proc Natl Acad Sci U S A 2011, 108, 16002.
27. M. Q. Kwa, K. M. Herum, C. Brakebusch, Clin Exp Metastas 2019, 36, 71.
28. M. He, H. Qin, T. C. Poon, S. C. Sze, X. Ding, N. N. Co, S. M. Ngai, T. F. Chan, N. Wong, Carcinogenesis 2015, 36, 1008.
29. L. Chen, P. Guo, Y. He, Z. Chen, L. Chen, Y. Luo, L. Qi, Y. Liu, Q. Wu, Y. Cui, F. Fang, X. Zhang, T. Song, H. Guo, Cell Death Dis 2018, 9, 513.
30. X. J. Lin, J. H. Fang, X. J. Yang, C. Zhang, Y. Yuan, L. Zheng, S. M. Zhuang, Mol Ther Nucleic Acids 2018, 11, 243.
31. H. Liu, W. Chen, X. Zhi, E. J. Chen, T. Wei, J. Zhang, J. Shen, L. Q. Hu, B. Zhao, X. H. Feng, X. L. Bai, T. B. Liang, Oncogene 2018, 37, 4964.
32. J. H. Fang, Z. J. Zhang, L. R. Shang, Y. W. Luo, Y. F. Lin, Y. Yuan, S. M. Zhuang, Hepatology 2018, 68, 1459.
33. X. Fu, M. Liu, S. Qu, J. Ma, Y. Zhang, T. Shi, H. Wen, Y. Yang, S. Wang, J. Wang, K. Nan, Y. Yao, T. Tian, J Exp Clin Cancer Res 2018, 37, 52.
34. T. Fang, H. Lv, G. Lv, T. Li, C. Wang, Q. Han, L. Yu, B. Su, L. Guo, S. Huang, D. Cao, L. Tang, S. Tang, M. Wu, W. Yang, H. Wang, Nat Commun 2018, 9, 191.
35. J. Liu, L. Fan, H. Yu, J. Zhang, Y. He, D. Feng, F. Wang, X. Li, Q. Liu, Y. Li, Z. Guo, B. Gao, W. Wei, H. Wang, G. Sun, Hepatology 2019, 70, 241.
36. S. Zhao, J. Li, G. Zhang, Q. Wang, C. Wu, Q. Zhang, H. Wang, P. Sun, R. Xiang, S. Yang, Cell Physiol Biochem 2019, 53, 19.
37. Y. Wang, B. Wang, S. Xiao, Y. Li, Q. Chen, J Cell Biochem 2019, 120, 3046.
38. J. Zhang, S. Lu, Y. Zhou, K. Meng, Z. Chen, Y. Cui, Y. Shi, T. Wang, Q. Y. He, Proteomics 2017, 17, 1700103.
39. C. J. Ko, C. C. Huang, H. Y. Lin, C. P. Juan, S. W. Lan, H. Y. Shyu, S. R. Wu, P. W. Hsiao, H. P. Huang, C. T. Shun, M. S. Lee, Cancer Res 2015, 75, 2949.
40. D. A. Ferraro, F. Patella, S. Zanivan, C. Donato, N. Aceto, M. Giannotta, E. Dejana, M. Diepenbruck, G. Christofori, M. Buess, BMC Cancer 2019, 19, 312.
41. I. Lazar, E. Clement, M. Ducoux-Petit, L. Denat, V. Soldan, S. Dauvillier, S. Balor, O. Burlet-Schiltz, L. Lame, C. Muller, L. Nieto, Pigment Cell Melanoma Res 2015, 28, 464.
42. Y. K. Chan, H. Zhang, P. Liu, S. W. Tsao, M. L. Lung, N. K. Mak, R. Ngok-Shun Wong, P. Ying-Kit Yue, Int J Cancer 2015, 137, 1830.
43. P. A. Gonzales, T. Pisitkun, J. D. Hoffert, D. Tchapyjnikov, R. A. Star, R. Kleta, N. S. Wang, M. A. Knepper, J Am Soc Nephrol 2009, 20, 363.
44. H. Nakagawa, A. Umemura, K. Taniguchi, J. Font-Burgada, D. Dhar, H. Ogata, Z. Zhong, M. A. Valasek, E. Seki, J. Hidalgo, K. Koike, R. J. Kaufman, M. Karin, Cancer Cell 2014, 26, 331.
45. F. I. Hawari, F. N. Rouhani, X. Cui, Z. X. Yu, C. Buckley, M. Kaler, S. J. Levine, Proc Natl Acad Sci U S A 2004, 101, 1297.
46. J. H. Bell, A. H. Herrera, Y. Li, B. Walcheck, J Leukoc Biol 2007, 82, 173.
47. A. Murthy, V. Defamie, D. S. Smookler, M. A. Di Grappa, K. Horiuchi, M. Federici, M. Sibilia, C. P. Blobel, R. Khokha, J Clin Invest 2010, 120, 2731.
48. A. N. Abety, J. W. Fox, A. Schonefuss, J. Zamek, J. Landsberg, T. Krieg, C. Blobel, C. Mauch, P. Zigrino, J Invest Dermatol 2012, 132, 2451.
49. L. Dossus, S. Becker, S. Rinaldi, A. Lukanova, A. Tjonneland, A. Olsen, K. Overvad, N. Chabbert-Buffet, M. C. Boutron-Ruault, F. Clavel-Chapelon, B. Teucher, J. Chang-Claude, T. Pischon, H. Boeing, A. Trichopoulou, V. Benetou, E. Valanou, D. Palli, S. Sieri, R. Tumino, C. Sacerdote, R. Galasso, M. L. Redondo, C. B. Bonet, E. Molina-Montes, J. M. Altzibar, M. D. Chirlaque, E. Ardanaz, H. B. Bueno-de-Mesquita, F. J. van Duijnhoven, P. H. Peeters, N. C. Onland-Moret, E. Lundin, A. Idahl, K. T. Khaw, N. Wareham, N. Allen, I. Romieu, V. Fedirko, P. Hainaut, D. Romaguera, T. Norat, E. Riboli, R. Kaaks, Int J Cancer 2011, 129, 2032.
50. M. S. Ahluwalia, S. Bou-Anak, M. E. Burgett, N. Sarmey, D. Khosla, S. Dahiya, R. J. Weil, E. Bae, P. Huang, M. McGraw, L. M. Grove, M. A. Olman, R. A. Prayson, J. H. Suh, G. Y. Gillespie, J. Barnholtz-Sloan, A. S. Nowacki, G. H. Barnett, C. L. Gladson, J Neurooncol 2017, 131, 449.
51. J. Berg, A. R. Halvorsen, M. B. Bengtson, K. A. Tasken, G. M. Maelandsmo, A. Yndestad, B. Halvorsen, O. T. Brustugun, P. Aukrust, T. Ueland, A. Helland, BMC Cancer 2018, 18, 739.
52. A. C. Carlsson, C. C. Juhlin, T. E. Larsson, A. Larsson, E. Ingelsson, J. Sundstrom, L. Lind, J. Arnlov, Atherosclerosis 2014, 237, 236.
53. G. B. McDonald, L. Tabellini, B. E. Storer, R. L. Lawler, P. J. Martin, J. A. Hansen, Blood 2015, 126, 113.
54. Y. Zhang, B. Xu, Y. Liu, H. Yao, N. Lu, B. Li, J. Gao, S. Guo, N. Han, J. Qi, K. Zhang, S. Cheng, H. Wang, X. Zhang, T. Xiao, L. Wu, Y. Gao, Proteomics 2012, 12, 1883.
55. C. W. Hsu, K. P. Chang, Y. Huang, H. P. Liu, P. C. Hsueh, P. W. Gu, W. C. Yen, C. C. Wu, Mol Cell Proteomics 2019, 18, 1939.

56. F. Bertrand, A. Montfort, E. Marcheteau, C. Imbert, J. Gilhodes, T. Filleron, P. Rochaix, N. Andrieu-Abadie, T. Levade, N. Meyer, C. Colacios, B. Segui, Nat Commun 2017, 8, 2256.
57. F. Van Hauwermeiren, M. Armaka, N. Karagianni, K. Kranidioti, R. E. Vandenbroucke, S. Loges, M. Van Roy, J. Staelens, L. Puimege, A. Palagani, W. V. Berghe, P. Victoratos, P. Carmeliet, C. Libert, G. Kollias, J Clin Invest 2013, 123, 2590.
58. L. Niu, L. Liu, S. Yang, J. Ren, P. B. S. Lai, G. G. Chen, Biochim Biophys Acta Rev Cancer 2017, 1868, 564.
59. L. Hu, J. M. Wen, J. S. Sham, W. Wang, D. Xie, W. M. Tjia, J. F. Huang, M. Zhang, W. F. Zeng, X. Y. Guan, Cancer Genet Cytogenet 2004, 148, 80.
60. J. J. Brown, B. Parashar, H. Moshage, K. E. Tanaka, D. Engelhardt, E. Rabbani, N. Roy-Chowdhury, J. Roy-Chowdhury, Hepatology 2000, 31, 173.
61. W. Xue, T. Kitzing, S. Roessler, J. Zuber, A. Krasnitz, N. Schultz, K. Revill, S. Weissmueller, A. R. Rappaport, J. Simon, J. Zhang, W. Luo, J. Hicks, L. Zender, X. W. Wang, S. Powers, M. Wigler, S. W. Lowe, Proc Natl Acad Sci U S A 2012, 109, 8212.
62. Y. Perez-Riverol, A. Csordas, J. Bai, M. Bernal-Llinares, S. Hewapathirana, D. J. Kundu, A. Inuganti, J. Griss, G. Mayer, M. Eisenacher, E. Perez, J. Uszkoreit, J. Pfeuffer, T. Sachsenberg, S. Yilmaz, S. Tiwary, J. Cox, E. Audain, M. Walzer, A. F. Jarnuczak, T. Ternent, A. Brazma, J. A. Vizcaino, Nucleic Acids Res 2019, 47, D442.

The patent or application file contains at least one drawing executed in color. Copies of this patent or patent application publication with color drawings will be provided by the Office upon request and payment of the necessary fee.

The foregoing description of the specific embodiments will so fully reveal the general nature of the disclosure that others can, by applying knowledge within the skill of the relevant art(s) (including the contents of the documents cited and incorporated by reference herein), readily modify and/or adapt for various applications such specific embodiments, without undue experimentation, without departing from the general concept of the present disclosure. Such adaptations and modifications are therefore intended to be within the meaning and range of equivalents of the disclosed embodiments, based on the teaching and guidance presented herein.

It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).While various embodiments of the present disclosure have been described above, it should be understood that they have been presented by way of examples, and not limitation. It would be apparent to one skilled in the relevant art(s) that various changes in form and detail could be made therein without departing from the spirit and scope of the disclosure. Thus, the present disclosure should not be limited by any of the above-described exemplary embodiments, but should be defined only in accordance with the following claims and their equivalents.

What is claimed:

1. A method of treating cancer in a subject in need thereof comprising administering an effective dose of anti-nidogen 1 (NID1) monoclonal antibody to the subject,
   wherein the NID1 monoclonal antibody binds an epitope selected from the group consisting of PSRDPDQGKRN (SEQ ID NO:33), YKALRRGGADTY (SEQ ID NO:34), ERDGASPSRIYT (SEQ ID NO:35), VHDDSRPALPST (SEQ ID NO:36), EGNTMRKTEAKA (SEQ ID NO:37), and AISKETDAFQPH (SEQ ID NO:38);
   wherein the NID1 monoclonal antibody is produced by hybridoma cell line 34858-1-4/2N2, deposited with American Type Culture Collection, Patent Depository—PO083151 10801; and
   wherein the cancer is an extrahepatic metastatic cancer.

2. The method of claim 1, wherein the method further comprising administering an effective dose of anti-TNFR1 antibody.

3. The method of claim 1, wherein the extrahepatic metastatic cancer cancer is hepatocellular carcinoma ("HCC").

4. The method of claim 1, wherein the NID1 monoclonal antibody is derived from metastatic HCC cells or sera of HCC late-stage patient.

5. The method of claim 1, wherein the NID1 monoclonal antibody is derived from ascites no. 1 to 14 anti-NID1 antibodies and binds the epitope VHDDSRPALPST (SEQ ID NO:36).

6. The method of claim 1, wherein the extrahepatic metastatic cancer is a hepatic cancer that has metastasized to a tissue selected from the group consisting of lung, breast, oral cavity, ovary and rectum.

7. The method of claim 1, wherein the NID1 monoclonal antibody: (i) suppresses the effect of HCC in extracellular vesicles ("EVs"); (ii) decreases HCC cell growth; (iii) decreases HCC motility; (iv) reduces HCC colonization of cells; (v) decreases pre-metastatic niche formation; (vi) decreases angiogenesis; (vii) decreases pulmonary endothelial permeability; (viii) reduces extrahepatic metastasis, or a combination thereof.

8. A NID1 monoclonal antibody produced by hybridoma cell line 34858-1-4/2N2 deposited with American Type Culture Collection, Patent Depository—PO08315110801 .

9. A composition comprising NID1 monoclonal antibody of claim 8 and a pharmaceutical acceptable carrier.

10. A kit for the diagnosis of HCC comprising in separate containers NID1 monoclonal antibody and fragments thereof of claim 8 and a reagent for detecting NID1 monoclonal antibody binding to NID1.

11. The kit of claim 10, further comprising in separate containers TNFR1 monoclonal antibodies and a reagent for detecing TNFR1 monoclonal antibody binding to TNFR1.

12. The kit of claim 10, wherein the NID1 monoclonal antibody produced by hybridoma cell line 34858-1-4/2N2 deposited with American Type Culture Collection, Patent Depository—PO08315110801.

13. A hybridoma cell line 34858-1-4/2N2 deposited with American Type Culture Collection, Patent Depository—PO08315110801.

* * * * *

SEQUENCE LISTING

```
<160> NUMBER OF SEQ ID NOS: 40

<210> SEQ ID NO 1
<211> LENGTH: 20
<212> TYPE: DNA
<213> ORGANISM: Artificial Sequence
<220> FEATURE:
<223> OTHER INFORMATION: NID1-3111F Forward

<400> SEQUENCE: 1
gatgaattcc gtggttgctc                                              20

<210> SEQ ID NO 2
<211> LENGTH: 32
<212> TYPE: DNA
<213> ORGANISM: Artificial Sequence
<220> FEATURE:
<223> OTHER INFORMATION: NID1-stopR Reverse

<400> SEQUENCE: 2
ctagctagct catttctgtt cgatacagtc aa                                32

<210> SEQ ID NO 3
<211> LENGTH: 21
<212> TYPE: DNA
<213> ORGANISM: Artificial Sequence
<220> FEATURE:
<223> OTHER INFORMATION: IGFBP1-F Forward

<400> SEQUENCE: 3
ttgggacgcc atcagtacct a                                            21

<210> SEQ ID NO 4
<211> LENGTH: 23
```

<212> TYPE: DNA
<213> ORGANISM: Artificial Sequence
<220> FEATURE:
<223> OTHER INFORMATION: IGFBP1-R Reverse

<400> SEQUENCE: 4
ttggctaaac tctctacgac tct                                      23

<210> SEQ ID NO 5
<211> LENGTH: 21
<212> TYPE: DNA
<213> ORGANISM: Artificial Sequence
<220> FEATURE:
<223> OTHER INFORMATION: SCFD1-F Forward

<400> SEQUENCE: 5
atgcagcgtt agcagctagt g                                        21

<210> SEQ ID NO 6
<211> LENGTH: 22
<212> TYPE: DNA
<213> ORGANISM: Artificial Sequence
<220> FEATURE:
<223> OTHER INFORMATION: SCFD1-R Reverse

<400> SEQUENCE: 6
ggcctgttaa tggcacgata tg                                       22

<210> SEQ ID NO 7
<211> LENGTH: 21
<212> TYPE: DNA
<213> ORGANISM: Artificial Sequence
<220> FEATURE:
<223> OTHER INFORMATION: TNFRSF1A-F Forward

<400> SEQUENCE: 7
tcaccgcttc agaaaaccac c                                        21

<210> SEQ ID NO 8
<211> LENGTH: 21
<212> TYPE: DNA
<213> ORGANISM: Artificial Sequence
<220> FEATURE:
<223> OTHER INFORMATION: TNFRSF1A-R Reverse

<400> SEQUENCE: 8
ggtccactgt gcaagaagag a                                        21

<210> SEQ ID NO 9
<211> LENGTH: 21
<212> TYPE: DNA
<213> ORGANISM: Artificial Sequence
<220> FEATURE:
<223> OTHER INFORMATION: TIMP2-F Forward

<400> SEQUENCE: 9
aagcggtcag tgagaaggaa g                                        21

<210> SEQ ID NO 10
<211> LENGTH: 23
<212> TYPE: DNA
<213> ORGANISM: Artificial Sequence
<220> FEATURE:
<223> OTHER INFORMATION: TIMP2-R Reverse

<400> SEQUENCE: 10

```
ggggccgtgt agataaactc tat                                            23
```

\<210\> SEQ ID NO 11
\<211\> LENGTH: 19
\<212\> TYPE: DNA
\<213\> ORGANISM: Artificial Sequence
\<220\> FEATURE:
\<223\> OTHER INFORMATION: TNFRSF11B-F Forward

\<400\> SEQUENCE: 11

```
gcgctcgtgt ttctggaca                                                 19
```

\<210\> SEQ ID NO 12
\<211\> LENGTH: 23
\<212\> TYPE: DNA
\<213\> ORGANISM: Artificial Sequence
\<220\> FEATURE:
\<223\> OTHER INFORMATION: TNFRSF11B-R Reverse

\<400\> SEQUENCE: 12

```
agtatagaca ctcgtcactg gtg                                            23
```

\<210\> SEQ ID NO 13
\<211\> LENGTH: 21
\<212\> TYPE: DNA
\<213\> ORGANISM: Artificial Sequence
\<220\> FEATURE:
\<223\> OTHER INFORMATION: IGF1-F Forward

\<400\> SEQUENCE: 13

```
gctcttcagt tcgtgtgtgg a                                              21
```

\<210\> SEQ ID NO 14
\<211\> LENGTH: 21
\<212\> TYPE: DNA
\<213\> ORGANISM: Artificial Sequence
\<220\> FEATURE:
\<223\> OTHER INFORMATION: IGF1-R Reverse

\<400\> SEQUENCE: 14

```
gcctccttag atcacagctc c                                              21
```

\<210\> SEQ ID NO 15
\<211\> LENGTH: 21
\<212\> TYPE: DNA
\<213\> ORGANISM: Artificial Sequence
\<220\> FEATURE:
\<223\> OTHER INFORMATION: IGFBP2-F Forward

\<400\> SEQUENCE: 15

```
gacaatggcg atgaccactc a                                              21
```

\<210\> SEQ ID NO 16
\<211\> LENGTH: 21
\<212\> TYPE: DNA
\<213\> ORGANISM: Artificial Sequence
\<220\> FEATURE:
\<223\> OTHER INFORMATION: IGFBP2-R Reverse

\<400\> SEQUENCE: 16

```
cagctccttc atacccgact t                                              21
```

\<210\> SEQ ID NO 17
\<211\> LENGTH: 19
\<212\> TYPE: DNA
\<213\> ORGANISM: Artificial Sequence

```
<220> FEATURE:
<223> OTHER INFORMATION: TNFRSF10D-F Forward

<400> SEQUENCE: 17
taccacgacc agagacacc                                               19

<210> SEQ ID NO 18
<211> LENGTH: 20
<212> TYPE: DNA
<213> ORGANISM: Artificial Sequence
<220> FEATURE:
<223> OTHER INFORMATION: TNFRSF10D-R Reverse

<400> SEQUENCE: 18
caccctgttc tacacgtccg                                              20

<210> SEQ ID NO 19
<211> LENGTH: 21
<212> TYPE: DNA
<213> ORGANISM: Artificial Sequence
<220> FEATURE:
<223> OTHER INFORMATION: TGFB3-F Forward

<400> SEQUENCE: 19
acttgcacca ccttggactt c                                            21

<210> SEQ ID NO 20
<211> LENGTH: 19
<212> TYPE: DNA
<213> ORGANISM: Artificial Sequence
<220> FEATURE:
<223> OTHER INFORMATION: TGFB3-R Reverse

<400> SEQUENCE: 20
ggtcatcacc gttggctca                                               19

<210> SEQ ID NO 21
<211> LENGTH: 21
<212> TYPE: DNA
<213> ORGANISM: Artificial Sequence
<220> FEATURE:
<223> OTHER INFORMATION: LEP-F Forward

<400> SEQUENCE: 21
tgccttccag aaacgtgatc c                                            21

<210> SEQ ID NO 22
<211> LENGTH: 21
<212> TYPE: DNA
<213> ORGANISM: Artificial Sequence
<220> FEATURE:
<223> OTHER INFORMATION: LEP-R Reverse

<400> SEQUENCE: 22
ctctgtggag tagcctgaag c                                            21

<210> SEQ ID NO 23
<211> LENGTH: 22
<212> TYPE: DNA
<213> ORGANISM: Artificial Sequence
<220> FEATURE:
<223> OTHER INFORMATION: TNFSF14-F Forward

<400> SEQUENCE: 23
atacaagagc gaaggtctca cg                                           22
```

<210> SEQ ID NO 24
<211> LENGTH: 21
<212> TYPE: DNA
<213> ORGANISM: Artificial Sequence
<220> FEATURE:
<223> OTHER INFORMATION: TNFSF14-R Reverse

<400> SEQUENCE: 24
ctgagtctcc cataacagcg g                                              21

<210> SEQ ID NO 25
<211> LENGTH: 21
<212> TYPE: DNA
<213> ORGANISM: Artificial Sequence
<220> FEATURE:
<223> OTHER INFORMATION: FGF6-F Forward

<400> SEQUENCE: 25
tggctatttg gtggggatca a                                              21

<210> SEQ ID NO 26
<211> LENGTH: 21
<212> TYPE: DNA
<213> ORGANISM: Artificial Sequence
<220> FEATURE:
<223> OTHER INFORMATION: FGF6-R Reverse

<400> SEQUENCE: 26
gaagagggca cttctcactc c                                              21

<210> SEQ ID NO 27
<211> LENGTH: 22
<212> TYPE: DNA
<213> ORGANISM: Artificial Sequence
<220> FEATURE:
<223> OTHER INFORMATION: TNF-alpha Forward

<400> SEQUENCE: 27
cttctgcctg ctgcactttg ga                                             22

<210> SEQ ID NO 28
<211> LENGTH: 22
<212> TYPE: DNA
<213> ORGANISM: Artificial Sequence
<220> FEATURE:
<223> OTHER INFORMATION: TNF-alpha Reverse

<400> SEQUENCE: 28
tcccaaagta gacctgccca ga                                             22

<210> SEQ ID NO 29
<211> LENGTH: 20
<212> TYPE: DNA
<213> ORGANISM: Artificial Sequence
<220> FEATURE:
<223> OTHER INFORMATION: ADIPOQ-F Forward

<400> SEQUENCE: 29
tgctgggagc tgttctactg                                                20

<210> SEQ ID NO 30
<211> LENGTH: 21
<212> TYPE: DNA
<213> ORGANISM: Artificial Sequence
<220> FEATURE:
<223> OTHER INFORMATION: ADIPOQ-R Reverse

```
<400> SEQUENCE: 30
tactccggtt tcaccgatgt c                                              21

<210> SEQ ID NO 31
<211> LENGTH: 21
<212> TYPE: DNA
<213> ORGANISM: Artificial Sequence
<220> FEATURE:
<223> OTHER INFORMATION: HPRT-F Forward

<400> SEQUENCE: 31
cctggcgtcg tgattagtga t                                              21

<210> SEQ ID NO 32
<211> LENGTH: 22
<212> TYPE: DNA
<213> ORGANISM: Artificial Sequence
<220> FEATURE:
<223> OTHER INFORMATION: HPRT-R Reverse

<400> SEQUENCE: 32
agacgttcag tcctgtccat aa                                             22

<210> SEQ ID NO 33
<211> LENGTH: 12
<212> TYPE: PRT
<213> ORGANISM: Artificial Sequence
<220> FEATURE:
<223> OTHER INFORMATION: Epitope Sequence

<400> SEQUENCE: 33

Pro Ser Arg Asp Pro Asp Gln Lys Gly Lys Arg Asn
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Epitope Sequence

<400> SEQUENCE: 34

Tyr Lys Ala Leu Arg Arg Gly Gly Ala Asp Thr Tyr
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Epitope Sequence

<400> SEQUENCE: 35

Glu Arg Asp Gly Ala Ser Pro Ser Arg Ile Tyr Thr
1               5                   10

<210> SEQ ID NO 36
<211> LENGTH: 12
<212> TYPE: PRT
<213> ORGANISM: Artificial Sequence
<220> FEATURE:
<223> OTHER INFORMATION: Epitope Sequence

<400> SEQUENCE: 36

Val His Asp Asp Ser Arg Pro Ala Leu Pro Ser Thr
```

-continued

```
<210> SEQ ID NO 37
<211> LENGTH: 12
<212> TYPE: PRT
<213> ORGANISM: Artificial Sequence
<220> FEATURE:
<223> OTHER INFORMATION: Epitope Sequence

<400> SEQUENCE: 37

Glu Gly Asn Thr Met Arg Lys Thr Glu Ala Lys Ala
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Epitope Sequence

<400> SEQUENCE: 38

Ala Ile Ser Lys Glu Thr Asp Ala Phe Gln Pro His
1               5                   10

<210> SEQ ID NO 39
<211> LENGTH: 1247
<212> TYPE: PRT
<213> ORGANISM: Artificial Sequence
<220> FEATURE:
<223> OTHER INFORMATION: Nidogen-1 (NID1) amino acid sequence

<400> SEQUENCE: 39

Met Leu Ala Ser Ser Arg Ile Arg Ala Ala Trp Thr Arg Ala Leu
1               5                   10                  15

Leu Leu Pro Leu Leu Ala Gly Pro Val Gly Cys Leu Ser Arg Gln
                20                  25                  30

Glu Leu Phe Pro Phe Gly Pro Gly Gln Gly Asp Leu Glu Leu Glu Asp
            35                  40                  45

Gly Asp Asp Phe Val Ser Pro Ala Leu Glu Leu Ser Gly Ala Leu Arg
        50                  55                  60

Phe Tyr Asp Arg Ser Asp Ile Asp Ala Val Tyr Val Thr Thr Asn Gly
65                  70                  75                  80

Ile Ile Ala Thr Ser Glu Pro Pro Ala Lys Glu Ser His Pro Gly Leu
                85                  90                  95

Phe Pro Pro Thr Phe Gly Ala Val Ala Pro Phe Leu Ala Asp Leu Asp
            100                 105                 110

Thr Thr Asp Gly Leu Gly Lys Val Tyr Tyr Arg Glu Asp Leu Ser Pro
        115                 120                 125

Ser Ile Thr Gln Arg Ala Ala Glu Cys Val His Arg Gly Phe Pro Glu
    130                 135                 140

Ile Ser Phe Gln Pro Ser Ser Ala Val Val Thr Trp Glu Ser Val
145                 150                 155                 160

Ala Pro Tyr Gln Gly Pro Ser Arg Asp Pro Asp Gln Lys Gly Lys Arg
                165                 170                 175

Asn Thr Phe Gln Ala Val Leu Ala Ser Ser Asp Ser Ser Ser Tyr Ala
            180                 185                 190

Ile Phe Leu Tyr Pro Glu Asp Gly Leu Gln Phe His Thr Thr Phe Ser
        195                 200                 205

Lys Lys Glu Asn Asn Gln Val Pro Ala Val Val Ala Phe Ser Gln Gly
    210                 215                 220
```

```
Ser Val Gly Phe Leu Trp Lys Ser Asn Gly Ala Tyr Asn Ile Phe Ala
225                 230                 235                 240

Asn Asp Arg Glu Ser Val Glu Asn Leu Ala Lys Ser Ser Asn Ser Gly
            245                 250                 255

Gln Gln Gly Val Trp Val Phe Glu Ile Gly Ser Pro Ala Thr Thr Asn
            260                 265                 270

Gly Val Pro Ala Asp Val Ile Leu Gly Thr Glu Asp Gly Ala Glu
            275                 280                 285

Tyr Asp Asp Glu Asp Glu Asp Tyr Asp Leu Ala Thr Thr Arg Leu Gly
            290                 295                 300

Leu Glu Asp Val Gly Thr Thr Pro Phe Ser Tyr Lys Ala Leu Arg Arg
305                 310                 315                 320

Gly Gly Ala Asp Thr Tyr Ser Val Pro Ser Val Leu Ser Pro Arg Arg
            325                 330                 335

Ala Ala Thr Glu Arg Pro Leu Gly Pro Pro Thr Glu Arg Thr Arg Ser
            340                 345                 350

Phe Gln Leu Ala Val Glu Thr Phe His Gln His Pro Gln Val Ile
            355                 360                 365

Asp Val Asp Glu Val Glu Glu Thr Gly Val Val Phe Ser Tyr Asn Thr
            370                 375                 380

Asp Ser Arg Gln Thr Cys Ala Asn Asn Arg His Gln Cys Ser Val His
385                 390                 395                 400

Ala Glu Cys Arg Asp Tyr Ala Thr Gly Phe Cys Cys Ser Cys Val Ala
                405                 410                 415

Gly Tyr Thr Gly Asn Gly Arg Gln Cys Val Ala Glu Gly Ser Pro Gln
            420                 425                 430

Arg Val Asn Gly Lys Val Lys Gly Arg Ile Phe Val Gly Ser Ser Gln
            435                 440                 445

Val Pro Ile Val Phe Glu Asn Thr Asp Leu His Ser Tyr Val Val Met
450                 455                 460

Asn His Gly Arg Ser Tyr Thr Ala Ile Ser Thr Ile Pro Glu Thr Val
465                 470                 475                 480

Gly Tyr Ser Leu Leu Pro Leu Ala Pro Val Gly Gly Ile Ile Gly Trp
            485                 490                 495

Met Phe Ala Val Glu Gln Asp Gly Phe Lys Asn Gly Phe Ser Ile Thr
            500                 505                 510

Gly Gly Glu Phe Thr Arg Gln Ala Glu Val Thr Phe Val Gly His Pro
            515                 520                 525

Gly Asn Leu Val Ile Lys Gln Arg Phe Ser Gly Ile Asp Glu His Gly
            530                 535                 540

His Leu Thr Ile Asp Thr Glu Leu Glu Gly Arg Val Pro Gln Ile Pro
545                 550                 555                 560

Phe Gly Ser Ser Val His Ile Glu Pro Tyr Thr Glu Leu Tyr His Tyr
                565                 570                 575

Ser Thr Ser Val Ile Thr Ser Ser Thr Arg Glu Tyr Thr Val Thr
            580                 585                 590

Glu Pro Glu Arg Asp Gly Ala Ser Pro Ser Arg Ile Tyr Thr Tyr Gln
            595                 600                 605

Trp Arg Gln Thr Ile Thr Phe Gln Glu Cys Val His Asp Asp Ser Arg
            610                 615                 620

Pro Ala Leu Pro Ser Thr Gln Gln Leu Ser Val Asp Ser Val Phe Val
625                 630                 635                 640
```

```
Leu Tyr Asn Gln Glu Glu Lys Ile Leu Arg Tyr Ala Leu Ser Asn Ser
                645                 650                 655

Ile Gly Pro Val Arg Glu Gly Ser Pro Asp Ala Leu Gln Asn Pro Cys
        660                 665                 670

Tyr Ile Gly Thr His Gly Cys Asp Thr Asn Ala Ala Cys Arg Pro Gly
    675                 680                 685

Pro Arg Thr Gln Phe Thr Cys Glu Cys Ser Ile Gly Phe Arg Gly Asp
690                 695                 700

Gly Arg Thr Cys Tyr Asp Ile Asp Glu Cys Ser Glu Gln Pro Ser Val
705                 710                 715                 720

Cys Gly Ser His Thr Ile Cys Asn Asn His Pro Gly Thr Phe Arg Cys
                725                 730                 735

Glu Cys Val Glu Gly Tyr Gln Phe Ser Asp Glu Gly Thr Cys Val Ala
        740                 745                 750

Val Val Asp Gln Arg Pro Ile Asn Tyr Cys Glu Thr Gly Leu His Asn
    755                 760                 765

Cys Asp Ile Pro Gln Arg Ala Gln Cys Ile Tyr Thr Gly Gly Ser Ser
770                 775                 780

Tyr Thr Cys Ser Cys Leu Pro Gly Phe Ser Gly Asp Gly Gln Ala Cys
785                 790                 795                 800

Gln Asp Val Asp Glu Cys Gln Pro Ser Arg Cys His Pro Asp Ala Phe
                805                 810                 815

Cys Tyr Asn Thr Pro Gly Ser Phe Thr Cys Gln Cys Lys Pro Gly Tyr
        820                 825                 830

Gln Gly Asp Gly Phe Arg Cys Val Pro Gly Glu Val Glu Lys Thr Arg
    835                 840                 845

Cys Gln His Glu Arg Glu His Ile Leu Gly Ala Ala Gly Ala Thr Asp
850                 855                 860

Pro Gln Arg Pro Ile Pro Pro Gly Leu Phe Val Pro Glu Cys Asp Ala
865                 870                 875                 880

His Gly His Tyr Ala Pro Thr Gln Cys His Gly Ser Thr Gly Tyr Cys
                885                 890                 895

Trp Cys Val Asp Arg Asp Gly Arg Glu Val Glu Gly Thr Arg Thr Arg
        900                 905                 910

Pro Gly Met Thr Pro Pro Cys Leu Ser Thr Val Ala Pro Pro Ile His
    915                 920                 925

Gln Gly Pro Ala Val Pro Thr Ala Val Ile Pro Leu Pro Pro Gly Thr
930                 935                 940

His Leu Leu Phe Ala Gln Thr Gly Lys Ile Glu Arg Leu Pro Leu Glu
945                 950                 955                 960

Gly Asn Thr Met Arg Lys Thr Glu Ala Lys Ala Phe Leu His Val Pro
                965                 970                 975

Ala Lys Val Ile Ile Gly Leu Ala Phe Asp Cys Val Asp Lys Met Val
        980                 985                 990

Tyr Trp Thr Asp Ile Thr Glu Pro Ser Ile Gly Arg Ala Ser Leu His
    995                 1000                1005

Gly Gly Glu Pro Thr Thr Ile Ile Arg Gln Asp Leu Gly Ser Pro
    1010                1015                1020

Glu Gly Ile Ala Val Asp His Leu Gly Arg Asn Ile Phe Trp Thr
    1025                1030                1035

Asp Ser Asn Leu Asp Arg Ile Glu Val Ala Lys Leu Asp Gly Thr
    1040                1045                1050

Gln Arg Arg Val Leu Phe Glu Thr Asp Leu Val Asn Pro Arg Gly
```

```
            1055                1060                1065
Ile Val Thr Asp Ser Val Arg Gly Asn Leu Tyr Trp Thr Asp Trp
            1070                1075                1080

Asn Arg Asp Asn Pro Lys Ile Glu Thr Ser Tyr Met Asp Gly Thr
            1085                1090                1095

Asn Arg Arg Ile Leu Val Gln Asp Asp Leu Gly Leu Pro Asn Gly
            1100                1105                1110

Leu Thr Phe Asp Ala Phe Ser Ser Gln Leu Cys Trp Val Asp Ala
            1115                1120                1125

Gly Thr Asn Arg Ala Glu Cys Leu Asn Pro Ser Gln Pro Ser Arg
            1130                1135                1140

Arg Lys Ala Leu Glu Gly Leu Gln Tyr Pro Phe Ala Val Thr Ser
            1145                1150                1155

Tyr Gly Lys Asn Leu Tyr Phe Thr Asp Trp Lys Met Asn Ser Val
            1160                1165                1170

Val Ala Leu Asp Leu Ala Ile Ser Lys Glu Thr Asp Ala Phe Gln
            1175                1180                1185

Pro His Lys Gln Thr Arg Leu Tyr Gly Ile Thr Thr Ala Leu Ser
            1190                1195                1200

Gln Cys Pro Gln Gly His Asn Tyr Cys Ser Val Asn Asn Gly Gly
            1205                1210                1215

Cys Thr His Leu Cys Leu Ala Thr Pro Gly Ser Arg Thr Cys Arg
            1220                1225                1230

Cys Pro Asp Asn Thr Leu Gly Val Asp Cys Ile Glu Gln Lys
            1235                1240                1245
```

<210> SEQ ID NO 40
<211> LENGTH: 5792
<212> TYPE: DNA
<213> ORGANISM: Artificial Sequence
<220> FEATURE:
<223> OTHER INFORMATION: Nidogen-1 (NID1) nucleotide sequence

<400> SEQUENCE: 40

```
agttcgggaa catgttggcc tcgagcagcc ggatccgggc tgcgtggacg cgggcgctgc    60
tgctgccgct gctgctggcg gggcctgtgg gctgcctgag ccgccaggag ctctttccct   120
tcggccccgg acaggggac ctggagctgg aggacgggga tgacttcgtc tctcctgccc    180
tggagctgag tggggcgctc cgcttctacg acagatccga catcgacgca gtctacgtca   240
ccacaaatgg catcattgct acgagtgaac ccccggccaa agaatcccat cccgggctct   300
tcccaccaac attcggtgca gtcgccccctt tcctggcgga cttggacacg accgatggcc   360
tggggaaggt ttattatcga aagacttat ccccctccat cactcagcga gcagcagagt   420
gtgtccacag agggttcccg agatctctt tccagcctag tagcgcggtg gttgtcactt   480
gggaatccgt ggcccctac caagggccca gcagggaccc agaccagaaa ggcaagagaa   540
acacgttcca ggctgttcta gcctcctctg attccagctc ctatgccatt ttcctttatc   600
ctgaggatgg tctgcagttc catacgacat tctcaaagaa ggaaaacaac caagttcctg   660
ccgtggtttgc attcagtcaa ggttcagtgg gattcttatg gaagagcaac ggagcttata   720
acatatttgc taatgacagg gaatcagttg aaaatttggc caagagtagt aactctgggc   780
agcagggtgt ctgggtgttt gagattggga gtccagccac accaatggc gtggtgcctg   840
cagacgtgat cctcggaact gaagatgggg cagagtatga tgatgaggat gaagattatg   900
acctggcgac cactcgtcctg ggcctggagg atgtgggcac cacgcccttc tcctacaagg   960
```

```
ctctgagaag gggaggtgct gacacataca gtgtgcccag cgtcctctcc ccgcgccggg    1020
cagctaccga aaggcccctt ggacctccca cagagagaac caggtctttc cagttggcag    1080
tggagacttt tcaccagcag caccctcagg tcatagatgt ggatgaagtt gaggaaacag    1140
gagttgtttt cagctataac acggattccc gccagacgtg tgctaacaac agacaccagt    1200
gctcggtgca cgcagagtgc agggactacg ccacgggctt ctgctgcagc tgtgtcgctg    1260
gctatacggg caatggcagg caatgtgttg cagaaggttc cccccagcga gtcaatggca    1320
aggtgaaagg aaggatcttt gtggggagca gccaggtccc cattgtcttt gagaacactg    1380
acctccactc ttacgtagta atgaaccacg gcgctccta cacagccatc agcaccattc      1440
ccgagaccgt tggatattct ctgcttccac tggccccagt tggaggcatc attggatgga    1500
tgtttgcagt ggagcaggac ggattcaaga atgggttcag catcaccggg ggtgagttca    1560
ctcgccaggc tgaggtgacc ttcgtggggc acccgggcaa tctggtcatt aagcagcggt    1620
tcagcggcat cgatgagcat gggcacctga ccatcgacac ggagctggag ggccgcgtgc    1680
cgcagattcc gttcggctcc tccgtgcaca ttgagcccta cacggagctg taccactact    1740
ccacctcagt gatcacttcc tcctccaccc gggagtacac ggtgactgag cccgagcgag    1800
atggggcatc tccttcacgc atctacactt accagtggcg ccagaccatc accttccagg    1860
aatgcgtcca cgatgactcc cggccagccc tgcccagcac ccagcagctc tcggtggaca    1920
gcgtgttcgt cctgtacaac caggaggaga agatcttgcg ctatgctctc agcaactcca    1980
ttgggcctgt gagggaaggc tcccctgatg ctcttcagaa tccctgctac atcggcactc    2040
atgggtgtga caccaacgcg gcctgtcgcc ctggtcccag gacacagttc acctgcgagt    2100
gctccatcgg cttccgagga gacgggcgaa cctgctatga tattgatgaa tgttcagaac    2160
aaccctcagt gtgtgggagc cacacaatct gcaataatca cccaggaacc ttccgctgcg    2220
agtgtgtgga gggctaccag ttttcagatg agggaacgtg tgtggctgtc gtggaccagc    2280
gccccatcaa ctactgtgaa actggccttc ataactgcga catacccag cgggcccagt      2340 gtatctacac aggaggctcc tcctacacct gttcctgctt gccaggcttt tctggggatg    2400
gccaagcctg ccaagatgta gatgaatgcc agccaagccg atgtcaccct gacgccttct    2460
gctacaacac tccaggctct ttcacgtgcc agtgcaaacc tggttatcag ggagacggct    2520
tccgttgcgt gccggagag gtggagaaaa cccggtgcca gcacgagcga gaacacattc      2580
tcggggcagc ggggcgaca gacccacagc gacccattcc tccggggctg ttcgttcctg      2640
agtgcgatgc gcacgggcac tacgcgccca cccagtgcca cggcagcacc ggctactgct    2700
ggtgcgtgga tcgcgacggc cgcgaggtgg agggcaccag gaccaggccc gggatgacgc    2760
ccccgtgtct gagtacagtg gctccccga ttcaccaagg acctgcggtg cctaccgccg      2820
tgatcccctt gcctcctggg acccattac tctttgccca gactgggaag attgagcgcc      2880 tgccctgga gggaaatacc atgaggaaga cagaagcaaa ggcgttcctt catgtcccgg      2940
ctaaagtcat cattggactg gcctttgact gcgtggacaa gatggtttac tggacggaca    3000
tcactgagcc ttccattggg agagctagtc tacatggtgg agagccaacc accatcatta    3060
gacaagatct tggaagtcca gaaggtatcg ctgttgatca ccttggccgc aacatcttct    3120
ggacagactc taacctggat cgaatagaag tggcgaagct ggacggcacg cagcgccggg    3180
tgctctttga gactgacttg gtgaatccca gaggcattgt aacggattcc gtgagaggga    3240
acctttactg gacagactgg aacagagata accccaagat tgaaacttcc tacatggacg    3300
```

```
gcacgaaccg gaggatcctt gtgcaggatg acctgggctt gcccaatgga ctgaccttcg    3360
atgcgttctc atctcagctc tgctgggtgg atgcaggcac caatcgggcg gaatgcctga    3420 acccagtca gcccagcaga cgcaaggctc tcgaagggct ccagtatcct tttgctgtga     3480
cgagctacgg gaagaatctg tatttcacag actggaagat gaattccgtg gttgctctcg    3540
atcttgcaat ttccaaggag acggatgctt ccaaccccca caagcagacc cggctgtatg    3600
gcatcaccac ggccctgtct cagtgtccgc aaggccataa ctactgctca gtgaacaatg    3660
gcggctgcac ccacctatgc ttggccaccc cagggagcag gacctgccgt tgccctgaca    3720
acaccttggg agttgactgt atcgaacaga aatgaagaca agagtgcctt atttcctttc    3780
caagtatttc acagcaacac tctacttgaa gcaacttggt ccagattgaa aagtgtcctc    3840
tggctgagtg gccactaggc ccagaccag cccagcctga gccccaacaa cttttccctc      3900
actgttcccc aaaacatgca ccctggactt ctctaataga aaagtctcca cccctacaca    3960
aggacagaac cctccacccc tacccccaac cctcagacag acttatacac ccctgagtga    4020
ggattacatg cccatcccag tgtcctagga ccttttccca atactagccc cccagtggtg    4080
aacagaacct cccaaatttg agttgcaccc ttccctgtgg ccttatgagc tcagcctcgc    4140
tttgaggtac ccaccgtcct gtcagctcct tgacctatga gccggggcct gactaggaaa    4200
agttgggagt taaggaggaa attagcattc cttaatgttt tgttttggtg ctctgaattt    4260
cttctttatt atagtcctat agttttactc ctcagttcct caccatcatc atcttgtcta    4320
agacccccat tataatattc atgcgctgct ttttcatcaa aacctaccct gtcctagaga    4380
tctatgggca tttggtggat gataatgagc agccctccc agatagaatg tcaatatttg     4440
agcagtagga tattggcatt tgttagttaa aggcttaaat caaaagaatg tccaatggta    4500
ggaatttcaa ggtgtaggtc agatatttga gaataggggga tttttttgat gtgccttaaa   4560
ttataccaaa gattactaat tattcctctt tgcccaaaat acttgcatcc aaggttctag    4620
tctctgttgc tgtgctggtc tttagcccca ctgcttgcac tgatgtccct ccttttcacg    4680
gagacctatc tgaggtacag gatggggctg gcaccagatg atgtcccacc acagtccctc    4740
acctccggcc tccacatgac agaaccaatt tacactcaac catgacctca cccctccttg    4800
gtttctccct cgatctgtgg cccttttggg atgtattctt atctaacaac acaatccgga    4860
aagactgaat tgaatattta tactaatggt tcatatcctt tattgctcaa tgatctaatt    4920
aaagggatca ttgccacatt tcatgtttat atttctacaa tttgtttaga aaacatctcc    4980
tgaccatatc agtagctcgt gttatctttt tatcaactgc ttcccagagt cctaaaacaa    5040
tagaaatttt ggattgaaaa gttcagcata aggagtttga gtcagtaaag gatgggataa    5100
aggagtcgag atgattcaat gaaaagtatc acaaaaaaga gattgatcaa caagagaaat    5160
aaaaaagccc aagaggaagt ggtaggggaa ggaatttaag aacagcaata agtaaaactc    5220
ttaagtaact ccaaaaagaa aatggtacat tttgccaaag accacttata cttgagaaca    5280
tggaagaatt tgcctgatac tctctttggg gaaaagagtc tctcctcttt tcctcaaacc    5340
ccagtacact cagcctctct gccccacctt ctcctgactt tgtcctcact tgcttctgca    5400
gtacattgga acctgaattg aaagaaagtc ttccttgaat aattggagtt tgtcttgaga    5460
ggcaaatata gccccaagaa tcacaagatt cgaggaccat gtaggtcttt tacgtagccc    5520
aaatccataa attagtctca cttttttgtat ttatcgtttc atattaaacc ctctatatca    5580
aatgttcatg atgattttgt atgattttta aactatttt attcatttta ttagatttat     5640
tctaaaattt tttaatggta aattcttaaa ctgtggaaac cactgaaggt gcttattaac    5700
```

```
tgttctccca gatttgtaca agtattggat gattccttga gtttacagct gtacaaatag    5760
tgtggaaaat aaactttttt taaaaaagaa aa                                  5792
```